United States Patent
Chittaboina et al.

(10) Patent No.: US 12,398,107 B2
(45) Date of Patent: Aug. 26, 2025

(54) FUNGICIDAL NITROANILINO SUBSTITUTED PYRAZOLES

(71) Applicant: FMC Corporation, Philadelphia, PA (US)

(72) Inventors: Srinivas Chittaboina, Bibipet (IN); Jeffrey Keith Long, Wilmington, DE (US); Travis Chandler McMahon, Middletown, DE (US)

(73) Assignee: FMC Corporation, Phildelphia, PA (US)

( * ) Notice: Subject to any disclaimer, the term of this patent is extended or adjusted under 35 U.S.C. 154(b) by 838 days.

(21) Appl. No.: 17/274,223

(22) PCT Filed: Sep. 6, 2019

(86) PCT No.: PCT/US2019/049861
§ 371 (c)(1),
(2) Date: Mar. 8, 2021

(87) PCT Pub. No.: WO2020/051402
PCT Pub. Date: Mar. 12, 2020

(65) Prior Publication Data
US 2021/0317087 A1 Oct. 14, 2021

Related U.S. Application Data

(60) Provisional application No. 62/727,727, filed on Sep. 6, 2018.

(51) Int. Cl.
| | | |
|---|---|---|
| *C07D 231/38* | (2006.01) |
| *A01N 25/04* | (2006.01) |
| *A01N 25/08* | (2006.01) |
| *A01N 25/14* | (2006.01) |
| *A01N 25/30* | (2006.01) |
| *A01N 43/56* | (2006.01) |

(52) U.S. Cl.
CPC ........... *C07D 231/38* (2013.01); *A01N 25/04* (2013.01); *A01N 25/08* (2013.01); *A01N 25/14* (2013.01); *A01N 25/30* (2013.01); *A01N 43/56* (2013.01)

(58) Field of Classification Search
None
See application file for complete search history.

(56) References Cited

U.S. PATENT DOCUMENTS

2011/0319430 A1* 12/2011 Long .................... C07D 417/12
548/366.1

FOREIGN PATENT DOCUMENTS

| WO | 93/19054 A1 | 9/1993 |
| WO | 2010/101973 A1 | 9/2010 |
| WO | 2012/031061 A2 | 3/2012 |
| WO | 2013/116251 A2 | 8/2013 |
| WO | 2013/192126 A1 | 12/2013 |
| WO | 2016/012424 A1 | 1/2016 |
| WO | 2018/052838 A1 | 3/2018 |
| WO | WO-2019020981 A1 * | 1/2019 |

OTHER PUBLICATIONS

International Search Report for corresponding PCT/US2019/049861 patent application.

* cited by examiner

*Primary Examiner* — Anna R Falkowitz
*Assistant Examiner* — Edwin Coleman Mitchell

(57) ABSTRACT

Disclosed are compounds of Formula 1, including all geometric and stereoisomers, tautomers, N oxides, and salts thereof, wherein $R^1$, $R^2$, $R^3$, $R^4$, $R^5$, $R^6$, m and n are as defined in the disclosure. Also disclosed are compositions containing the compounds of Formula 1 and methods for controlling plant disease caused by a fungal pathogen comprising applying an effective amount of a compound or a composition of the invention.

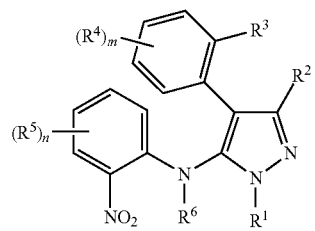

4 Claims, No Drawings

FUNGICIDAL NITROANILINO SUBSTITUTED PYRAZOLES

FIELD OF THE INVENTION

This invention relates to certain pyrazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publications WO 2018/052838, WO 2013/192126, WO 2012/031061 and WO 2010/101973 disclose fungicidal pyrazoles and their use in agriculture. PCT Patent Publication WO 2019/020981 discloses pyrazole, isothiazole and isoxazole derivatives and their use in agriculture.

SUMMARY OF THE INVENTION

This invention is directed to compounds of Formula 1 (including all stereoisomers), N-oxides, and salts thereof, agricultural compositions containing them and their use as fungicides:

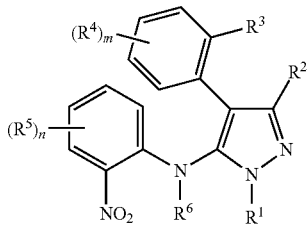

wherein
- $R^1$ is $C_1$-$C_2$ alkyl;
- $R^2$ is cyano, halogen, $C_1$-$C_2$ alkyl or $C_1$-$C_2$ haloalkyl;
- $R^3$ is halogen or methyl;
- each $R^4$ is independently halogen, cyano, nitro, $C_1$-$C_3$ alkyl, $C_1$-$C_3$ alkoxy, $C_1$-$C_3$ haloalkoxy, $C_2$-$C_6$ alkenyloxy, $C_2$-$C_6$ alkynyloxy, $C_2$-$C_6$ cyanoalkoxy, $C_2$-$C_6$ alkoxyalkyl or $C_2$-$C_6$ alkoxyalkoxy;
- each $R^5$ is independently halogen, $C_1$-$C_3$ alkyl, $C_2$-$C_6$ alkoxyalkyl, $C_1$-$C_3$ alkoxy, $C_1$-$C_3$ haloalkoxy, $C_2$-$C_6$ alkenyloxy, $C_2$-$C_6$ alkynyloxy, $C_2$-$C_6$ cyanoalkoxy or $C_2$-$C_6$ alkoxyalkoxy;
- m and n are each independently 0, 1, 2 or 3;
- $R^6$ is H; or $C_1$-$C_3$ alkyl or $C_1$-$C_3$ haloalkyl, each optionally substituted with up to 2 substituents independently selected from $R^{6a}$; or amino, $C_2$-$C_4$ alkenyl, $C_2$-$C_4$ alkynyl, $C_3$-$C_6$ cycloalkyl, CH(=O), S(=O)$_2$OM, S(=O)$_u$R$^7$, (C=W)R$^8$ or OR$^9$;
- each $R^{6a}$ is independently cyano, $C_3$-$C_6$ cycloalkyl, $C_1$-$C_3$ alkoxy, $C_1$-$C_3$ haloalkoxy, $C_1$-$C_3$ alkylthio, $C_1$-$C_3$ alkylsulfinyl or $C_1$-$C_3$ alkylsulfonyl;
- M is K or Na;
- u is 0, 1 or 2;
- $R^7$ is $C_1$-$C_3$ alkyl or $C_1$-$C_3$ haloalkyl;
- W is O or S;
- $R^8$ is $C_1$-$C_3$ alkyl, $C_2$-$C_4$ alkoxyalkyl, $C_2$-$C_4$ alkylaminoalkyl, $C_3$-$C_6$ dialkylaminoalkyl, $C_1$-$C_3$ alkoxy, $C_1$-$C_3$ alkylthio or $C_2$-$C_4$ alkylthioalkyl;
- $R^9$ is H; or $C_1$-$C_3$ alkyl or $C_1$-$C_3$ haloalkyl, each optionally substituted with up to 2 substituents independently selected from $R^{9a}$; or CH(=O), $C_3$-$C_6$ cycloalkyl, S(=O)$_2$OM or (C=W)R$^{10}$;
- each $R^{9a}$ is independently cyano, $C_3$-$C_6$ cycloalkyl, $C_1$-$C_3$ alkoxy, $C_1$-$C_3$ haloalkoxy, $C_1$-$C_3$ alkylthio, $C_1$-$C_3$ alkylsulfinyl or $C_1$-$C_3$ alkylsulfonyl; and
- $R^{10}$ is $C_1$-$C_3$ alkyl, $C_2$-$C_4$ alkoxyalkyl, $C_2$-$C_4$ alkylaminoalkyl, $C_3$-$C_6$ dialkylaminoalkyl, $C_1$-$C_3$ alkoxy, $C_1$-$C_3$ alkylthio or $C_2$-$C_4$ alkylthioalkyl;

provided that the compound of Formula 1 is not:
4-(2,6-difluoro-4-methoxyphenyl)-N-(2,4-difluoro-6-nitrophenyl)-1,3-dimethyl-1H-pyrazol-5-amine;
4-(2-chloro-4-fluorophenyl)-1,3-dimethyl-N-(2-nitrophenyl)-1H-pyrazol-5-amine;
4-(2-chloro-4-fluorophenyl)-N-(2,4-difluoro-6-nitrophenyl)-1,3-dimethyl-1H-pyrazol-5-amine;
4-(2-chloro-4-fluorophenyl)-3-ethyl-1-methyl-N-(2-nitrophenyl)-1H-pyrazol-5-amine;
4-(2-chloro-4-fluorophenyl)-1-methyl-N-(2-nitrophenyl)-3-(trifluoromethyl)-1H-pyrazol-5-amine;
4-(2,6-difluoro-4-methoxyphenyl)-N-(2-methoxy-6-nitrophenyl)-1,3-dimethyl-1H-pyrazol-5-amine;
4-(2-chloro-4-fluorophenyl)-N-(2-methoxy-6-nitrophenyl)-1,3-dimethyl-1H-pyrazol-5-amine;
N-(2-chloro-6-nitrophenyl)-4-(2,6-difluoro-4-methoxyphenyl)-1,3-dimethyl-1H-pyrazol-5-amine;
N-(2-chloro-3-fluoro-6-nitrophenyl)-4-(2,6-difluoro-4-methoxyphenyl)-1,3-dimethyl-1H-pyrazol-5-amine;
4-(2-chloro-4-fluorophenyl)-1,3-dimethyl-N-(2-methyl-6-nitrophenyl)-1H-pyrazol-5-amine;
N-(2-bromo-4-fluoro-6-nitrophenyl)-4-(2-chloro-4-fluorophenyl)-1,3-dimethyl-1H-pyrazol-5-amine;
4-(2-chloro-4-fluorophenyl)-N-(4-methoxy-2-nitrophenyl)-1,3-dimethyl-1H-pyrazol-5-amine;
4-(2,6-difluoro-4-methoxyphenyl)-N-(4-fluoro-2-nitrophenyl)-1,3-dimethyl-1H-pyrazol-5-amine;
4-(2,6-difluoro-4-methoxyphenyl)-N-(4-methoxy-2-nitrophenyl)-1,3-dimethyl-1H-pyrazol-5-amine;
N-(4-chloro-2-nitrophenyl)-4-(2,6-difluoro-4-methoxyphenyl)-1,3-dimethyl-1H-pyrazol-5-amine;
4-(2,6-difluoro-4-methoxyphenyl)-1,3-dimethyl-N-[2-nitro-4-(2-propyn-1-yloxy) phenyl]-1H-pyrazol-5-amine;
4-(2,6-difluoro-4-methoxyphenyl)-1,3-dimethyl-N-[2-nitro-4-(2-propen-1-yloxy) phenyl]-1H-pyrazol-5-amine;
N-(4-bromo-2-nitrophenyl)-4-(2,6-difluoro-4-methoxyphenyl)-1,3-dimethyl-1H-pyrazol-5-amine;
N-(4-chloro-2-fluoro-6-nitrophenyl)-4-(2,6-difluoro-4-methoxyphenyl)-1,3-dimethyl-1H-pyrazol-5-amine;
3-chloro-4-(2-chloro-4-fluorophenyl)-N-(2,4-difluoro-6-nitrophenyl)-1-methyl-1H-pyrazol-5-amine;
4-(2,6-difluoro-4-methoxyphenyl)-1,3-dimethyl-N-[4-methyl-2-nitrophenyl]-1H-pyrazol-5-amine;
4-(2-chloro-4-fluorophenyl)-1,3-dimethyl-N-(4-methyl-2-nitrophenyl)-1H-pyrazol-5-amine; and
N-(4-bromo-2-fluoro-6-nitrophenyl)-4-(2,6-difluoro-4-methoxyphenyl)-1,3-dimethyl-1H-pyrazol-5-amine.

More particularly, this invention pertains to a compound of Formula 1 (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

This invention also relates to a composition comprising a compound of Formula 1, an N-oxide, or a salt thereof, and at least one invertebrate pest control compound or agent.

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As referred to in this disclosure, the terms "fungal pathogen" and "fungal plant pathogen" include pathogens in the Ascomycota, Basidiomycota and Zygomycota phyla, and the fungal-like Oomycota class that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As used herein, the term "mode of action" (MOA) is as define by the Fungicide Resistance Action Committee (FRAC), and is used to distinguish fungicides according to their biochemical mode of action in the biosynthetic pathways of plant pathogens, and their resistance risk. FRAC-defined modes of actions include (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis, (I) melanin synthesis in cell wall, (P) host plant defense induction, (U) unknown mode of action, (NC) not classified, (M) multi-site contact activity and (BM) biologicals with multiple modes of action. Each mode of action (i.e. letters A through BM) contain one or more subgroups (e.g., A includes subgroups A1, A2, A3 and A4) based either on individual validated target sites of action, or in cases where the precise target site is unknown, based on cross resistance profiles within a group or in relation to other groups. Each of these subgroups (e.g., A1, A2, A3 and A4) is assigned a FRAC code (a number and/or letter). For example, the FRAC code for subgroup A1 is 4. Additional information on target sites and FRAC codes can be obtained from publicly available databases maintained, for example, by FRAC.

As used herein, the term "cross resistance" refers to the phenomenon that occurs when a pathogen develops resistance to one fungicide and simultaneously becomes resistant to one or more other fungicides. These other fungicides are typically, but not always, in the same chemical class or have the same target site of action, or can be detoxified by the same mechanism.

As used herein, the term "cross resistance" refers to the phenomenon that occurs when a pathogen develops resistance to one fungicide and simultaneously becomes resistant to one or more other fungicides. These other fungicides are typically, but not always, in the same chemical class or have the same target site of action, or can be detoxified by the same mechanism.

Generally when a molecular fragment (i.e. radical) is denoted by a series of atom symbols (e.g., C, H, N, O and S) the implicit point or points of attachment will be easily recognized by those skilled in the art. In some instances herein, particularly when alternative points of attachment are possible, the point or points of attachment may be explicitly indicated by a hyphen ("-"). For example, "-NCS" indicates that the point of attachment is the nitrogen atom (i.e. isothiocyanato, not thiocyanato).

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified, for example, for $R^5$.

In the above recitations, the term "alkyl", used either alone or in compound words such as "alkylthio" or "haloalkyl" includes straight-chain or branched alkyl such as methyl, ethyl, n-propyl and i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, i-propyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyl attached to and linked through an oxygen atom. Examples of "alkenyloxy" include $H_2C=CHCH_2O$, $(CH_3)_2C=CHCH_2O$, $CH_3CH=CHCH_2O$, $CH_3CH=C(CH_3)CH_2O$ and $CH_2=CHCH_2CH_2O$. "Alkynyloxy" includes straight-chain or branched alkynyl attached to and linked through an oxygen atom. Examples of "alkynyloxy" include $HC\equiv CCH_2O$, $CH_3C\equiv CCH_2O$ and $CH_3C\equiv CCH_2CH_2O$. "Alkoxyalkoxy" denotes alkoxy substitution on another alkoxy moiety. Examples of "alkoxyalkoxy" include $CH_3OCH_2O$, $CH_3OCH_2O$ and $CH_3CH_2OCH_2O$.

"Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$ and $CH_3CH_2SCH_2CH_2$. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$ and $(CH_3)_2CHS(=O)$. Examples of "alkyl sulfonyl" include $CH_3S(=O)_2$, $CH_3CH_2S(=O)_2$, $CH_3CH_2CH_2S(=O)_2$ and $(CH_3)_2CHS(=O)_2$.

"Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2CH_2NHCH_2$ and $CH_3CH_2NHCH_2CH_2$.

Examples of "dialkylaminoalkyl" include $(CH_3)_2NCH_2$, $(CH_3CH_2)_2NCH_2CH_2$ and $CH_3CH_2(CH_3)N$ $CH_2CH_2$.

The term "cycloalkyl" denotes a saturated carbocyclic ring consisting of between 3 to 6 carbon atoms linked to one another by single bonds. Examples of "cycloalkyl" include cyclopropyl, cyclobutyl, cyclopentyl and cyclohexyl. The term "cycloalkylalkyl" denotes cycloalkyl substitution on an alkyl group. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The term "haloalkoxy", and the like, are defined analogously to the term "haloalkyl". Examples of "haloalkoxy" include $CF_3O$, $CCl_3CH_2O$, $F_2CHCH_2CH_2O$ and $CF_3CH_2O$.

"Cyanoalkoxy" denotes an alkyloxy group substituted with one cyano group. Examples of "cyanoalkoxy" include $NCCH_2O$, $NCCH_2CH_2O$ and $CH_3CH(CN)CH_2O$.

The total number of carbon atoms in a substituent group is indicated by the "$C_i$-$C_j$" prefix where i and j are numbers from 1 to 6. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) range from 1 to 3. As used herein, the term "optionally substituted" is used interchangeably with the phrase "substituted or unsubstituted" or with the term "(un)substituted."

The number of optional substituents may be restricted by an expressed limitation. For example, the phrase "optionally substituted with up to 2 substituents independently selected from $R^{6a}$" means that 0, 1 or 2 substituents can be present.

When a compound is substituted with a substituent bearing a subscript that indicates the number of said substituents can vary (e.g., $(R^4)_m$ in Formula 1 wherein m is 0 to 3), then said substituents are independently selected from the group of defined substituents, unless otherwise indicated. When a variable group is shown to be optionally attached to a position, for example $(R^4)_m$ wherein m may be 0, then hydrogen may be at the position even if not recited in the definition of the variable group.

Naming of substituents in the present disclosure uses recognized terminology providing conciseness in precisely conveying to those skilled in the art the chemical structure. For sake of conciseness, locant descriptors may be omitted. In some instances herein the point or points of attachment of substituents (e.g., $R^4$ and $R^5$) are indicated by locant numbers which may be different from the Chemical Abstracts naming system if the difference does not affect the meaning.

Compounds of this invention can exist as one or more stereoisomers. Stereoisomers are isomers of identical constitution but differing in the arrangement of their atoms in space and include enantiomers, diastereomers, cis- and trans-isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

Compounds of this invention can exist as one or more conformational isomers due to restricted rotation about an amide bond (e.g., C(=O)—N) in Formula 1. This invention comprises mixtures of conformational isomers. In addition, this invention includes compounds that are enriched in one conformer relative to others.

This invention comprises all stereoisomers, conformational isomers and mixtures thereof in all proportions as well as isotopic forms such as deuterated compounds.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus, a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds selected from Formula 1, stereoisomers, N-oxides, and salts thereof, typically exist in more than one form, therefore Formula 1 includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes stereoisomers, N-oxides, and salts thereof, and reference to "a compound of Formula 1" includes the definitions of substituents specified in the Summary of the Invention unless further defined in the Embodiments.

Embodiment 1. A compound of Formula 1 wherein $R^1$ is methyl.

Embodiment 2. A compound of Formula 1 wherein $R^1$ is ethyl.

Embodiment 3. A compound of Formula 1 or Embodiments 1 or 2 wherein $R^2$ is cyano, halogen or $C_1$-$C_2$ alkyl.

Embodiment 4. A compound of Formula 1 or Embodiments 1 or 2 wherein $R^2$ is cyano, Br, Cl, F, $C_1$-$C_2$ alkyl or $C_1$-$C_2$ haloalkyl.

Embodiment 5. A compound of Embodiment 4 wherein $R^2$ is cyano, Br, Cl, F, $C_1$-$C_2$ alkyl or halomethyl.

Embodiment 6. A compound of Embodiment 5 wherein $R^2$ is cyano, Br, Cl, F, $C_1$-$C_2$ alkyl or $CF_3$.

Embodiment 7. A compound of Embodiment 6 wherein $R^2$ is cyano, Br, Cl, F or $C_1$-$C_2$ alkyl.

Embodiment 8. A compound of Embodiment 7 wherein $R^2$ is cyano or $C_1$-$C_2$ alkyl.

Embodiment 9. A compound of Embodiment 8 wherein $R^2$ is $C_1$-$C_2$ alkyl.

Embodiment 10. A compound of Embodiment 8 wherein $R^2$ is cyano or methyl.

Embodiment 11. A compound of Embodiment 10 wherein $R^2$ is methyl.

Embodiment 12. A compound of Embodiment 7 wherein $R^2$ is Br, Cl or methyl.

Embodiment 13. A compound of Formula 1 or any one of Embodiments 1 through 12 wherein $R^3$ is halogen or methyl.

Embodiment 13a. A compound of Embodiment 13 wherein $R^3$ is halogen.

Embodiment 13b. A compound of Embodiment 13 wherein $R^3$ is Br, Cl, F or methyl.

Embodiment 14. A compound of Embodiment 13 wherein $R^3$ is Br, Cl or F.

Embodiment 15. A compound of Embodiment 14 wherein $R^3$ is Cl or F.

Embodiment 16. A compound of Embodiment 15 wherein $R^3$ is Cl.

Embodiment 17. A compound of Embodiment 15 wherein $R^3$ is F.

Embodiment 18. A compound of Embodiment 13 wherein $R^3$ is Cl, F or methyl.

Embodiment 19. A compound of Embodiment 18 wherein $R^3$ is Cl or methyl.

Embodiment 20. A compound of Embodiment 19 wherein $R^3$ is methyl.

Embodiment 21. A compound of Formula 1 or any one of Embodiments 1 through 20 wherein each $R^4$ is independently halogen, cyano, $C_1$-$C_2$ alkyl, $C_1$-$C_2$ alkoxy, $C_1$-$C_2$ haloalkoxy, $C_2$-$C_4$ alkenyloxy, $C_2$-$C_4$ alkynyloxy, $C_2$-$C_4$ cyanoalkoxy, $C_2$-$C_4$ alkoxyalkyl or $C_2$-$C_4$ alkoxyalkoxy.

Embodiment 22. A compound of Embodiment 21 wherein each $R^4$ is independently halogen, cyano, methyl, methoxy, halomethoxy, $C_2$-$C_4$ alkenyloxy, $C_2$-$C_4$ alkynyloxy, $C_2$-$C_4$ cyanoalkoxy, $C_2$-$C_4$ alkoxyalkyl or $C_2$-$C_4$ alkoxyalkoxy.

Embodiment 23. A compound of Embodiment 22 wherein each $R^4$ is independently halogen, cyano, methyl, methoxy, halomethoxy, $C_2$-$C_4$ alkenyloxy, $C_2$-$C_4$ alkynyloxy or $C_2$-$C_4$ cyanoalkoxy.

Embodiment 24. A compound of Embodiment 23 wherein each $R^4$ is independently halogen, cyano, methyl, methoxy, halomethoxy or $C_2$-$C_4$ cyanoalkoxy.

Embodiment 25. A compound of Embodiment 24 wherein each $R^4$ is independently halogen, cyano, methyl or methoxy.

Embodiment 25a. A compound of Embodiment 25 wherein each $R^4$ is independently halogen, cyano or methoxy.

Embodiment 25b. A compound of Embodiment 25 wherein each $R^4$ is independently halogen, cyano or methyl.

Embodiment 26. A compound of Embodiment 25 wherein each $R^4$ is independently Br, Cl, F, cyano, methyl or methoxy.

Embodiment 27. A compound of Embodiment 26 wherein each $R^4$ is independently Br, Cl, F, cyano or methoxy.

Embodiment 28. A compound of Embodiment 27 wherein each $R^4$ is independently Cl, F, cyano or methoxy.

Embodiment 29. A compound of Embodiment 27 wherein each $R^4$ is independently Br, Cl or F.

Embodiment 30. A compound of Embodiment 29 wherein each $R^4$ is independently Cl or F.

Embodiment 31. A compound of Embodiment 30 wherein each $R^4$ is Cl.

Embodiment 32. A compound of Embodiment 30 wherein each $R^4$ is F.

Embodiment 33. A compound of Formula 1 or any one of Embodiments 1 through 32 wherein each $R^4$ is independently halogen, cyano or $C_1$-$C_2$ alkoxy.

Embodiment 34. A compound of of Embodiment 33 wherein each $R^4$ is independently halogen.

Embodiment 35. A compound of of Embodiment 33 wherein each $R^4$ is independently Br, Cl or F or cyano.

Embodiment 36. A compound of Formula 1 or any one of Embodiments 1 through 35 wherein m is 0, 1 or 2.

Embodiment 37. A compound of Embodiment 36 wherein m is 1 or 2.

Embodiment 38. A compound of Embodiment 37 wherein m is 1.

Embodiment 39. A compound of Embodiment 38 wherein m is 2.

Embodiment 40. A compound of Formula 1 or any one of Embodiments 1 through 39 wherein each $R^5$ is independently halogen, $C_1$-$C_2$ alkyl, $C_2$-$C_4$ alkoxyalkyl, $C_1$-$C_2$ alkoxy, $C_1$-$C_2$ haloalkoxy, $C_2$-$C_4$ alkenyloxy, $C_2$-$C_4$ alkynyloxy, $C_2$-$C_4$ cyanoalkoxy or $C_2$-$C_4$ alkoxyalkoxy.

Embodiment 41. A compound of Embodiment 40 wherein each $R^5$ is independently halogen, methyl, methoxy, halomethoxy, $C_2$-$C_4$ alkenyloxy, $C_2$-$C_4$ alkynyloxy or $C_2$-$C_4$ cyanoalkoxy.

Embodiment 42. A compound of Embodiment 41 wherein each $R^5$ is independently halogen, methyl, methoxy, halomethoxy, $C_2$-$C_4$ alkenyloxy or $C_2$-$C_4$ cyanoalkoxy.

Embodiment 43. A compound of Embodiment 42 wherein each $R^5$ is independently halogen, methyl, methoxy, halomethoxy or $C_2$-$C_4$ cyanoalkoxy.

Embodiment 44. A compound of Embodiment 43 wherein each $R^5$ is independently halogen, methyl or methoxy.

Embodiment 45. A compound of Embodiment 44 wherein each $R^5$ is independently Br, Cl, F, methyl or methoxy.

Embodiment 46. A compound of Embodiment 45 wherein each $R^5$ is independently Br, Cl, F or methoxy.

Embodiment 46a. A compound of Embodiment 46 wherein each $R^5$ is independently Br, Cl or F.

Embodiment 47. A compound of Embodiment 46 wherein each $R^5$ is independently Cl, F or methoxy.

Embodiment 48. A compound of Embodiment 47 wherein each $R^5$ is independently Cl or F.

Embodiment 49. A compound of Embodiment 45 wherein each $R^5$ is independently Br, Cl, F or methyl.

Embodiment 50. A compound of Embodiment 49 wherein each $R^5$ is independently F or methyl.

Embodiment 51. A compound of Embodiment 50 wherein each $R^5$ is F.

Embodiment 52. A compound of Formula 1 or any one of Embodiments 1 through 51 wherein n is 0, 1 or 2.

Embodiment 53. A compound of Embodiment 52 wherein n is 1 or 2.

Embodiment 54. A compound of Embodiment 53 wherein n is 1.

Embodiment 55. A compound of Embodiment 53 wherein n is 2.

Embodiment 56. A compound of Formula 1 or any one of Embodiments 1 through 55 wherein $R^6$ is H; or $C_1$-$C_3$ alkyl or $C_1$-$C_3$ haloalkyl, each optionally substituted with up to 1 substituent selected from $R^{6a}$; or amino, $C_2$-$C_3$ alkenyl, $C_2$-$C_3$ alkynyl, cyclopropyl, CH(=O), S(=O)$_2$OM, S(=O)$_u$R$^7$, (C=W)R$^8$ or OR$^9$.

Embodiment 57. A compound of Embodiment 56 wherein $R^6$ is H; or $C_1$-$C_3$ alkyl or $C_1$-$C_3$ haloalkyl, each optionally substituted with up to 1 substituent selected from $R^{6a}$; or cyclopropyl, $S(=O)_2OM$, $S(=O)_uR^7$, $(C=W)R^8$ or $OR^9$.

Embodiment 58. A compound of Embodiment 57 wherein $R^6$ is H; or $C_1$-$C_2$ alkyl or $C_1$-$C_2$ haloalkyl, each optionally substituted with up to 1 substituent selected from $R^{6a}$; or $S(=O)_uR^7$ or $OR^9$.

Embodiment 59. A compound of Embodiment 58 wherein $R^6$ is H; or $C_1$-$C_2$ alkyl or $C_1$-$C_2$ haloalkyl, each optionally substituted with up to 1 substituent selected from $R^{6a}$.

Embodiment 60. A compound of Embodiment 59 wherein $R^6$ is H, $C_1$-$C_2$ alkyl or $C_1$-$C_2$ haloalkyl.

Embodiment 61. A compound of Embodiment 60 wherein $R^6$ is H, methyl or halomethyl.

Embodiment 62. A compound of Embodiment 61 wherein $R^6$ is H, methyl or trifluoromethyl.

Embodiment 63. A compound of Embodiment 62 wherein $R^6$ is H or methyl.

Embodiment 64. A compound of Embodiment 63 wherein $R^6$ is H.

Embodiment 65. A compound of Formula 1 or any one of Embodiments 1 through 64 wherein each $R^{6a}$ is independently cyano, $C_3$-$C_6$ cycloalkyl or $C_1$-$C_3$ alkoxy.

Embodiment 66. A compound of Embodiment 65 wherein each $R^{6a}$ is independently cyano, cyclopropyl or methoxy.

Embodiment 67. A compound of Embodiment 66 wherein each $R^{6a}$ is independently cyano or cyclopropyl.

Embodiment 68. A compound of Formula 1 or any one of Embodiments 1 through 58 wherein u is 0.

Embodiment 69. A compound of Formula 1 or any one of Embodiments 1 through 58 wherein $R^7$ is methyl or halomethyl.

Embodiment 70. A compound of Formula 1 or any one of Embodiments 1 through 57 wherein W is O.

Embodiment 71. A compound of Formula 1 or any one of Embodiments 1 through 57 wherein $R^8$ is $C_1$-$C_3$ alkyl, $C_1$-$C_3$ alkoxy or $C_1$-$C_3$ alkylthio.

Embodiment 72. A compound of Embodiment 71 wherein $R^8$ is methyl, ethyl, methoxy, ethoxy, methylthio or ethylthio.

Embodiment 73. A compound of Embodiment 72 wherein $R^8$ is methyl, methoxy or methylthio.

Embodiment 74. A compound of Formula 1 or any one of Embodiments 1 through 58 wherein $R^9$ is H; or $C_1$-$C_3$ alkyl or $C_1$-$C_3$ haloalkyl, each optionally substituted with up to 1 substituent selected from $R^{9a}$; or $CH(=O)$, cyclopropyl, $S(=O)_2OM$ or $(C=W)R^{10}$.

Embodiment 75. A compound of Embodiment 74 wherein $R^9$ is H; or $C_1$-$C_2$ alkyl or $C_1$-$C_2$ haloalkyl, each optionally substituted with up to 1 substituent selected from $R^{9a}$.

Embodiment 76. A compound of Formula 1 or any one of Embodiments 1 through 75 wherein each $R^{9a}$ is independently cyano, $C_3$-$C_6$ cycloalkyl or $C_1$-$C_3$ alkoxy.

Embodiment 77. A compound of Embodiment 76 wherein each $R^{9a}$ is independently cyano, cyclopropyl or methoxy.

Embodiment 78. A compound of Embodiment 77 wherein each $R^{9a}$ is independently cyano or cyclopropyl.

Embodiment 79. A compound of Formula 1 or any one of Embodiments 1 through 78 wherein $R^{10}$ is $C_1$-$C_3$ alkyl, $C_1$-$C_3$ alkoxy or $C_1$-$C_3$ alkylthio.

Embodiment 80. A compound of Embodiment 79 wherein $R^{10}$ is methyl, ethyl, methoxy, ethoxy, methylthio or ethylthio.

Embodiment 81. A compound of Embodiment 80 wherein $R^{10}$ is methyl, methoxy or methylthio.

Embodiment 82. A compound of Formula 1 or any one of Embodiments 1 through 81 wherein m is 1 and $R^4$ is at the 4-position (or para position), relative to the connection of the phenyl ring to the remainder of Formula 1.

Embodiment 83. A compound of Formula 1 or any one of Embodiments 1 through 81 wherein m is 1 and $R^4$ is at the 6-position (or ortho position), relative to the connection of the phenyl ring to the remainder of Formula 1.

Embodiment 84. A compound of Formula 1 or any one of Embodiments 1 through 81 wherein m is 1 and $R^4$ is at the 4-position (or para position); or m is 1 and $R^4$ is at the 6-position (or ortho position), relative to the connection of the phenyl ring to the remainder of Formula 1.

Embodiment 85. A compound of Formula 1 or any one of Embodiments 1 through 81 wherein m is 2 and one $R^4$ is at the 4-position (or para position), and the other is at the 6-position (or ortho position), relative to the connection of the phenyl ring to the remainder of Formula 1).

Embodiment 86. A compound of Formula 1 or any one of Embodiments 1 through 81 wherein m is 1 and $R^4$ is at the 4-position (or para position); or m is 1 and $R^4$ is at the 6-position (or ortho position); or m is 2 and one $R^4$ is at the 4-position (or para position), and the other is at the 6-position (or ortho position), relative to the connection of the phenyl ring to the remainder of Formula 1.

Embodiment 86a. A compound of Embodiment 86 wherein m is 1 and $R^4$ is at the 4-position (or para position); or m is 2 and one $R^4$ is at the 4-position (or para position), and the other is at the 6-position (or ortho position), relative to the connection of the phenyl ring to the remainder of Formula 1.

Embodiment 87. A compound of Formula 1 or any one of Embodiments 1 through 86a wherein n is 1 and $R^5$ is at the 4-position (or the para position), relative to the connection of the nitoanilino ring to the remainder of Formula 1.

Embodiment 88. A compound of Formula 1 or any one of Embodiments 1 through 86a wherein n is 1 and $R^5$ is at the 6-position (or ortho position), relative to the connection of the nitoanilino ring to the remainder of Formula 1.

Embodiment 89. A compound of Formula 1 or any one of Embodiments 1 through 86a wherein n is 2 and one $R^5$ is at the 4-position (or para position), and the other is at the 6-position (or ortho position), relative to the connection of the nitoanilino ring to the remainder of Formula 1.

Embodiment 90. A compound of Formula 1 or any one of Embodiments 1 through 86a wherein n is 1 and $R^5$ is at the 4-position (or para position); or n is 1 and $R^5$ is at the 6-position (or ortho position); or n is 2 and one $R^5$ is at the 4-position (or para position), and the other is at the 6-position (or ortho position), relative to the connection of the nitoanilino ring to the remainder of Formula 1.

Embodiment 91. A compound of Formula 1 or any one of Embodiments 1 through 90 wherein m and n are each 1 and $R^4$ is at the 4-position (or para position), and $R^5$ is at the 6-position (or ortho position); or m is 1 and $R^4$ is at the 4-position (or para position), and n is 2 and one $R^5$ is at the 4-position (or para position) and the other is at the 6-position (or ortho position); or m and n are each 1 and $R^4$ is at the 4-position (or para position), and $R^5$ is at the 4-position (or para position); or m is 2 and one $R^4$ is at the 4-position (or para position) and the other is at the 6-position (or ortho position), and n is 1 and $R^5$ is at the 6-position (or ortho position), relative to the connection of the phenyl and nitoanilino rings to the remainder of Formula 1.

Embodiment 92. A compound of Embodiment 91 wherein m and n are each 1 and $R^4$ is at the 4-position (or para position) and $R^5$ is at the 6-position (or ortho position); or m is 1 and $R^4$ is at the 4-position (or para position), and n is 2 and one $R^5$ is at the 4-position (or para position) and the other is at the 6-position (or ortho position); m is 2 and one $R^4$ is at the 4-position (or para position) and the other is at the 6-position (or ortho position), and n is 1 and $R^5$ is at the 6-position (or ortho position), relative to the connection of the phenyl and nitoanilino rings to the remainder of Formula 1.

Embodiment 93. A compound of Embodiment 92 wherein m and n are each 1 and $R^4$ is at the 4-position (or para position) and $R^5$ is at the 6-position (or ortho position); or m is 1 and $R^4$ is at the 4-position (or para position), and n is 2 and one $R^5$ is at the 4-position (or para position) and the other is at the 6-position (or ortho position), relative to the connection of the phenyl and nitoanilino rings to the remainder of Formula 1.

Embodiment 94. A compound of Embodiment 93 wherein m and n are each 1 and $R^4$ is at the 4-position (or para position) and $R^5$ is at the 6-position (or ortho position).

Embodiment 95. A compound of Embodiment 93 wherein m is 1 and $R^4$ is at the 4-position (or para position), and n is 2 and one $R^5$ is at the 4-position (or para position) and the other is at the 6-position (or ortho position).

Embodiments of this invention, including Embodiments 1-95 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-95 above as well as any other embodiments described herein, and any combination thereof, pertain to the compositions and methods of the present invention.

Combinations of Embodiments 1-95 are illustrated by:

Embodiment A. A compound of Formula 1 wherein
$R^1$ is methyl;
$R^2$ is cyano, halogen or $C_1$-$C_2$ alkyl;
$R^3$ is halogen;
each $R^4$ is independently halogen, cyano, methyl, methoxy, halomethoxy, $C_2$-$C_4$ alkenyloxy, $C_2$-$C_4$ alkynyloxy or $C_2$-$C_4$ cyanoalkoxy;
each $R^5$ is independently halogen, methyl, methoxy, halomethoxy, $C_2$-$C_4$ alkenyloxy, $C_2$-$C_4$ alkynyloxy or $C_2$-$C_4$ cyanoalkoxy;
$R^6$ is H; or $C_1$-$C_2$ alkyl or $C_1$-$C_2$ haloalkyl, each optionally substituted with up to 1 substituent selected from $R^{6a}$; or $S(=O)_u R^7$ or $OR^9$;
$R^{6a}$ is cyano, $C_3$-$C_6$ cycloalkyl or $C_1$-$C_3$ alkoxy;
$R^7$ is methyl or halomethyl;
$R^9$ is H; or $C_1$-$C_2$ alkyl or $C_1$-$C_2$ haloalkyl, each optionally substituted with up to 1 substituent selected from $R^{9a}$; and
$R^{9a}$ is cyano, $C_3$-$C_6$ cycloalkyl or $C_1$-$C_3$ alkoxy.

Embodiment B. A compound of Embodiment A wherein
$R^2$ is methyl or ethyl;
$R^3$ is Br, Cl or F;
each $R^4$ is independently halogen, cyano, methyl or methoxy;
m is 1 and $R^4$ is at the 4-position (or para position); or m is 1 and $R^4$ is at the 6-position (or ortho position); or m is 2 and one $R^4$ is at the 4-position (or para position), and the other is at the 6-position (or ortho position);
each $R^5$ is independently halogen, methyl or methoxy;
n is 1 and $R^5$ is at the 4-position (or para position); or n is 1 and $R^5$ is at the 6-position (or ortho position); or n is 2 and one $R^5$ is at the 4-position (or para position), and the other is at the 6-position (or ortho position); and
$R^6$ is H or methyl.

Embodiment C. A compound of Embodiment B wherein
$R^2$ is methyl;
each $R^4$ is independently Br, Cl, F, cyano or methoxy;
each $R^5$ is independently Br, Cl, F, methyl or methoxy; and
$R^6$ is H.

Embodiment D. A compound of Embodiment C wherein
each $R^4$ is independently Br, Cl or F;
each $R^5$ is independently Br, Cl, F or methoxy; and
m and n are each 1 and $R^4$ is at the 4-position (or para position) and $R^5$ is at the 6-position (or ortho position); or m is 1 and $R^4$ is at the 4-position (or para position), and n is 2 and one $R^5$ is at the 4-position (or para position) and the other is at the 6-position (or ortho position); or m is 2 and one $R^4$ is at the 4-position (or para position) and the other is at the 6-position (or ortho position), and n is 1 and $R^5$ is at the 6-position (or ortho position).

Embodiment E. A compound of Embodiment D wherein
$R^4$ is Cl or F;
each $R^5$ is independently Cl, F or methoxy; and
m and n are each 1 and $R^4$ is at the 4-position (or para position) and $R^5$ is at the 6-position (or ortho position); or m is 1 and $R^4$ is at the 4-position (or para position), and n is 2 and one $R^5$ is at the 4-position (or para position) and the other is at the 6-position (or ortho position).

Embodiment F. A compound of Formula 1 wherein
$R^1$ is $C_1$-$C_2$ alkyl;
$R^2$ is cyano, halogen, $C_1$-$C_2$ alkyl or $C_1$-$C_2$ haloalkyl;
$R^3$ is halogen or methyl;
each $R^4$ is independently halogen, cyano, nitro, $C_1$-$C_3$ alkyl, $C_1$-$C_3$ haloalkoxy, $C_2$-$C_6$ alkenyloxy, $C_2$-$C_6$ alkynyloxy, $C_2$-$C_6$ cyanoalkoxy, $C_2$-$C_6$ alkoxyalkyl or $C_2$-$C_6$ alkoxyalkoxy;
each $R^5$ is independently halogen, $C_1$-$C_3$ alkyl, $C_2$-$C_6$ alkoxyalkyl, $C_1$-$C_3$ alkoxy, $C_1$-$C_3$ haloalkoxy, $C_2$-$C_6$ alkenyloxy, $C_2$-$C_6$ alkynyloxy, $C_2$-$C_6$ cyanoalkoxy or $C_2$-$C_6$ alkoxyalkoxy; provided that at least one $R^5$ is selected from halogen;
m and n are each independently 1, 2 or 3;
$R^6$ is H; or $C_1$-$C_3$ alkyl or $C_1$-$C_3$ haloalkyl, each optionally substituted with up to 2 substituents independently selected from $R^{6a}$; or amino, $C_2$-$C_4$ alkenyl, $C_2$-$C_4$ alkynyl, $C_3$-$C_6$ cycloalkyl, $CH(=O)$, $S(=O)_2 OM$, $S(=O)_u R^7$, $(C=W)R^8$ or $OR^9$;

each $R^{6a}$ is independently cyano, $C_3$-$C_6$ cycloalkyl, $C_1$-$C_3$ alkoxy, $C_1$-$C_3$ haloalkoxy, $C_1$-$C_3$ alkylthio, $C_1$-$C_3$ alkylsulfinyl or $C_1$-$C_3$ alkylsulfonyl;

M is K or Na;

u is 0, 1 or 2;

$R^7$ is $C_1$-$C_3$ alkyl or $C_1$-$C_3$ haloalkyl;

W is O or S;

$R^8$ is $C_1$-$C_3$ alkyl, $C_2$-$C_4$ alkoxyalkyl, $C_2$-$C_4$ alkylaminoalkyl, $C_3$-$C_6$ dialkylaminoalkyl, $C_1$-$C_3$ alkoxy, $C_1$-$C_3$ alkylthio or $C_2$-$C_4$ alkylthioalkyl;

$R^9$ is H; or $C_1$-$C_3$ alkyl or C1-$C_3$ haloalkyl, each optionally substituted with up to 2 substituents independently selected from $R^{9a}$; or CH($=$O), $C_3$-$C_6$ cycloalkyl, S($=$O)$_2$OM or (C$=$W)$R^{10}$; and each $R^{9a}$ is independently cyano, $C_3$-$C_6$ cycloalkyl, $C_1$-$C_3$ alkoxy, $C_1$-$C_3$ haloalkoxy, $C_1$-$C_3$ alkylthio, $C_1$-$C_3$ alkylsulfinyl or $C_1$-$C_3$ alkylsulfonyl; and $R^{10}$ is $C_1$-$C_3$ alkyl, $C_2$-$C_4$ alkoxyalkyl, C2-C4 alkylaminoalkyl, $C_3$-$C_6$ dialkylaminoalkyl, $C_1$-$C_3$ alkoxy, $C_1$-$C_3$ alkylthio or $C_2$-$C_4$ alkylthioalkyl;

provided that the compound of Formula 1 is not:
N-(2-bromo-4-fluoro-6-nitrophenyl)-4-(2-chloro-4-fluorophenyl)-1,3-dimethyl-1H-pyrazol-5-amine; or
3-chloro-4-(2-chloro-4-fluorophenyl)-N-(2,4-difluoro-6-nitrophenyl)-1-methyl-1H-pyrazol-5-amine;

Embodiment G. A compound of Embodiment F wherein
$R^1$ is methyl;
$R^2$ is cyano, halogen or $C_1$-$C_2$ alkyl;
$R^3$ is halogen;
each $R^4$ is independently halogen, cyano, methyl, $C_1$-$C_2$ alkoxy or $C_1$-$C_2$ haloalkoxy;
m is 1 and $R^4$ is at the 4-position (or para position); or m is 1 and $R^4$ is at the 6-position (or ortho position); or m is 2 and one $R^4$ is at the 4-position (or para position), and the other is at the 6-position (or ortho position);
each $R^5$ is independently halogen, methyl, methoxy, halomethyl, $C_2$-$C_4$ alkenyloxy or $C_2$-$C_4$ cyanoalkoxy;
n is 1 and $R^5$ is at the 4-position (or para position); or n is 1 and $R^5$ is at the 6-position (or ortho position); or n is 2 and one $R^5$ is at the 4-position (or para position), and the other is at the 6-position (or ortho position); and
$R^6$ is H or methyl.

Embodiment H. A compound of Embodiment G wherein
$R^2$ is methyl;
each $R^4$ is independently Br, Cl, F, cyano or methoxy;
each $R^5$ is independently Br, Cl, F, methyl or methoxy; and
$R^6$ is H.

Embodiment I. A compound of Embodiment H wherein
$R^4$ is Br, Cl or F;
each $R^5$ is independently Br, Cl, F or methoxy; and
m and n are each 1 and $R^4$ is at the 4-position and $R^5$ is at the 6-position; or m is 1 and $R^4$ is at the 4-position, and n is 2 and one $R^5$ is at the 4-position and the other is at the 6-position.

Embodiment J. A compound of Embodiment I wherein
$R^4$ is Cl or F; and
each $R^5$ is independently Cl, F or methoxy.

Specific embodiments include compounds of Formula 1 selected from the group consisting of:

4-(2-bromo-4,6-difluorophenyl)-N-(2-fluoro-6-nitrophenyl)-1,3-dimethyl-1H-pyrazol-5-amine (Compound 1), 3-chloro-4-[5-[(2-chloro-4-fluoro-6-nitrophenyl)amino]-1,3-dimethyl-1H-pyrazol-4-yl]benzonitrile (Compound 18), N-(2-chloro-4-fluoro-6-nitrophenyl)-4-(2-chloro-4-fluorophenyl)-1,3-dimethyl-1H-pyrazol-5-amine (Compound 19), 4-(2-chloro-6-fluorophenyl)-N-(2-fluoro-4-methoxy-6-nitrophenyl)-1,3-dimethyl-1H-pyrazol-5-amine (Compound 23), 4-(2,4-difluorophenyl)-N-(2-fluoro-4-methoxy-6-nitrophenyl)-1,3-dimethyl-1H-pyrazol-5-amine (Compound 57), 4-(2-bromo-4-fluorophenyl)-N-(2-fluoro-6-nitrophenyl)-1,3-dimethyl-1H-pyrazol-5-amine (Compound 60), 4-(2-chloro-4,6-difluorophenyl)-N-(2-fluoro-6-nitrophenyl)-1,3-dimethyl-1H-pyrazol-5-amine (Compound 68), 4-(2-chloro-4-fluorophenyl)-N-(2-fluoro-6-nitrophenyl)-3-ethyl-1-methyl-1H-pyrazol-5-amine (Compound 72), N-(2-chloro-4-fluoro-6-nitrophenyl)-4-(2-chloro-4-methoxyphenyl)-1,3-dimethyl-1H-pyrazol-5-amine (Compound 73), 4-(2-chloro-4-fluorophenyl)-N-(2-fluoro-4-methyl-6-nitrophenyl)-1,3-dimethyl-1H-pyrazol-5-amine (Compound 93), 4-(2-chloro-4-fluorophenyl)-N-(4-fluoro-2-nitrophenyl)-1,3-dimethyl-1H-pyrazol-5-amine (Compound 111), 4-(2-chloro-4-fluorophenyl)-N-(2-fluoro-6-nitrophenyl)-1,3-dimethyl-1H-pyrazol-5-amine (Compound 112), 4-(2,4-difluorophenyl)-N-(2-fluoro-6-nitrophenyl)-1,3-dimethyl-1H-pyrazol-5-amine (Compound 118), N-(4-chloro-2-fluoro-6-nitrophenyl)-4-(2-chloro-4-fluorophenyl)-1,3-dimethyl-1H-pyrazol-5-amine (Compound 121) and 3-chloro-4-[5-[(2-fluoro-4-methyl-6-nitrophenyl)amino]-1,3-dimethyl-1H-pyrazol-4-yl]benzonitrile (Compound 127).

This invention provides a fungicidal composition comprising a compound of Formula 1 (including all stereoisomers, N-oxides, and salts thereof), and at least one other fungicide. Of note as embodiments of such compositions are compositions comprising a compound corresponding to any of the compound embodiments described above.

This invention provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, N-oxides, and salts thereof). Of note as embodiments of such methods are methods comprising applying a fungicidally effective amount of a compound corresponding to any of the compound embodiments describe above. Of particular note are embodiments where the compounds are applied as compositions of this invention.

Of note are compounds of Formula 1 that are compounds of Formula 1A (including all geometric and stereoisomers), N-oxides, hydrates and salts thereof, and agricultural compositions containing them and their use as fungicides:

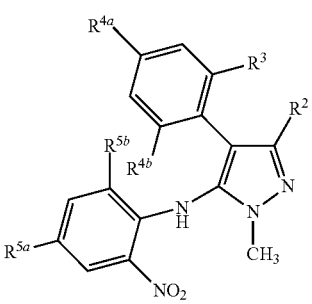

wherein
- $R^2$ is cyano, halogen or $C_1$-$C_2$ alkyl;
- $R^3$ is halogen;
- $R^{4a}$ and $R^{4b}$ are each independently H or halogen, provided that at least one is halogen; and
- $R^{5a}$ and $R^{5b}$ are each independently H, halogen, methyl or methoxy, provided that at least one is halogen;
- provided that when $R^3$ is Cl, $R^{4a}$ is F and $R^{4b}$ is H, then $R^{5a}$ is H, Br, Cl, I, methyl or methoxy.

Embodiment A1. A compound of Formula 1A wherein
- $R^2$ is methyl or ethyl;
- $R^3$ is Br, Cl or F;
- $R^{4a}$ and $R^{4b}$ are each independently H, Br, Cl or F; and
- $R^{5a}$ and $R^{5b}$ are each independently H, Br, Cl, F or methyl.

Embodiment B1. A compound of Embodiment A1 wherein
- $R^2$ is methyl;
- $R^{4a}$ is Cl or F;
- $R^{4b}$ is H, Cl or F; and
- $R^{5a}$ is H, Cl, F or methyl; and
- $R^{5b}$ is H or F.

Also of note is a fungicidal composition comprising a fungicidally effective amount of a compound of Formula 1A (including all geometric and stereoisomers, N-oxides, and salts thereof) or any one of counterpart embodiments that are embodiment counterparts to Embodiments 1 through 95 and Embodiments A through J and at least one additional component selected from the group consisting of surfactants, solid diluents and liquid diluents. Additionally of note is a method for controlling plant diseases caused by fungal plant pathogens comprising applying to the plant or portion thereof, or to the plant seed, a fungicidally effective amount of a compound of Formula 1A (including all geometric and stereoisomers, N-oxides, and salts thereof) or any one of said counterpart embodiments. Of particular note are embodiments where the compounds of Formula 1A are applied as compositions of this invention.

One or more of the following methods and variations as described in Schemes 1-12 can be used to prepare the compounds of Formula 1. The definitions of $R^1$, $R^2$, $R^3$, $R^4$, $R^5$, m, n and $R^6$ in the compounds of Formulae 1-21 below are as defined above in the Summary of the Invention unless otherwise noted. Formulae 1a and 1b are subsets of Formula 1. Substituents for subset formulae are as defined for its parent formula unless otherwise noted.

As shown in Scheme 1, compounds of Formula 1 can be prepared by reaction of 5-aminopyrazoles of Formula 2 with nitrophenyl compounds of Formula 3 wherein $L^1$ is a leaving group such as halogen (e.g., F, Cl, Br, I) or sulfonate (e.g., mesylate, triflate or p-toluenesulfonate), optionally in the presence of a metal catalyst, and generally in the presence of a base such as potassium tert-butoxide, triethylamine or potassium carbonate and a solvent such as tetrahydrofuran, N,N-dimethylformamide, 1,4-dioxane, toluene, ethanol, methanol or dimethyl sulfoxide. In certain instances, the use of a metal catalyst in amounts ranging from catalytic up to superstoichiometric can facilitate the desired reaction. Typical reaction conditions include, for example, running the reaction in the presence of a metal catalyst such as copper salt complexes (e.g., CuI with N,N'-dimethylethylenediamine, proline or bipyridyl), palladium complexes (e.g., tris(dibenzylideneacetone)dipalladium(0)) or palladium salts (e.g., palladium acetate) with ligands such as 4,5-bis(diphenylphosphino)-9,9-dimethylxanthene, 2-dicyclohexylphosphino-2',4',6'-triisopropylbiphenyl or 2,2'-bis-(diphenylphosphino)1,1'-binaphthalene, with a base such as potassium carbonate, cesium carbonate, potassium phosphate, sodium phenoxide or sodium tert-butoxide and a solvent such as N,N-dimethylformamide, 1,2-dimethoxyethane, dimethyl sulfoxide, 1,4-dioxane or toluene, optionally containing an alcohol such as ethanol. For relevant references, see PCT Patent Publications WO 2013/126283, Synthesis Example 1, Step C; and WO 2010/020363, Example 2A. Also, the method of Scheme 1 is illustrated in present Example 1, Step C; Example 5, Step C; and Example 3. Compounds of Formula 3 are commercially available, or their preparation is known in the art.

Scheme 1

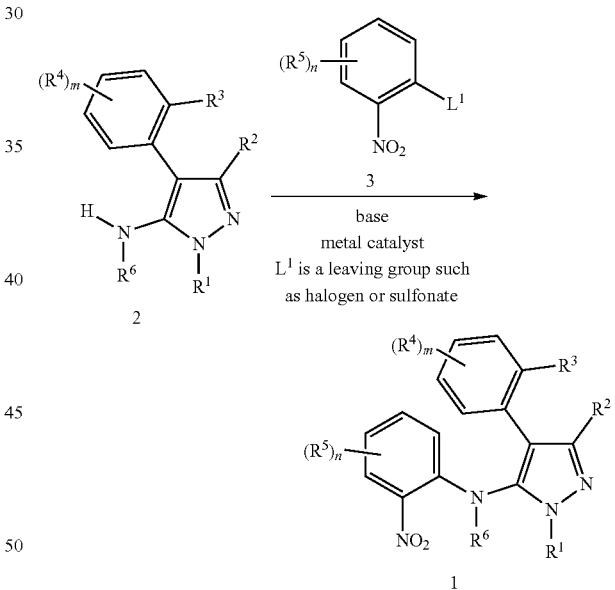

General methods useful for preparing 5-aminopyrazoles of Formula 2 are well-known in the art; see, for example, Journal für Praktische Chemie (Leipzig) 1911, 83, 171 and J. Am. Chem. Soc. 1954, 76, 501. One such method is illustrated in Scheme 2 below, wherein 5-aminopyrazoles of Formula 2 are prepared by condensing compounds of Formula 4 with a hydrazine of Formula 5 (e.g., methylhydrazine or ethylhydrazine) in a solvent such as ethanol or methanol and optionally in the presence of an acid such as acetic acid, according to general procedures known in the art; see, for example, PCT Patent Publication WO 2012/031061 Synthesis Example 1, Step A; and Synthesis Example 2, Step C. Also, the method of Scheme 2 is illustrated in present Example 1, Step B.

Scheme 2

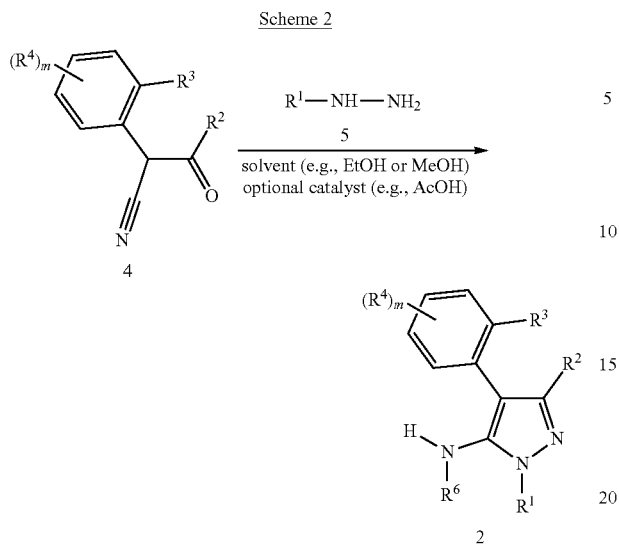

Alternatively, as shown in Scheme 3, 5-aminopyrazoles of Formula 2 can also be prepared by reacting 4-bromo or 4-iodo pyrazoles of Formula 6 with boronic acid compounds of Formula 7 using well-known transition-metal-catalyzed cross-coupling reaction conditions.

Scheme 3

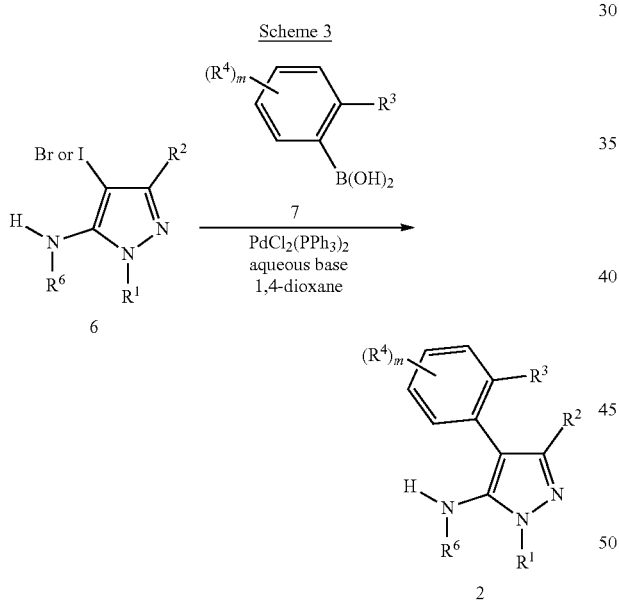

Methods Useful for Preparing Compounds of Formula 6 are Known in the Art.

Compounds of Formula 1a (i.e. Formula 1 wherein $R^6$ is H) can be prepared as shown in Scheme 4. In this method, compounds of Formula 8 are condensed with a hydrazine of Formula 5 (e.g., methylhydrazine or ethylhydrazine) in a solvent such as ethanol or methanol and optionally in the presence of an acid or base catalyst such as acetic acid, piperidine or sodium methoxide, according to general procedures known in the art. For reaction conditions see, PCT Patent Publication WO 2013/116251, Synthesis Example 1, Step C and Example 2, Step B. Also, the method of Scheme 4 using a compound of Formula 8 wherein $R^a$ is methyl is illustrated in Example 2, Step C of the present invention.

Scheme 4

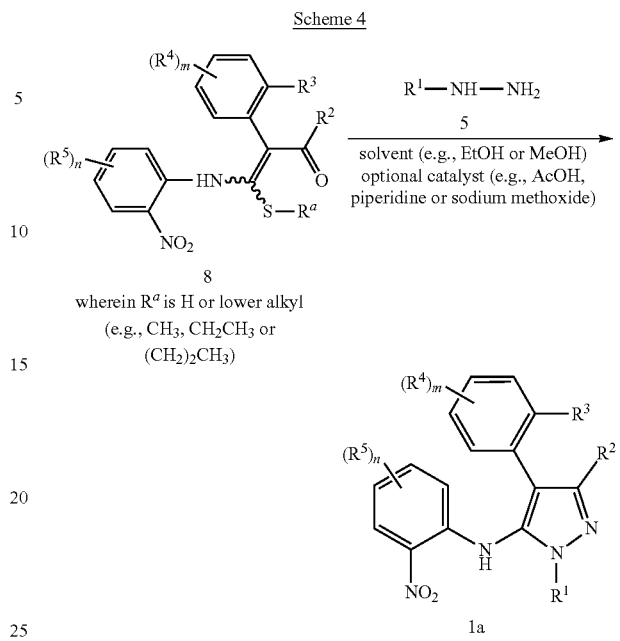

As shown in Scheme 5, compounds of Formula 8 can be prepared by reacting ketene dithioacetal derivatives of Formula 9 with compounds of Formula 10 optionally in the presence of a base, such as sodium hydride or ethylmagnesium chloride, in solvents such as toluene, tetrahydrofuran or dimethoxymethane, at temperatures ranging from about −10° C. to the boiling point of the solvent. For a related reference see, for example, *J. Heterocycl. Chem.* 1975, 12(1), 139. Methods useful for preparing compounds of Formula 9 are known in the art.

Scheme 5

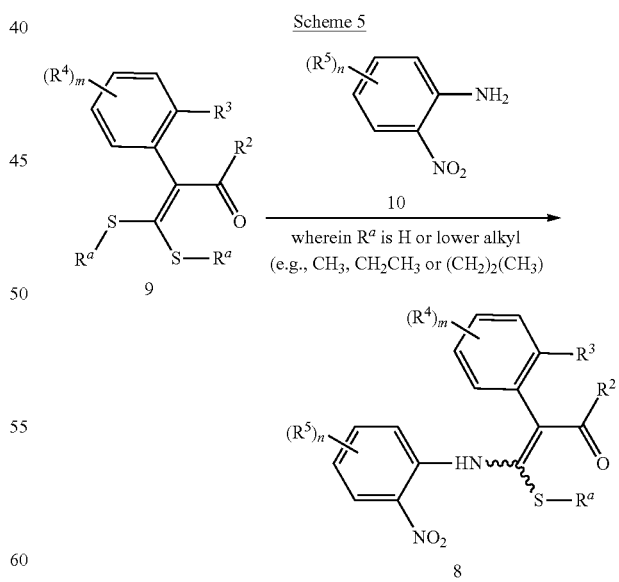

Additionally, as shown in Scheme 6, compounds of Formula 8 wherein $R^a$ is lower alkyl (e.g., methyl, ethyl, n-propyl) and Formula 8a (i.e. tautomer of Formula 8 when $R^a$ is H) can be prepared via a condensation reaction of isothiocyanate compounds of Formula 11 with carbonyl compounds of Formula 12 to give intermediate compounds of Formula 13, which are salts of the thioamides of Formula 8a. The intermediate compounds of Formula 13 can either be used in situ (as is illustrated in WO 2013/116251, Synthesis Example 1, Step C; and present Example 2, Step C) or isolated (as is illustrated in WO 2013/116251, Example 2, Step A). Bases useful for preparing compounds of Formula 13 include hydrides, alkoxides, hydroxides or carbonates of sodium or potassium, such as sodium hydride, potassium tert-butoxide, sodium ethoxide, potassium hydroxide, sodium hydroxide or potassium carbonate. Amine bases (e.g., triethylamine or N,N-diisopropylethylamine) can also be used to effect the condensation of the compounds of Formulae 11 and 12 to Formula 13. A variety of solvents are useful, such as tetrahydrofuran, diethyl ether, toluene, N,N-dimethylformamide, alcohols (e.g., ethanol), esters (e.g., ethyl acetate or isopropyl acetate), or mixtures thereof. Solvents are chosen for compatibility with the base, as is understood by those skilled in the art. Reaction temperatures can range from −78° C. to the boiling point of the solvent. One useful mixture of base and solvent combination is potassium tert-butoxide or potassium tert-pentoxide in tetrahydrofuran, to which can be added a solution of an isothiocyanate of Formula 11 and a carbonyl compound of Formula 12, which are either combined into one solution, or added separately, preferably by addition of the carbonyl compound followed by addition of the isothiocyanate. Typically this reaction is run at −70 to 0° C. The salt of Formula 13 can be acidified to form the ketothioamide compound of Formula 8a or alkylated with $R^aX^1$ (Formula 14) wherein $R^a$ is lower alkyl (e.g., methyl, ethyl, n-propyl) and $X^1$ is a nucleofuge (i.e. a nucleophilic reaction leaving group such as Br, I, $OS(O)_2CH_3$) to form the corresponding compound of Formula 8. This general method is known in the chemical literature; see, for example, *Zhurnal Organicheskoi Khimii* 1982, 18(12), 2501. The method of Scheme 6 to prepare a compound of Formula 8 wherein $R^a$ is methyl from an intermediate compound of Formula 13, which is not isolated, is illustrated in PCT Patent Publication WO 2013/116251 Synthesis Example 1, Step C. Also, present Example 2, Step C illustrates the preparation of a compound of Formula 8.

Scheme 6

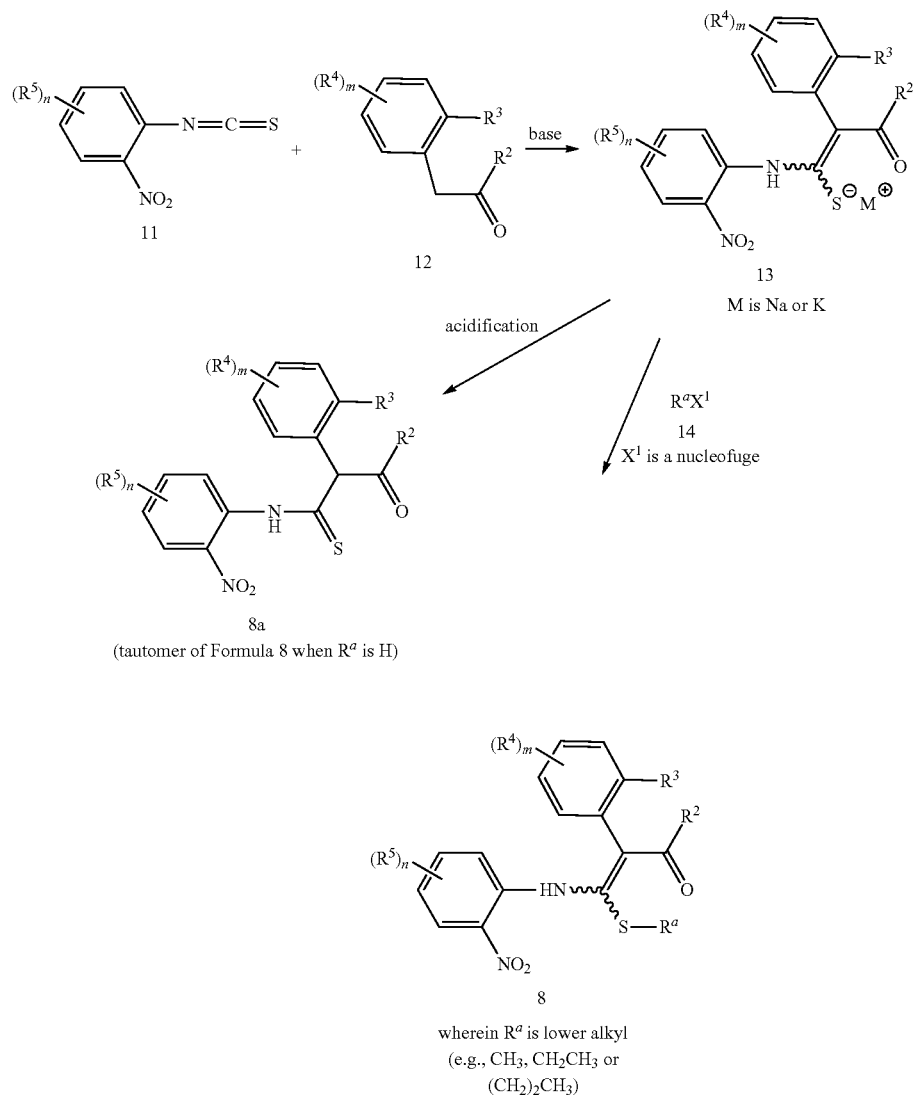

Ketothioamides of Formula 8a can also be prepared by allowing the corresponding ketoamides to react with sulfurizing agents such as Lawesson's reagent or $P_2S_5$; see, for example, *Helv. Chim. Act.* 1998, 81(7), 1207.

As shown in Scheme 7, compounds of Formula 1 can also be prepared by reacting 1H-pyrazole compounds of Formula 15 with methylating agents of formula $R^1$-$L^2$ wherein $R^1$ is methyl or ethyl and $L^2$ is a leaving group such as halogen (e.g., Cl, Br, I), sulfonate (e.g., mesylate, triflate or p-toluenesulfonate) or phosphate (e.g., dimethyl phosphate), preferably in the presence of a base such as 1,8-diazabicyclo[5.4.0]undec-7-ene, potassium carbonate or potassium hydroxide, and a solvent such as N,N-dimethylformamide, tetrahydrofuran, toluene or water. General procedures for methylations of this type are well-known in the art and can be readily adapted to prepare compounds of the present invention. Particularly useful methylating agents include diazomethane and iodomethane using general procedures known in the art, such as those described in *Canada Journal of Chemistry* 1986, 64, 2211-2219 and *Heterocycles* 2000, 53(12), 2775-2780.

(II), bis(triphenylphosphine)dichloronickel(II) and copper(I) salts (e.g., copper(I) iodide, copper(I) bromide, copper(I) chloride, copper(I) cyanide or copper(I) triflate). Optimal conditions will depend on the catalyst used and the counterion attached to the coupling reagent (i.e. $M^1$), as is understood by one skilled in the art. In some cases the addition of a ligand such as a substituted phosphine or a substituted bisphosphinoalkane promotes reactivity. Also, the presence of a base such as an alkali carbonate, tertiary amine or alkali fluoride may be necessary for some reactions involving organoboron reagents of the Formula 17. For reviews of this type of reaction see: E. Negishi, *Handbook of Organopalladium Chemistry for Organic Synthesis*, John Wiley and Sons, Inc., New York, 2002; N. Miyaura, *Cross-Coupling Reactions: A Practical Guide*, Springer, N.Y., 2002; H. C. Brown et al., *Organic Synthesis via Boranes, Vol.* 3, Aldrich Chemical Co., Milwaukee, WI, 2002; Suzuki et al., Chemical Review 1995, 95, 2457-2483 and Molander et al., *Accounts of Chemical Research* 2007, 40, 275-286. Also, the method of Scheme 8 is illustrated PCT Patent Publications WO 2010/101973 and WO 2012/031061.

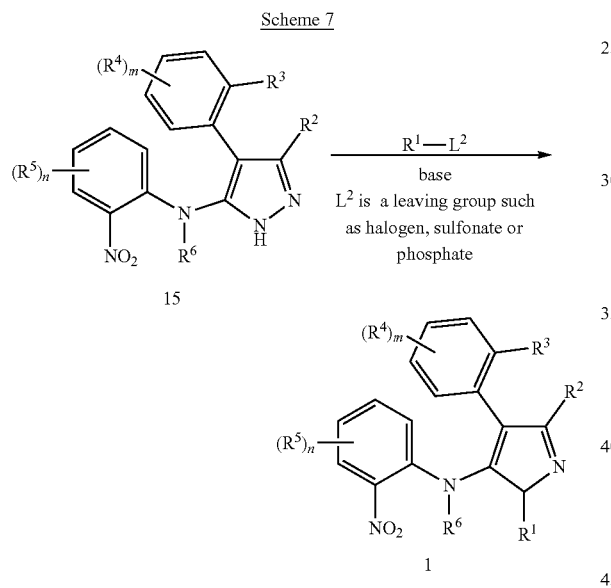

Scheme 7

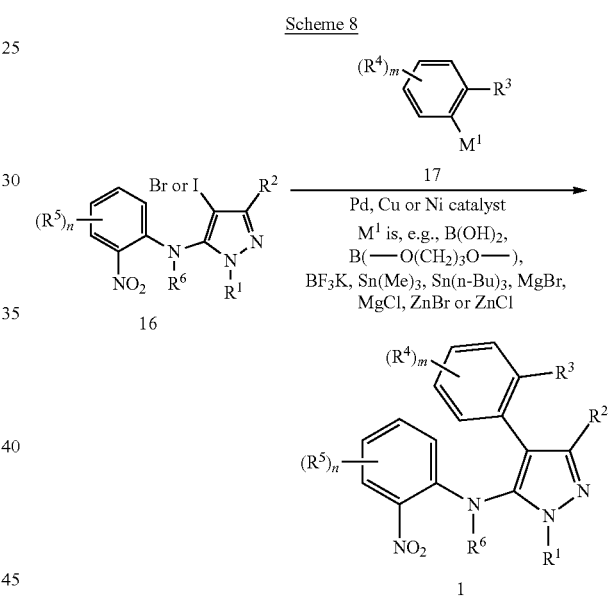

Scheme 8

Compounds of Formula 15 can be prepared by condensing compounds of Formula 8 with hydrazine, in a manner analogous to the method of Scheme 4. This method is described in *Chemistry of Heterocyclic Compounds* 2005, 41(1), 105-110.

In an alternative method, as shown in Scheme 8, compounds of Formula 1 can be prepared by reaction of 4-bromo or 4-iodo pyrazoles of Formula 16 with organometallic compounds of Formula 17 under transition-metal-catalyzed cross-coupling reaction conditions, in the presence of a suitable palladium, copper or nickel catalyst. In this method compounds of Formula 17 are organoboronic acids (e.g., $M^1$ is $B(OH)_2$), organoboronic esters (e.g., $M^1$ is $B(-OC(CH_2)_3 O-)$, organotrifluoroborates (e.g., $M^1$ is $BF_3K$), organotin reagents (e.g., $M^1$ is $Sn(n-Bu)_3$, $Sn(Me)_3$), Grignard reagents (e.g., $M^1$ is MgBr or MgCl) or organozinc reagents (e.g., $M^1$ is ZnBr or ZnCl). Suitable metal catalysts include, but are not limited to: palladium(II) acetate, palladium(II) chloride, tetrakis(triphenylphosphine)-palladium (0), bis(triphenylphosphine)palladium(II) dichloride, dichloro[1,1'-bis(diphenylphosphino)ferrocene]palladium As shown in Scheme 9, pyrazole intermediates of Formula 16 are readily prepared from corresponding pyrazoles of Formula 18 by treatment with a halogenating agent. Suitable halogenating agents for this method include N-bromosuccinimide (NB S), N-iodo-succinimide (NIS), bromine, sodium bromite, thionyl chloride, oxalyl chloride, phenylphosphonic dichloride or phosgene. Particularly useful is N-bromosuccinimide (NBS) and N-iodosuccinimide (NIS). Suitable solvents for this reaction include, for example, N,N-dimethylformamide, N,N-dimethylacetamide, dichloromethane, chloroform, chlorobutane, benzene, xylenes, chlorobenzene, tetrahydrofuran, p-dioxane, acetonitrile, and the like. Optionally, an organic base such as triethylamine, pyridine, N,N-dimethylaniline, and the like can be added. Typical reaction temperatures range from about ambient temperature to 200° C. For representative procedures see *Synthesis* 2006, 17, 2855-2864; *Journal of Medicinal Chemistry* 2005, 48, 6843-6854; *Journal of Medicinal Chemistry* 2007, 50, 3086-3100 and *Journal of Medicinal Chemistry* 2005, 48, 4420-4431.

Scheme 9

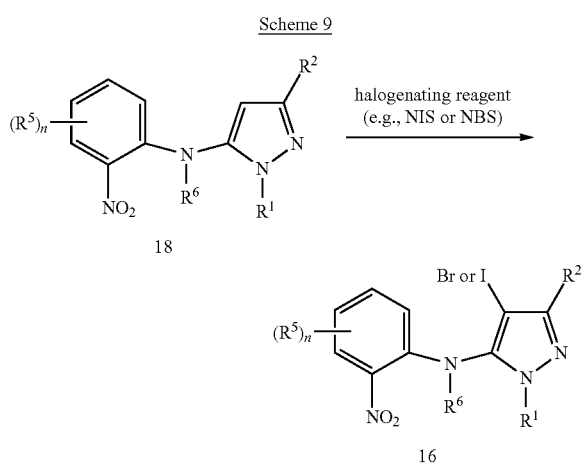

As shown in Scheme 10, compounds of Formula 18 can be prepared from corresponding compounds of Formula 19 by procedures analogous to those used for the method of Scheme 1. Compounds of Formula 19 are commercially available or can be prepared by methods known in the art.

Scheme 10

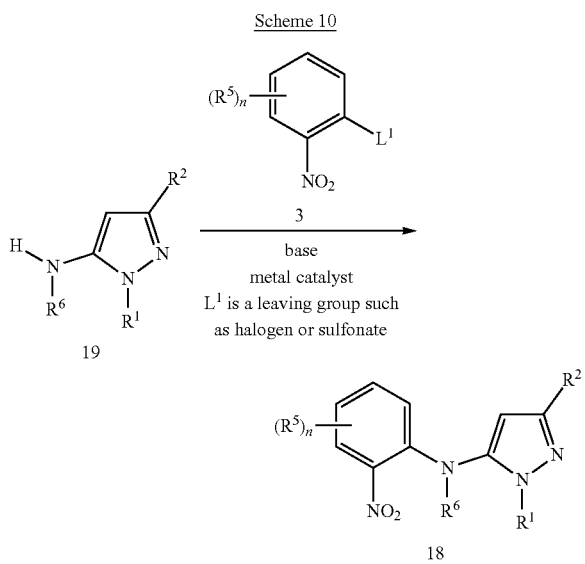

Compounds of Formula 1 and their intermediates described herein can be subjected to various electrophilic, nucleophilic, organometallic, oxidation and reduction reactions to add substituents or modify existing substituents, and thus provide other functionalized compounds of Formula 1. For example, as shown in Scheme 11, compounds of Formula 1b (i.e. Formula 1 wherein $(R^5)_n$ is $CH_3$) can be prepared by reaction of compounds of Formula 20 wherein $L^3$ leaving group such as a halogen (e.g., Br, I) or sulfonate (e.g., mesylate, triflate, p-toluenesulfonate) with reagents such as 2,4,6-trimethylboroxine or tetramethylstannane in the presence of a catalyst such as [1,1'-bis(diphenylphosphino)-ferrocene]palladium(II) chloride dichloromethane adduct, preferably in the presence of a base such as 1,8-diazabicyclo[5.4.0]undec-7-ene, cesium carbonate or potassium hydroxide and in a solvent such as N,N-dimethylformamide, tetrahydrofuran, 1,4-dioxane, ethanol, toluene or water. The method of Scheme 11 is illustrated PCT Patent Publication WO 2013/192126 Example 4, Step A, and in present Example 4, Step B.

Compounds of Formula 20 can be prepared by methods described in PCT Patent Publications WO 2010/101973 and WO 2012/031061. One skilled in the art will recognize that in some instances preparation of N-protected compounds of Formula 20 prior to functional group interconversions will aid in obtaining the desired products. The choice and use of a suitable N-protection group will be apparent to one skilled in the art; for representative examples see T. W. Greene and P. G. M. Wuts, *Protective Groups in Organic Synthesis*, 2nd ed.; Wiley: New York, 1991. Also, Step A of present Example 4 illustrates the preparation of an N-Boc protected compound of Formula 20.

Scheme 11

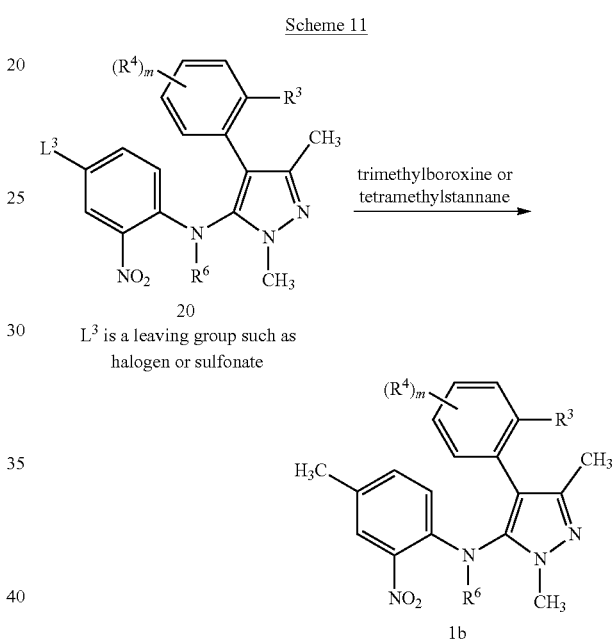

Analogous to the method of Scheme 11, compounds of Formula 20 can be treated with potassium (trifluoromethyl) trimethoxyborate to provide trifluoromethyl analogs of Formula 1b.

In another example, as shown in Scheme 12, compounds of Formula 1 wherein $R^6$ is other than H can be prepared from the corresponding compounds of Formula 1 wherein $R^6$ is H by reaction with an electrophile comprising $R^6$ (i.e. Formula 21). Typically the reaction is done in the presence of a base such as sodium hydride and a polar solvent such as N,N-dimethylformamide. In this context the expression "electrophile comprising $R^6$" means a chemical compound capable of transferring an $R^6$ moiety to a nucleophile (i.e. the nitrogen atom in Formula 1 when $R^6$ is H). Often electrophiles comprising $R^6$ have the formula $R^6X^2$ wherein $X^2$ is a nucleofuge (i.e. leaving group in nucleophilic reactions). Typical nucleofuges include halide (e.g., Br, Cl, I) or sulfonate (e.g., mesylate, triflate, p-toluenesulfonate). However, some electrophiles comprising $R^6$ do not comprise a nucleofuge; an example is sulfur trioxide ($SO_3$), which after deprotonation (such as by a base of the formula $M^+H^-$ wherein $M^+$ is a cation) of the nitrogen atom in Formula 1 when $R^6$ is H, can bond to the nitrogen atom as a $-SO_3M$ substituent.

Scheme 12

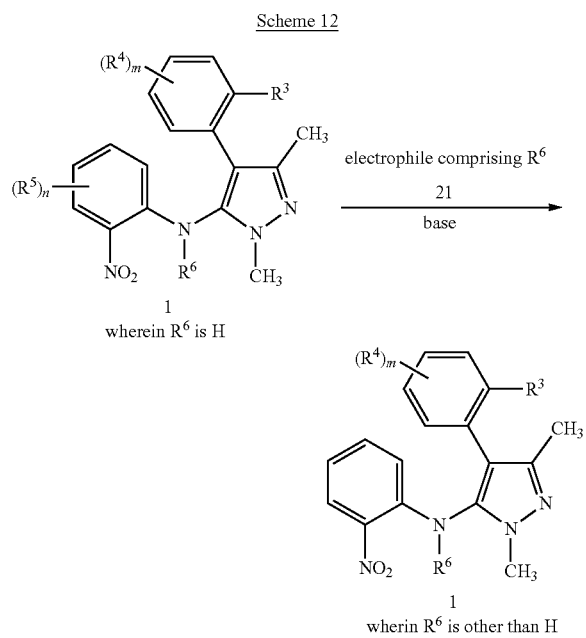

wherein R[6] is H wherin R[6] is other than H

It is recognized that some reagents and reaction conditions described above for preparing compounds of Formula 1 may not be compatible with certain functionalities present in the intermediates. In these instances, the incorporation of protection/deprotection sequences or functional group inter-conversions into the synthesis will aid in obtaining the desired products. The use and choice of the protecting groups will be apparent to one skilled in chemical synthesis (see, for example, T. W. Greene and P. G. M. Wuts, Protective Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing sub stituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "br s" means broad singlet and "dd" means doublet of doublets.

Example 1

Preparation of 4-(2-chloro-4-fluorophenyl)-N-(2-fluoro-6-nitrophenyl)-1,3-dimethyl-1H-pyrazol-5-amine (Compound 112)

Step A: Preparation of α-acetyl-2-chloro-4-fluorobenzeneacetonitrile

A mixture of sodium methoxide solution (30% in methanol, 85 mL, 0.47 mol) in toluene (400 mL) was heated to 120° C. with use of a Dean-Stark trap for the azeotropic removal of methanol. After cooling to 90° C., 2-chloro-4-fluorobenzeneacetonitrile (40.0 g, 0.24 mol) in ethyl acetate (200 mL) was added dropwise to the reaction mixture. The reaction mixture was stirred for 1 h at 90° C., and then hydrochloric acid (1 N, 30 mL) was added. The resulting mixture was extracted with ethyl acetate (3×250 mL) and the combined organic extracts were dried over sodium sulfate, filtered and concentrated under reduced pressure. The resulting material was purified by column chromatography on silica gel (eluting with 3:7 ethyl acetate-petroleum ether) to provide the title compound as a white solid (35 g).
$^1$H NMR (CDCl$_3$): δ 7.49 (dd, 1H), 7.24 (dd, 1H), 7.14-7.09 (m, 1H), 5.13 (s, 1H), 2.36 (s, 3H).

Step B: Preparation of 4-(2-chloro-4-fluorophenyl)-1,3-dimethyl-1H-pyrazol-5-amine To a mixture of α-acetyl-2-chloro-4-fluorobenzeneacetonitrile (i.e. the product of Step A) (28 g, 0.13 mol) in ethanol (400 mL) was added methylhydrazine sulfate (28.6 g, 0.20 mol) and sodium acetate (21.7 g, 0.27 mol). The reaction mixture was heated at 120° C. for 12 h, and then concentrated under reduced pressure to remove the solvent. The resulting mixture was poured into ice-water (500 mL) and filtered collecting a white solid. The solid was rinsed with water and pentane, then dried to provide the title compound as an off-white solid (24 g).
$^1$H NMR (CDCl$_3$): δ 7.45 (dd, 1H), 7.27 (t, 1H), 7.23-7.12 (m, 1H), 4.89 (s, 2H), 3.49 (s, 3H).

Step C: Preparation of 4-(2-chloro-4-fluorophenyl)-N-(2-fluoro-6-nitrophenyl)-1,3-dimethyl-1H-pyrazol-5-amine To a mixture of 4-(2-chloro-4-fluorophenyl)-1,3-dimethyl-1H-pyrazol-5-amine (i.e. the product of Step B) (1.2 g, 5.0 mmol) in tetrahydrofuran (40 mL) at 0° C. was added potassium tert-butoxide (1 M in THF, 10 mL, 10 mmol) portion-wise. The reaction mixture was stirred for 1 h at 0° C., and then 1,2-difluoro-3-nitrobenzene (0.85 g, 5.3 mmol) was added drop-wise. After 30 minutes at 0° C., saturated aqueous ammonium chloride was added to the reaction mixture and the resulting mixture was extracted with ethyl acetate (100 mL). The aqueous layer was further extracted with ethyl acetate (2×40 mL) and the combined organic extracts were washed with saturated sodium chloride solution, dried over sodium sulfate, filtered, and concentrated under reduced pressure. The resulting material was purified by column chromatography on silica gel (eluting with 40% ethyl acetate in petroleum ether) to provide the title compound, a compound of the present invention, as a yellow solid (1.1 g).

$^1$H NMR (CDCl$_3$): δ 8.59 (s, 1H), 7.59 (d, 1H), 7.31 (d, 1H), 7.2 (d, 1H), 7.09 (t, 1H), 7.04-7.01 (m, 1H), 6.82-6.86 (m, 1H), 3.74 (s, 3H), 1.97 (s, 3H).

Example 2

Preparation of 3-chloro-4-[5-[(2-fluoro-6-nitrophenyl)amino]-1,3-dimethyl-1H-pyrazol-4-yl]benzonitrile (Compound 113)

Step A: Preparation of 3-chloro-4-(2-oxopropyl)benzonitrile

To a mixture of 4-amino-3-chlorobenzonitrile (50.0 g, 0.33 mol) in diethyl ether (500 mL) at −10° C. was added boron trifluoride diethyl etherate (61 mL, 0.50 mol). The reaction mixture was stirred at −10° C. for 10 minutes, and then tert-butylnitrite (48 mL, 0.4 mol) was added. After 20 minutes at −10° C., the reaction mixture was allowed to warm to room temperature, stirred for 2 h, and then filtered collecting a white solid. The white solid was triturated with diethyl ether and pentane (1:1, 300 mL), filtered and dried to provide the intermediate compound 2-chloro-4-cyanobenzene diazonium tetrafluoroborate salt as an off-white solid (72 g).

To a mixture of 2-chloro-4-cyanobenzene diazonium tetrafluoroborate salt (72 g, 0.33 mol) in dimethylformamide (500 mL) at −10° C. was added isopropenyl acetate (354 mL, 3.2 mol). The reaction mixture was stirred for 20 minutes at −10° C., and then 4-aminomorpholine (1.0 mL) in dimethyl sulfoxide (40 mL) was added. After 1 h, ice-cold water (1000 mL) was added and the resulting mixture was extracted with ethyl acetate (3×250 mL). The combined organic extracts were dried over sodium sulfate, filtered and concentrated under reduced pressure. The resulting material was purified by column chromatography on silica gel (eluting with 1:4 ethyl acetate-petroleum ether) to provide the title compound as a solid (52 g).

$^1$H NMR (CDCl$_3$): δ 7.69 (s, 1H), 7.53 (d, 1H), 7.32 (d, 1H), 3.93 (s, 2H), 2.28 (s, 3H).

Step B: Preparation of 1-fluoro-2-isothiocyanato-3-nitrobenzene

To a mixture of 2-fluoro-6-nitrobenzenamine (1.0 g, 6.4 mmol) in 1,2-dichlorobenzene (10 mL) at 0° C. was added 2 drops of dimethylformamide followed by thiophosgene (1.46 mL, 19 mmol). The reaction mixture was heated at 160° C. for 1 h, cooled to room temperature and concentrated under reduced pressure. The resulting material was purified by column chromatography on silica gel (eluting with 1:9 ethyl acetate-petroleum ether) to provide the title compound as an oil (0.91 g).

$^1$H NMR (CDCl$_3$) δ 7.88 (d, 1H), 7.46 (t, 1H), 7.36 (m, 1H).

Step C: Preparation of 3-chloro-4-[5-[(2-fluoro-6-nitrophenyl)amino]-1,3-dimethyl-1H-pyrazol-4-yl]benzonitrile To a mixture of 3-chloro-4-(2-oxopropyl)benzonitrile (i.e. the product of Step A) (1.0 g, 5.2 mmol) in tetrahydrofuran (20 mL) at −10° C. was added potassium tert-butoxide (0.7 g, 6.2 mmol). After 30 minutes at −10° C., 1-fluoro-2-isothiocyanato-3-nitrobenzene (i.e. the product of Step B) (0.99 g, 5.0 mmol) in tetrahydrofuran (10 mL) was added to the reaction mixture and stirring was continued for about 15 minutes to provide a reaction mixture containing the intermediate compound 4-[1-[[(2-chloro-6-nitrophenyl)amino]mercaptomethylene]-2-oxopropyl]-3-chlorobenzonitrile potassium salt, which is the potassium salt of α-acetyl-N-(2-chloro-6-nitrophenyl)-2-chloro-4-cyano-benzeneethanethioamide. Iodomethane (1.2 mL, 19 mmol) was added to the reaction mixture. After 20 minutes at −10° C., the reaction temperature was brought to 0° C., and acetic acid (5.0 mL) and methylhydrazine (85% in water, 0.5 g, 10 mmol) were added. The reaction mixture was allowed to warm to room temperature, heated at reflux for 2 h, and then poured into ice-cold water (30 mL) and ethyl acetate (20 mL). The organic layer was separated, and the aqueous layer was extracted with ethyl acetate (2×10 mL). The combined organic extracts were washed with saturated sodium chloride solution (20 mL), dried over sodium sulfate, filtered and concentrated under reduced pressure. The resulting material was purified by column chromatography on silica gel (eluting with 2:3 ethyl acetate-petroleum ether) to provide the title compound, a compound of the present invention, as a pale-yellow solid (0.850 g).

$^1$H NMR (CDCl$_3$) δ 8.71 (d, 1H), 7.85 (d, 1H), 7.64-7.58 (m, 2H), 7.34-7.25 (m, 2H), 6.87-6.81 (m, 1H), 3.75 (s, 3H), 1.99 (s, 3H).

Example 3

Preparation of N-(4-bromo-2-fluoro-6-nitrophenyl)-4-(2-chloro-4-fluorophenyl)-1,3-dimethyl-1H-pyrazol-5-amine (Compound 61)

To a mixture of 4-(2-chloro-4-fluorophenyl)-1,3-dimethyl-1H-pyrazol-5-amine (i.e. the product of Example 1, Step B) (0.5 g, 2.1 mmol) in tetrahydrofuran (30 mL) at 0° C. was added potassium tert-butoxide (1 M in THF, 4.2 mL, 4.2 mmol) portion-wise. The reaction mixture was stirred for 1 h at 0° C., and then 5-bromo-1,2-difluoro-3-nitrobenzene (0.54 g, 2.3 mmol) was added drop-wise. After 30 minutes at 0° C., saturated aqueous ammonium chloride was added to the reaction mixture and the resulting mixture was extracted with ethyl acetate (100 mL). The aqueous layer was further extracted with ethyl acetate (2×40 mL) and the combined organic extracts were washed with saturated sodium chloride solution, dried over sodium sulfate, filtered, and concentrated under reduced pressure. The resulting material was purified by column chromatography on silica gel (eluting with 40% ethyl acetate in petroleum ether) to provide the title compound, a compound of the present invention, as a yellow solid (0.45 g).

$^1$H NMR (CDCl$_3$): δ 8.69 (br s, 1H), 7.77 (t, 1H), 7.66 (dd, 1H), 7.27 (dd, 2.0 Hz, 1H), 7.09-7.06 (m, 2H), 3.73 (s, 3H), 1.97 (s, 3H).

Example 4

Preparation of 4-(2-chloro-4-fluorophenyl)-N-(2-fluoro-4-methyl-6-nitrophenyl)-1,3-dimethyl-1H-pyrazol-5-amine (Compound 93)

Step A: Preparation of 1,1-Dimethylethyl N-(4-bromo-2-fluoro-6-nitrophenyl)-N-[4-(2-chloro-4-fluorophenyl)-1,3-dimethyl-1H-pyrazol-5-yl]carbamate To a mixture of N-(4-bromo-2-fluoro-6-nitrophenyl)-4-(2-chloro-4-fluorophenyl)-1,3-dimethyl-1H-pyrazol-5-amine (i.e. the product of Example 3) (1 g, 2.2 mmol) and triethylamine (1.24 mL, 8.9 mmol) in dichloromethane (20 mL) at 0° C. was added di-tert-butyl dicarbonate (1.46 g, 6.7 mmol). The reaction mixture was allowed to warm to room temperature and stirred overnight, and then diluted with water (20 mL) and extracted with dichloromethane (2×20 mL). The combined organic extracts were washed with a saturated sodium chloride solution, dried over sodium sulfate, filtered and concentrated under reduced pressure. The resulting material was purified by column chromatography on silica gel (eluting with 40% ethyl acetate in petroleum ether) to provide the title compound as a yellow solid (750 mg).

$^1$H NMR (CDCl$_3$): δ 7.85 (s, 1H), 7.78 (s, 1H), 7.52-7.47 (m, 1H), 7.17-7.19 (m, 1H), 6.97-6.88 (m, 1H), 3.8 (s, 3H), 1.96 (s, 3H), 1.49 (s, 9H).

Step B: Preparation of 4-(2-chloro-4-fluorophenyl)-
N-(2-fluoro-4-methyl-6-nitrophenyl)-1,3-dimethyl-
1H-pyrazol-5-amine A mixture of 1,1-dimethylethyl N-(4-bromo-2-fluoro-6-nitrophenyl)-N-[4-(2-chloro-4-fluorophenyl)-1,3-dimethyl-1H-pyrazol-5-yl]carbamate (i.e. the product of Step A) (600 mg, 1.07 mmol), potassium carbonate (372 mg, 2.7 mmol), dichloro[1,1'-bis(diphenyl-phosphino)ferrocene]palladium (II) dichloromethane complex (1:1) (40 mg, 0.05 mmol) and trimethylboroxine (0.54 mL, 3.9 mmol) in 1,4-dioxane (20 mL) was heated at reflux for 3 h. The reaction mixture was diluted with water (15 mL) and extracted with ethyl acetate (2×10 mL). The combined organic extracts were washed with saturated aqueous sodium chloride solution (3×5 mL), dried over sodium sulfate, filtered and concentrated under reduced pressure. The resulting material was dissolved in dichloromethane and trifluoroacetic acid (3:1; 4 mL) and stirred at room temperature for 16 h. The reaction mixture was concentrated under reduced pressure and the resulting material was dissolved in dichloromethane (5 mL) and washed with a saturated aqueous sodium bicarbonate solution (2 mL). The aqueous layer was further extracted with dichloromethane (3×10 mL). The combined organic extracts were washed with a saturated sodium chloride solution, dried over sodium sulfate, filtered and concentrated under reduced pressure. The resulting material was purified by column chromatography on silica gel (eluting with 40% ethyl acetate in petroleum ether) to provide the title compound, a compound of the present invention, as a yellow solid (210 mg).

$^1$H NMR (CDCl$_3$) δ 8.41 (s, 1H), 7.45 (s, 1H), 7.24-7.15 (m, 2H), 7.1-7.01 (m, 2H), 3.72 (s, 3H), 2.15 (s, 3H), 1.95 (s, 3H).

Example 5

Alternative Preparation of 3-chloro-4-[5-[(2-fluoro-6-nitrophenyl)amino]-1,3-dimethyl-1H-pyrazol-4-yl]benzonitrile (Compound 113)

Step A: Preparation of
1-methyl-hydrazinecarbonitrile

A solution of cyanogen bromide (13.5 g, 127.5 mmol) and dichloromethane (250 mL) was cooled to 0° C., and then a mixture of methyl hydrazine (85% aqueous solution, 6.0 g, 127.5 mmol), sodium carbonate (7.5 g, 63.9 mmol) and water (60 mL) was added dropwise with vigorous stirring. After visible signs of gas evolution stopped, the aqueous layer was separated and extracted with dichloromethane (3×). The combined organic layers were dried over magnesium sulphate, filtered and the filtrate was concentrated under reduced pressure to provide the title compound as an oil (6.0 g).

Step B: Preparation of 4-(5-amino-1,3-dimethyl-
1H-pyrazol-4-yl)-3-chlorobenzonitrile A mixture of 3-chloro-4-(2-oxopropyl)benzonitrile (13.7 g, 71.4 mmol) and 1-methylhydrazinecarbonitrile (i.e. the product of Step A) (6.0 g, 86 mmol) was heated at 60° C. with stirring. After 48 h, the reaction mixture was dissolved in dichloromethane (100 mL) and water (100 mL), the layers ware separated and the aqueous layer was extracted with dichloromethane (3×). The combined organic layers were dried over magnesium sulphate, filtered and the filtrate was concentrated under reduced pressure. The resulting material was purified by column chromatography on silica gel (eluting with 60% ethyl acetate in petroleum ether) to provide the title compound as a light-yellow solid (8.1 g).

LCMS: 247 (M+1)

Step C: Preparation of 3-chloro-4-[5-[(2-fluoro-6-
nitrophenyl)amino]-1,3-dimethyl-1H-pyrazol-4-yl]
benzonitrile To a mixture of 4-(5-amino-1,3-dimethyl-1H-pyrazol-4-yl)-3-chlorobenzonitrile (i.e. the product of Step B) (1.2 g, 4.8 mol) in tetrahydrofuran (40 mL) at 0° C. was added potassium tert-butoxide (9.7 mL, 1 M in tetrahydrofuran) dropwise. The reaction mixture was stirred at 0° C. for 1 h, and then 1,2-difluoro-3-nitrobenzene (0.85 g, 5.3 mmol) was added dropwise and stirring was continued for an additional 30 minutes at 0° C. The reaction mixture was diluted with saturated aqueous ammonium chloride and ethyl acetate (100 mL), and the layers were separated. The aqueous layer was extracted with ethyl acetate (40 mL×2), and the combined organic extracts were washed with saturated aqueous sodium chloride solution, dried over magnesium sulphate, filtered and the filtrate was concentrated under reduced pressure. The resulting material was purified by column chromatography on silica gel (eluting with 40% ethyl acetate in petroleum ether) to provide a yellow solid. The yellow sold was crystallized from ethanol to provide the title compound, a compound of the present invention, as a light-yellow solid (560 mg).

$^1$H NMR (CDCl$_3$) δ 8.71 (d, 1H), 7.85 (d, 1H), 7.63-7.58 (m, 2H), 7.33-7.25 (m, 2H), 6.86-6.82 (m, 1H), 3.75 (s, 3H), 1.99 (s, 3H).

LCMS: 386 (M+1).

By the procedures described herein together with methods known in the art, the compounds disclosed in the Tables that follow can be prepared. The following abbreviations are used in the Tables which follow: Me means methyl, MeO means methoxy, EtO means ethoxy, and CN means cyano.

TABLE 1

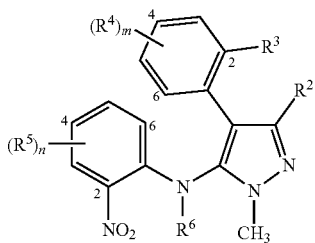

$R^2$ is $CH_3$, $R^3$ is Cl and $(R^4)_m$ is 4-F.

| $(R^5)_n$ |
|---|
| 6-F |
| 4,6-di-F |
| 4-Cl, 6-F |
| 4-Br, 6-F |
| 4-I, 6-F |
| 4-Me, 6-F |
| 4-MeO, 6-F |
| 4-EtO, 6-F |
| 6-Cl |
| 4,6-di-Cl |
| 4-F, 6-Cl |
| 4-Br, 6-Cl |
| 4-I, 6-Cl |
| 4-Me, 6-Cl |
| 4-MeO, 6-Cl |
| 4-EtO, 6-Cl |
| 6-Br |
| 4,6-di-Br |
| 4-F, 6-Br |
| 4-Cl, 6-Br |
| 4-I, 6-Br |
| 4-Me, 6-Br |
| 4-MeO, 6-Br |
| 4-EtO, 6-Br |
| 6-I |
| 4,6-di-I |
| 4-F, 6-I |
| 4-Cl, 6-I |
| 4-Br, 6-I |
| 4-Me, 6-I |
| 4-MeO, 6-I |
| 4-EtO, 6-I |
| 4-Me |
| 4-MeO |
| 4-EtO |
| 6-Me |
| 6-MeO |
| 6-EtO |

The present disclosure also includes Tables 1A through 46A, each of which is constructed the same as Table 1 above, except that the row heading in Table 1 (i.e. "$R^2$ is $CH_3$, $R^3$ is Cl and $(R^4)_m$ is 4-F" is replaced with the respective row headings shown below.

| Table | Row Heading |
|---|---|
| 1A | $R^2$ is $CH_3$, $R^3$ is F and $(R^4)_m$ is 4-F. |
| 2A | $R^2$ is $CH_3$, $R^3$ is Br and $(R^4)_m$ is 4-F. |
| 3A | $R^2$ is $CH_3$, $R^3$ is Me and $(R^4)_m$ is 4-F. |
| 4A | $R^2$ is $CH_3$, $R^3$ is Cl and $(R^4)_m$ is 4-MeO. |
| 5A | $R^2$ is $CH_3$, $R^3$ is F and $(R^4)_m$ is 4-MeO. |
| 6A | $R^2$ is $CH_3$, $R^3$ is Br and $(R^4)_m$ is 4-MeO. |
| 7A | $R^2$ is $CH_3$, $R^3$ is Me and $(R^4)_m$ is 4-MeO. |
| 8A | $R^2$ is $CH_3$, $R^3$ is Cl and $(R^4)_m$ is 4-CN. |
| 9A | $R^2$ is $CH_3$, $R^3$ is F and $(R^4)_m$ is 4-CN. |
| 10A | $R^2$ is $CH_3$, $R^3$ is Br and $(R^4)_m$ is 4-CN. |
| 11A | $R^2$ is $CH_3$, $R^3$ is Me and $(R^4)_m$ is 4-CN. |
| 12A | $R^2$ is $CH_3$, $R^3$ is Cl and $(R^4)_m$ is 4,6-di-F. |
| 13A | $R^2$ is $CH_3$, $R^3$ is F and $(R^4)_m$ is 4,6-di-F. |
| 14A | $R^2$ is $CH_3$, $R^3$ is Br and $(R^4)_m$ is 4,6-di-F. |
| 15A | $R^2$ is $CH_3$, $R^3$ is Me and $(R^4)_m$ is 4,6-di-F. |
| 16A | $R^2$ is $CH_3$, $R^3$ is Cl and $(R^4)_m$ is 4-Cl, 6-F. |
| 17A | $R^2$ is $CH_3$, $R^3$ is F and $(R^4)_m$ is 4-Cl, 6-F. |
| 18A | $R^2$ is $CH_3$, $R^3$ is Br and $(R^4)_m$ is 4-Cl, 6-F. |
| 19A | $R^2$ is $CH_3$, $R^3$ is Me and $(R^4)_m$ is 4-Cl, 6-F. |
| 20A | $R^2$ is $CH_3$, $R^3$ is Cl and $(R^4)_m$ is 4-MeO, 6-F. |
| 21A | $R^2$ is $CH_3$, $R^3$ is F and $(R^4)_m$ is 4-MeO, 6-F. |
| 22A | $R^2$ is $CH_3$, $R^3$ is Br and $(R^4)_m$ is 4-MeO, 6-F. |
| 23A | $R^2$ is $CH_3$, $R^3$ is Me and $(R^4)_m$ is 4-MeO, 6-F. |
| 24A | $R^2$ is Et, $R^3$ is F and $(R^4)_m$ is 4-F. |
| 25A | $R^2$ is Et, $R^3$ is Br and $(R^4)_m$ is 4-F. |
| 26A | $R^2$ is Et, $R^3$ is Me and $(R^4)_m$ is 4-F. |
| 27A | $R^2$ is Et, $R^3$ is Cl and $(R^4)_m$ is 4-MeO. |
| 28A | $R^2$ is Et, $R^3$ is F and $(R^4)_m$ is 4-MeO. |
| 29A | $R^2$ is Et, $R^3$ is Br and $(R^4)_m$ is 4-MeO. |
| 30A | $R^2$ is Et, $R^3$ is Me and $(R^4)_m$ is 4-MeO. |
| 31A | $R^2$ is Et, $R^3$ is Cl and $(R^4)_m$ is 4-CN. |
| 32A | $R^2$ is Et, $R^3$ is F and $(R^4)_m$ is 4-CN. |
| 33A | $R^2$ is Et, $R^3$ is Br and $(R^4)_m$ is 4-CN |
| 34A | $R^2$ is Et, $R^3$ is Me and $(R^4)_m$ is 4-CN. |
| 35A | $R^2$ is Et, $R^3$ is Cl and $(R^4)_m$ is 4,6-di-F. |
| 36A | $R^2$ is Et, $R^3$ is F and $(R^4)_m$ is 4,6-di-F. |
| 37A | $R^2$ is Et, $R^3$ is Br and $(R^4)_m$ is 4,6-di-F. |
| 38A | $R^2$ is Et, $R^3$ is Me and $(R^4)_m$ is 4,6-di-F. |
| 39A | $R^2$ is Et, $R^3$ is Cl and $(R^4)_m$ is 4-Cl, 6-F. |
| 40A | $R^2$ is Et, $R^3$ is F and $(R^4)_m$ is 4-Cl, 6-F. |
| 41A | $R^2$ is Et, $R^3$ is Br and $(R^4)_m$ is 4-Cl, 6-F. |
| 42A | $R^2$ is Et, $R^3$ is Me and $(R^4)_m$ is 4-Cl, 6-F. |
| 43A | $R^2$ is Et, $R^3$ is Cl and $(R^4)_m$ is 4-MeO, 6-F. |
| 44A | $R^2$ is Et, $R^3$ is F and $(R^4)_m$ is 4-MeO, 6-F. |
| 45A | $R^2$ is Et, $R^3$ is Br and $(R^4)_m$ is 4-MeO, 6-F. |
| 46A | $R^2$ is Et, $R^3$ is Me and $(R^4)_m$ is 4-MeO, 6-F. |

TABLE 2

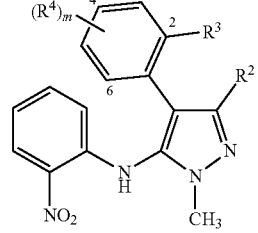

| $R^2$ is $CH_3$ and $R^3$ is Cl. $(R^4)_m$ | $R^2$ is $CH_3$, $R^3$ in Cl and $(R^4)_m$ is 4-F. $(R^4)_m$ |
|---|---|
| 6-F | 4-I, 6-Br |
| 4,6-di-F | 4-Me, 6-Br |
| 4-Cl, 6-F | 4-MeO, 6-Br |
| 4-Br, 6-F | 4-EtO, 6-Br |
| 4-I, 6-F | 4-CN, 6-Br |
| 4-Me, 6-F | 6-I |
| 4-MeO, 6-F | 4,6-di-I |
| 4-EtO, 6-F | 4-F, 6-I |
| 4-CN, 6-F | 4-Cl, 6-I |
| 6-Cl | 4-Br, 6-I |
| 4,6-di-Cl | 4-Me, 6-I |
| 4-F, 6-Cl | 4-MeO, 6-I |
| 4-Br, 6-Cl | 4-EtO, 6-I |
| 4-I, 6-Cl | 4-CN, 6-I |
| 4-Me, 6-Cl | 4-Me |
| 4-MeO, 6-Cl | 4-MeO |
| 4-EtO, 6-Cl | 4-EtO |
| 4-CN, 6-Cl | 4-CN |
| 6-Br | 6-Me |
| 4,6-di-Br | 6-MeO |
| 4-F, 6-Br | 6-EtO |
| 4-Cl, 6-Br | 6-CN |

Formulation/Utility

A compound of Formula 1 of this invention (including N-oxides, hydrates, and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, New Jersey.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents")

generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyl peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Pro-lzed® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pp 8-57 and following, and WO 91/13546. Pellets can be prepared as described in U.S. Pat. No. 4,172,714. Water-dispersible and water-soluble granules can be prepared as taught in U.S. Pat. No. 4,144,050, 3,920,442 and DE 3,246, 493. Tablets can be prepared as taught in U.S. Pat. No. 5,180,587, 5,232,701 and 5,208,030. Films can be prepared as taught in GB 2,095,558 and U.S. Pat. No. 3,299,566.

One embodiment of the present invention relates to a method for controlling fungal pathogens, comprising diluting the fungicidal composition of the present invention (a compound of Formula 1 formulated with surfactants, solid diluents and liquid diluents or a formulated mixture of a compound of Formula 1 and at least one other fungicide)

with water, and optionally adding an adjuvant to form a diluted composition, and contacting the fungal pathogen or its environment with an effective amount of said diluted composition.

Although a spray composition formed by diluting with water a sufficient concentration of the present fungicidal composition can provide sufficient efficacy for controlling fungal pathogens, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be anionic or nonionic surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

The amount of adjuvants added to spray mixtures is generally in the range of about 2.5% to 0.1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

One method of seed treatment is by spraying or dusting the seed with a compound of the invention (i.e. as a formulated composition) before sowing the seeds. Compositions formulated for seed treatment generally comprise a film former or adhesive agent. Therefore, typically a seed coating composition of the present invention comprises a biologically effective amount of a compound of Formula 1 and a film former or adhesive agent. Seeds can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever.

Example A

High Strength Concentrate

| | |
|---|---|
| Compound 60 | 98.5% |
| silica aerogel | 0.5% |
| synthetic amorphous fine silica | 1.0% |

Example B

Wettable Powder

| | |
|---|---|
| Compound 68 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 72 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 93 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 112 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 118 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| Compound 60 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

Fertilizer Stick

| | |
|---|---|
| Compound 68 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

Suspension Concentrate

| | |
|---|---|
| Compound 72 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

Emulsion in Water

| | |
|---|---|
| Compound 93 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

Oil Dispersion

| | |
|---|---|
| Compound 112 | 25% |
| polyoxyethylene sorbitol hexaoleate | 15% |
| organically modified bentonite clay | 2.5% |
| fatty acid methyl ester | 57.5% |

Example L

Suspoemulsion

| | |
|---|---|
| Compound 118 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Water-soluble and water-dispersible formulations are typically diluted with water to form aqueous compositions before application. Aqueous compositions for direct applications to the plant or portion thereof (e.g., spray tank compositions) typically contain at least about 1 ppm or more (e.g., from 1 ppm to 100 ppm) of the compound(s) of this invention.

Seed is normally treated at a rate of from about 0.001 g (more typically about 0.1 g) to about 10 g per kilogram of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Ascomycota, Basidiomycota, Zygomycota phyla, and the fungal-like Oomycata class. They are effective in controlling a broad spectrum of plant diseases, particularly foliar pathogens of ornamental, turf, vegetable, field, cereal, and fruit crops. These pathogens include but are not limited to those listed in Table 1-1. For Ascomycetes and Basidiomycetes, names for both the sexual/teleomorph/perfect stage as well as names for the asexual/anamorph/imperfect stage (in parentheses) are listed where known. Synonymous names for pathogens are indicated by an equal sign. For example, the sexual/teleomorph/perfect stage name Phaeosphaeria nodorum is followed by the corresponding asexual/anamorph/imperfect stage name *Stagnospora nodorum* and the synonymous older name *Septoria nodorum*.

TABLE 1-1

Ascomycetes in the order Pleosporales including *Alternaria solani, A. alternata* and *A. brassicae, Guignardia bidwellii, Venturia inaequalis, Pyrenophora tritici-repentis (Dreschlera tritici-repentis = Helminthosporium tritici-repentis)* and *Pyrenophora teres (Dreschlera teres = Helminthosporium teres), Corynespora cassiicola, Phaeosphaeria nodorum (Stagonospora nodorum = Septoria nodorum), Cochliobolus carbonum* and *C. heterostrophus, Leptosphaeria biglobosa* and *L. maculans*;
Ascomycetes in the order Mycosphaerellales including *Mycosphaerella graminicola (Zymoseptoria tritici = Septoria tritici), M. berkeleyi (Cercosporidium personatum), M. arachidis (Cercospora arachidicola), Passalora sojina (Cercospora sojina), Cercospora zeae-maydis* and *C. beticola*;
Ascomycetes in the order Erysiphales (the powdery mildews) such as *Blumeria graminis* f. sp. *tritici* and *Blumeria graminis* f. sp. *hordei, Erysiphe polygoni, E. necator (=Uncinula necator), Podosphaera fuliginea (=Sphaerotheca fuliginea),* and *Podosphaera leucotricha (=Sphaerotheca fuliginea)*;
Ascomycetes in the order Helotiales such as *Botryotinia fuckeliana (Botrytis cinerea), Oculimacula yallundae (=Tapesia yallundae*; anamorph *Helgardia herpotrichoides = Pseudocercosporella herpetrichoides), Monilinia fructicola, Sclerotinia sclerotiorum, Sclerotinia minor,* and *Sclerotinia homoeocarpa*;
Ascomycetes in the order Hypocreales such as *Giberella zeae (Fusarium graminearum), G. monoliformis (Fusarium moniliforme), Fusarium solani* and *Verticillium dahliae*;
Ascomycetes in the order Eurotiales such as *Aspergillus flavus* and *A. parasiticus*;
Ascomycetes in the order Diaporthales such as *Cryptosphorella viticola (=Phomopsis viticola), Phomopsis longicolla,* and *Diaporthe phaseolorum*;
Other Ascomycete pathogens including *Magnaporthe grisea, Gaeumannomyces graminis, Rhynchosporium secalis,* and anthracnose pathogens such as *Glomerella acutata (Colletotrichum acutatum), G. graminicola (C. graminicola)* and *G. lagenaria (C. orbiculare)*;
Basidiomycetes in the order Urediniales (the rusts) including *Puccinia recondita, P. striiformis, Puccinia hordei, P. graminis* and *P. arachidis), Hemileia vastatrix* and *Phakopsora pachyrhizi*;
Basidiomycetes in the order Ceratobasidiales such as *Thanatophorum cucumeris (Rhizoctonia solani)* and *Ceratobasidium oryzae-sativae (Rhizoctonia oryzae)*;
Basidiomycetes in the order Polyporales such as *Athelia rolfsii (Sclerotium rolfsii)*;
Basidiomycetes in the order Ustilaginales such as *Ustilago maydis*;
Zygomycetes in the order Mucorales such as *Rhizopus stolonifer*;
Oomycetes in the order Pythiales, including *Phytophthora infestans, P. megasperma, P. parasitica, P. sojae, P. cinnamomi* and *P. capsici,* and *Pythium* pathogens such as *Pythium aphanidermatum, P. graminicola, P. irregulare, P. ultimum* and *P. dissoticum*;
Oomycetes in the order Peronosporales such as *Plasmopara viticola, P. halstedii, Peronospora hyoscyami (=Peronospora tabacina), P. manshurica, Hyaloperonospora parasitica (=Peronospora parasitica), Pseudoperonospora cubensis* and *Bremia lactucae*;
and other genera and species closely related to all of the above pathogens.

In addition to their fungicidal activity, the compositions or combinations also have activity against bacteria such as *Erwinia amylovora, Xanthomonas campestris, Pseudomonas syringae,* and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules.

Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance.

Treatment of genetically modified plants and seeds with compounds of the invention may result in super-additive or enhanced effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are useful in seed treatments for protecting seeds from plant diseases. In the context of the present disclosure and claims, treating a seed means contacting the seed with a biologically effective amount of a compound of this invention, which is typically formulated as a composition of the invention. This seed treatment protects the seed from soil-borne disease pathogens and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

Compounds of this invention and their compositions, both alone and in combination with other fungicides, nematicides and insecticides, are particularly useful in seed treatment for crops including, but not limited to, maize or corn, soybeans, cotton, cereal (e.g., wheat, oats, barley, rye and rice), potatoes, vegetables and oilseed rape.

Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g., fruits, seeds, foliage, stems, bulbs, tubers) can be stored refrigerated or unrefrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

The compounds can also be applied using an unmanned aerial vehicle (UAV) for the dispension of the compositions disclosed herein over a planted area. In some embodiments the planted area is a crop-containing area. In some embodiments, the crop is selected from a monocot or dicot. In some embodiments, the crop is selected form rice, corn, barley, sobean, wheat, vegetable, tobacco, tea tree, fruit tree and sugar cane. In some embodiments, the compositions disclosed herein are formulated for spraying at an ultra-low volume. Products applied by drones may use water or oil as the spray carrier. Typical spray volume (including product) used for drone applications globally. 5.0 liters/ha-100 liters/ha (approximately 0.5-10 gpa). This includes the range of ultra low spray volume (ULV) to low spray volume (LV). Although not common there may be situations where even lower spray volumes could be used as low as 1.0 liter/ha (0.1 gpa).

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1 g) to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b). Of note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of note is a composition which in addition to the Formula 1 compound of component (a), includes as component (b) at least one fungicidal compound selected from the group consisting of the FRAC-defined mode of action (MOA) classes (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis in membranes, (I) melanin synthesis in cell wall, (P) host plant defense induction, multi-site contact activity and unknown mode of action.

FRAC-recognized or proposed target sites of action along with their FRAC target site codes belonging to the above MOA classes are (A1) RNA polymerase I, (A2) adenosine deaminase, (A3) DNA/RNA synthesis (proposed), (A4) DNA topoisomerase, (B1-B3) β-tubulin assembly in mitosis, (B4) cell division (proposed), (B5) delocalization of spectrin-like proteins, (C1) complex I NADH odxido-reductase, (C2) complex II: succinate dehydrogenase, (C3) complex III: cytochrome bc1 (ubiquinol oxidase) at Qo site, (C4) complex III: cytochrome bc1 (ubiquinone reductase) at Qi site, (C5) uncouplers of oxidative phosphorylation, (C6) inhibitors of oxidative phosphorylation, ATP synthase, (C7) ATP production (proposed), (C8) complex III: cytochrome bc1 (ubiquinone reductase) at Qx (unknown) site, (D1) methionine biosynthesis (proposed), (D2-D5) protein synthesis, (E1) signal transduction (mechanism unknown), (E2-E3) MAP/histidine kinase in osmotic signal transduction, (F2) phospholipid biosynthesis, methyl transferase, (F3) lipid peroxidation (proposed), (F4) cell membrane permeability, fatty acids (proposed), (F6) microbial disrupters of pathogen cell membranes, (F7) cell membrane disruption (proposed), (G1) C14-demethylase in sterol biosynthesis, (G2) Δ14-reductase and Δ8→Δ7-isomerase in sterol biosynthesis, (G3) 3-keto reductase, C4-demethylation, (G4) squalene epoxidase in sterol biosynthesis, (H3) trehalase and inositol biosynthesis, (H4) chitin synthase, (H5) cellulose synthase, (I1) reductase in melanin biosynthesis and (I2) dehydratase in melanin biosynthesis.

Of particular note is a composition which in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) succinate dehydrogenase inhibitor fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) azanaphthalene fungicides; (b14) lipid peroxidation inhibitor fungicides; (b15) melanin biosynthesis inhibitor-reductase (MBI-R) fungicides; (b16) melanin biosynthesis inhibitor-dehydratase (MBI-D) fungicides; (b17) sterol biosynthesis inhibitor (SBI): Class III fungicides; (b18) squalene-epoxidase inhibitor fungicides; (b19) polyoxin fungicides; (b20) phenylurea fungicides; (b21) quinone inside inhibitor (QiI) fungicides; (b22) benzamide and thiazole carboxamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) complex I NADH oxidoreductase inhibitor fungicides; (b40) carboxylic acid amide (CAA) fungicides; (b41) tetracycline antibiotic fungicides; (b42) thiocarbamate fungicides; (b43) benzamide fungicides; (b44) microbial fungicides; (b45) $Q_xI$ fungicides; (b46) plant extract fungicides; (b47) host plant defense induction fungicides; (b48) multi-site contact activity fungicides; (b49) fungicides other than fungicides of classes (b1) through (b48); and salts of compounds of classes (b1) through (b48).

Further descriptions of these classes of fungicidal compounds are provided below.

(b1) "Methyl benzimidazole carbamate (MBC) fungicides" (FRAC code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) inhibit a MAP/histidine kinase in osmotic signal transduction. Examples include chlozolinate, iprodione, procymidone and vinclozolin.

(b3) "Demethylation inhibitor (DMI) fungicides" (FRAC code 3) (Sterol Biosynthesis Inhibitors (SBI): Class I) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines, pyridines and triazolinthiones. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, quinconazole, simeconazole, tebuconazole, tetraconazole, triadimefon, triadimenol, triticonazole, uniconazole, uniconazole-P, α-(1-chlorocyclopropyl)-α-[2-(2,2-dichlorocyclopropyl)ethyl]-1H-1,2,4-triazole-1-ethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole. The imidazoles include econazole, imazalil, oxpoconazole, prochloraz, pefurazoate and triflumizole. The pyrimidines include fenarimol, nuarimol and triarimol. The piperazines include triforine. The pyridines include buthiobate, pyrifenox, pyrisoxazole (3-[(3R)-5-(4-chlorophenyl)-2,3-dimethyl3-isoxazolidinyl]pyridine, mixture of 3R,5R- and 3R,5S-isomers) and (αS)-[3-(4-chloro-2-fluorophenyl)5-(2,4-difluorophenyl)-4-isoxazolyl]-3-pyridinemethanol. The triazolinthiones include prothioconazole and 2-[2-(1-chlorocyclopropyl)-4-(2,2-dichlorocyclopropyl)2-hydroxybutyl]-1,2-dihydro-3H-1,2,4-triazole-3-thione. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M (also known as kiralaxyl), furalaxyl, metalaxyl and metalaxyl-M (also known as mefenoxam). The oxazolidinones include oxadixyl. The butyrolactones include ofurace.

(b5) "Amine/morpholine fungicides" (FRAC code 5) (SBI: Class II) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phophorothiolate and dithiolane fungicides. The phosphorothiolates include edifenphos, iprobenfos and pyrazophos. The dithiolanes include isoprothiolane.

(b7) "Succinate dehydrogenase inhibitor (SDHI) fungicides" (FRAC code 7) inhibit Complex II fungal respiration by disrupting a key enzyme in the Krebs Cycle (TCA cycle) named succinate dehydrogenase. Inhibiting respiration prevents the fungus from making ATP, and thus inhibits growth and reproduction. SDHI fungicides include phenylbenzamide, furan carboxamide, oxathiin carboxamide, thiazole carboxamide, pyrazole-4-carboxamide, pyridine carboxamide, phenyl oxoethyl thiophene amides and pyridinylethyl benzamides. The benzamides include benodanil, flutolanil and mepronil. The furan carboxamides include fenfuram. The oxathiin carboxamides include carboxin and oxycarboxin. The thiazole carboxamides include thifluzamide. The pyrazole-4-carboxamides include benzovindiflupyr (N-[9-(dichloromethylene)-1,2,3,4-tetrahydro-1,4-methanonaphthalen-5-yl]-3-(difluoromethyl)-1-methyl-1H-pyrazole-4-carboxamide), bixafen, fluindapyr, fluxapyroxad (3-(difluoromethyl)-1-methyl-N-(3',4',5'-trifluoro[1,1'-biphenyl]-2-yl)-1H-pyrazole-4-carboxamide), furametpyr, isopyrazam (3-(difluoromethyl)-1-methyl-N-[1,2,3,4-tetrahydro-9-(1-methylethyl)-1,4-methanonaphthalen-5-yl]-1H-pyrazole-4-carboxamide), penflufen (N-[2-(1,3-dimethylbutyl)phenyl]-5-fluoro-1,3-dimethyl-1H-pyrazole-4-carboxamide), penthiopyrad, pydiflumetofen, sedaxane (N-[2-[1,1'-bicyclopropyl]-2-ylphenyl]-3-(difluoromethyl)-1-methyl-1H-pyrazole-4-carboxamide), N-[2-(1S,2)-[1,1'-bicyclopropyl]-2-ylphenyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, N-[2-(2,4-dichlorophenyl)2-methoxy-1-methylethyl]-3-(difluoromethyl)-1-methyl-1H-pyrazole-4-carboxamide and N-cyclopropyl-3-(difluoromethyl)-5-fluoro-1-methyl-N-[[2-(1-methylethyl)phenyl]methyl]-1H-pyrazole-4-carboxamide. The pyridine carboxamides include boscalid. The phenyl oxoethyl thiophene amides include isofetamid (N-[1,1-dimethyl-2-[2-methyl-4-(1-methylethoxy)phenyl]-2-oxoethyl]-3-methyl-2-thiophenecarboxamide). The pyridinylethyl benzamides include fluopyram.

(b8) "Hydroxy-(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, coumoxystrobin (methyl ($\alpha$E)-2-[[(3-butyl-4-methyl-2-oxo-2H-1-benzopyran-7-yl)oxy]methyl]-$\alpha$-(methoxymethylene)benzeneacetate), enoxastrobin (methyl ($\alpha$E)-2-[[[(E)-[(2E)-3-(4-chlorophenyl)-1-methyl-2-propen-1-ylidene]amino]oxy]methyl]-$\alpha$-(methoxymethylene)benzeneaceate) (also known as enestroburin), flufenoxystrobin (methyl ($\alpha$E)-2-[[2-chloro-4-(trifluoromethyl)phenoxy]methyl]-$\alpha$-(methoxymethylene)benzeneacetate), picoxystrobin, and pyraoxystrobin (methyl ($\alpha$E)-2-[[[3-(4-chlorophenyl)-1-methyl-1H-pyrazol-5-yl]oxy]methyl]-$\alpha$-(methoxymethylene)benzeneaceate). The methoxycarbamates include pyraclostrobin, pyrametostrobin (methyl N-[2-[[[(1,4-dimethyl-3-phenyl-1H-pyrazol-5-yl)oxy]methyl]phenyl]-N-methoxycarbamate) and triclopyricarb (methyl N-methoxy-N-[2-[[(3,5,6-trichloro-2-pyridinyl)oxy]methyl]phenyl]carbamate). The oximinoacetates include kresoxim-methyl and trifloxystrobin. The oximinoacetamides include dimoxystrobin, fenaminstrobin (($\alpha$E)-2-[[[(E)-[(2E)-3-(2,6-dichlorophenyl)-1-methyl-2-propen-1-ylidene]amino]oxy]methyl]-$\alpha$-(methoxyimino)-N-methylbenzeneacetamide), metominostrobin, orysastrobin and $\alpha$-[methoxyimino]-N-methyl-2-[[[1-[3-(trifluoro-methyl)phenyl]ethoxy]imino]methyl]benzeneacetamide. The dihydrodioxazines include fluoxastrobin. The oxazolidinediones include famoxadone. The imidazolinones include fenamidone. The benzylcarbamates include pyribencarb. Class (b11) also includes mandestrobin (2-[(2,5-dimethylphenoxy)methyl]-$\alpha$-methoxy-N-benzeneacetamide).

(b12) "Phenylpyrrole fungicides" (FRAC code 12) inhibit a MAP/histidine kinase associated with osmotic signal transduction in fungi. Fenpiclonil and fludioxonil are examples of this fungicide class.

(b13) "Azanaphthalene fungicides" (FRAC code 13) are proposed to inhibit signal transduction by a mechanism which is as yet unknown. They have been shown to interfere with germination and/or appressorium formation in fungi that cause powdery mildew diseases. Azanaphthalene fungicides include aryloxyquinolines and quinazolinones. The aryloxyquinolines include quinoxyfen. The quinazolinones include proquinazid.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic hydrocarbon and 1,2,4-thiadiazole fungicides. The aromatic hydrocarboncarbon fungicides include biphenyl, chloroneb, dicloran, quintozene, tecnazene and tolclofos-methyl. The 1,2,4-thiadiazoles include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Sterol Biosynthesis Inhibitor (SBI): Class III fungicides (FRAC code 17) inhibit 3-ketoreductase during C4-demethylation in sterol production. SBI: Class III inhibitors include hydroxyanilide fungicides and amino-pyrazolinone fungicides. Hydroxyanilides include fenhexamid. Amino-pyrazolinones include fenpyrazamine (S-2-propen-1-yl 5-amino-2,3-dihydro-2-(1-methylethyl)-4-(2-methylphenyl)-3-oxo-1H-pyrazole-1-carbothioate).

(b18) "Squalene-epoxidase inhibitor fungicides" (FRAC code 18) (SBI: Class IV) inhibit squalene-epoxidase in the sterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinone reductase. Reduction of ubiquinone is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide and thiazole carboxamide fungicides" (FRAC code 22) inhibit mitosis by binding to β-tubulin and disrupting microtubule assembly. Inhibition of microtubule assembly can disrupt cell division, transport within the cell and cell structure. The benzamides include zoxamide. The thiazole carboxamides include ethaboxam.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase and inositol biosynthesis. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (FRAC code 37) include diclomezine.

(b38) "Thiophene-carboxamide fungicides" (FRAC code 38) are proposed to affect ATP production. Examples include silthiofam.

(b39) "Complex I NADH oxidoreductase inhibitor fungicides" (FRAC code 39) inhibit electron transport in mitochondria and include pyrimidinamines such as diflumetorim, and pyrazole-5-carboxamides such as tolfenpyrad.

(b40) "Carboxylic acid amide (CAA) fungicides" (FRAC code 40) inhibit cellulose synthase which prevents growth and leads to death of the target fungus. Carboxylic acid amide fungicides include cinnamic acid amide, valinamide and other carbamate, and mandelic acid amide fungicides. The cinnamic acid amides include dimethomorph, flumorph and pyrimorph (3-(2-chloro-4-pyridinyl)-3-[4-(1,1-dimethylethyl)phenyl]-1-(4-morpholinyl)-2-propene-1-one). The valinamide and other carbamates include benthiavalicarb, benthiavalicarb-isopropyl, iprovalicarb, tolprocarb (2,2,2-trifluoroethyl N-[(1S)-2-methyl-1-[[(4-methylbenzoyl)amino]methyl]propyl]carbamate) and valifenalate (methyl N-[(1-methylethoxy)carbonyl]-L-valyl-3-(4-chlorophenyl)-β-alaninate) (also known as valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]-butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(b41) "Tetracycline antibiotic fungicides" (FRAC code 41) inhibit growth of fungi by affecting protein synthesis. Examples include oxytetracycline.

(b42) "Thiocarbamate fungicides" (FRAC code 42) include methasulfocarb.

(b43) "Benzamide fungicides" (FRAC code 43) inhibit growth of fungi by delocalization of spectrin-like proteins. Examples include pyridinylmethyl benzamide fungicides such as fluopicolide (now FRAC code 7, pyridinylethyl benzamides).

(b44) "Microbial fungicides" (FRAC code 44) disrupt fungal pathogen cell membranes. Microbial fungicides include *Bacillus* species such as *Bacillus amyloliquefaciens* strains QST 713, FZB24, MB1600, D747 and the fungicidal lipopeptides which they produce.

(b45) "Q$_X$I fungicides" (FRAC code 45) inhibit Complex III mitochondrial respiration in fungi by affecting ubiquinone reductase at an unknown (Q$_X$) site of the cytochrome bc$_1$ complex. Inhibiting mitochondrial respiration prevents normal fungal growth and development. Q$_X$I fungicides include triazolopyrimidylamines such as ametoctradin (5-ethyl-6-octyl[1,2,4]triazolo[1,5-a]pyrimidin-7-amine).

(b46) "Plant extract fungicides" are proposed to act by cell membrane disruption. Plant extract fungicides include terpene hydrocarbons and terpene alcohols such as the extract from *Melaleuca alternifolia* (tea tree).

(b47) "Host plant defense induction fungicides" (FRAC code P) induce host plant defense mechanisms. Host plant defense induction fungicides include benzothiadiazoles, benzisothiazole and thiadiazole-carboxamide fungicides. The benzothiadiazoles include acibenzolar-S-methyl. The benzisothiazoles include probenazole. The thiadiazole-carboxamides include tiadinil and isotianil.

(b48) "Multi-site contact fungicides" inhibit fungal growth through multiple sites of action and have contact/preventive activity. This class of fungicides includes: (b48.1) "copper fungicides" (FRAC code M1)", (b48.2) "sulfur fungicides" (FRAC code M2), (b48.3) "dithiocarbamate fungicides" (FRAC code M3), (b48.4) "phthalimide fungicides" (FRAC code M4), (b48.5) "chloronitrile fungicides" (FRAC code M5), (b48.6) "sulfamide fungicides" (FRAC code M6), (b48.7) multi-site contact "guanidine fungicides" (FRAC code M7), (b48.8) "triazine fungicides" (FRAC code M8), (b48.9) "quinone fungicides" (FRAC code M9), (b48.10) "quinoxaline fungicides" (FRAC code M10) and (b48.11) "maleimide fungicides" (FRAC code M11). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. Multi-site contact "guanidine fungicides" include, guazatine, iminoctadine albesilate and iminoctadine triacetate. "Triazine fungicides" include anilazine. "Quinone fungicides" include dithianon. "Quinoxaline fungicides" include quinomethionate (also known as chinomethionate). "Maleimide fungicides" include fluoroimide.

(b49) "Fungicides other than fungicides of classes (b1) through (b48)" include certain fungicides whose mode of action may be unknown. These include: (b49.1), "phenyl-acetamide fungicides" (FRAC code U6), (b49.2) "aryl-phenyl-ketone fungicides" (FRAC code U8), (b49.3) "guanidine fungicides" (FRAC code U12), (b49.4) "thiazolidine fungicides" (FRAC code U13), (b49.5) "pyrimidinone-hydrazone fungicides" (FRAC code U14) and (b49.6) compounds that bind to oxysterol-binding protein as described in PCT Patent Publication WO 2013/009971. The phenyl-acetamides include cyflufenamid and N-[[(cyclopropylmethoxy)amino][6-(difluoromethoxy)-2,3-difluorophenyl]-methylene]-benzeneacetamide. The aryl-phenyl ketones include benzophenones such as metrafenone, and benzoylpyridines such as pyriofenone (5-chloro-2-methoxy-4-methyl-3-pyridinyl)(2,3,4-trimethoxy-6-methylphenyl)methanone). The quanidines include dodine. The thiazolidines include flutianil ((2Z)-2-[[2-fluoro-5-(trifluoromethyl)phenyl]thio]-2-[3-(2-methoxyphenyl)-2-thiazolidinylidene]acetonitrile). The pyrimidinonehydrazones include ferimzone. The (b49.6) class includes oxathiapiprolin (1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone) and its R-enantiomer which is 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (Registry Number 1003319-79-6). The (b49) class also includes bethoxazin, flometoquin (2-ethyl-3,7-dimethyl-6-[4-(trifluoromethoxy)phenoxy]-4-quinolinyl methyl carbonate), fluoroimide, neo-asozin (ferric methanearsonate), picarbutrazox (1,1-dimethylethyl N-[6-[[[[((Z)1-methyl-1H-tetrazol-5-yl)phenylmethylene]amino]oxy]methyl]-2-pyridinyl]carbamate), pyrrolnitrin, quinomethionate, tebufloquin (6-(1,1-dimethylethyl)-8-fluoro-2,3-dimethyl-4-quinolinyl acetate), tolnifanide (N-(4-chloro-2-nitrophenyl)-N-ethyl-4-methylbenzenesulfonamide), 2-butoxy-6-iodo-3-propyl-4H-1-benzopyran-4-one, 3-butyn-1-yl, N-[6-[[[[(1-methyl-1H-tetrazol-5-yl)phenylmethylene]amino]oxy]methyl]-2-pyridinyl]-carbamate, (N-(4-chloro-2-nitrophenyl)-N-ethyl-4-methylbenzenesulfonamide), N'-[4-[4-chloro-3-(trifluoromethyl)phenoxy]-2,5-dimethylphenyl]-N-ethyl-N-methylmethanimidamide, N-[[(cyclopropylmethoxy)amino][6-(difluoromethoxy)-2,3-difluorophenyl]methylene]benzeneacetamide, 2,6-dimethyl-1H,5H-[1,4]dithiino[2,3-c: 5,6-c']dipyrrole-1,3,5,7(2H,6H)-tetrone, 5-fluoro-2-[(4-methylphenyl)methoxy]-4-pyrimidinamine, 5-fluoro-2-[(4-fluorophenyl)methoxy]-4-pyrimidinamine and 4-fluorophenyl N-[1-[[[1-(4-cyanophenyl)ethyl]sulfonyl]methyl]propyl]carbamate, pentyl N-[6-[[[[(1-methyl-1H-tetrazol-5-yl)phenylmethylene]amino]oxy]methyl]-2-pyridinyl]carbamate, pentyl N-[4-[[[[(1-methyl-1H-tetrazol-5-yl)phenylmethylene]amino]oxy]methyl]-2-thiazolyl]carbamate and pentyl N-[6-[[[[(Z)-(1-methyl-1H-tetrazol-5-yl)phenylmethylene]amino]oxy]methyl]-2-pyridinyl]-carbamate. The (b46) class further includes mitosis- and cell division-inhibiting fungicides besides those of the particular classes described above (e.g., (b1), (b10) and (b22)).

Additional "Fungicides other than fungicides of classes (1) through (46)" whose mode of action may be unknown, or may not yet be classified include a fungicidal compound selected from components (b49.7) through (b49.12), as shown below.

Component (b49.7) Relates to a Compound of Formula b49.7

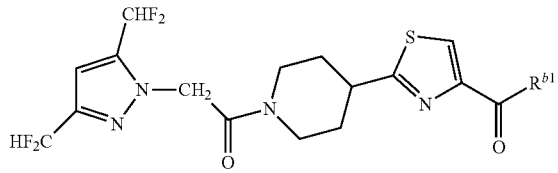

wherein $R^{b1}$ is

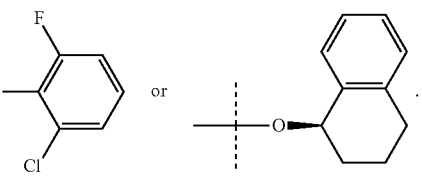

Examples of a compound of Formula b49.7 include (b49.7a) (2-chloro-6-fluorophenyl)-methyl 2-[1-[2-[3,5-bis(difluoromethyl)-1H-pyrazol-1-yl]acetyl]-4-piperidinyl]-4-thiazole-carboxylate (Registry Number 1299409-40-7) and (b49.7b) (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (Registry Number 1299409-42-9). Methods for preparing compounds of Formula b46.2 are described in PCT Patent Publications WO 2009/132785 and WO 2011/051243.

Component (b49.8) Relates to a Compound of Formula b49.8 wherein $R^{b2}$ is $CH_3$, $CF_3$ or $CHF_2$; $R^{b3}$ is $CH_3$, $CF_3$ or $CHF_2$; $R^{b4}$ is halogen or cyano; and n is 0, 1, 2 or 3.

Examples of a compound of Formula b49.8 include (b49.8a) 1-[4-[4-[5-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone. Methods for preparing compounds of Formula b49.8 are described in PCT Patent Application PCT/US11/64324.

Component (b4799) Relates to a Compound of Formula b49.9

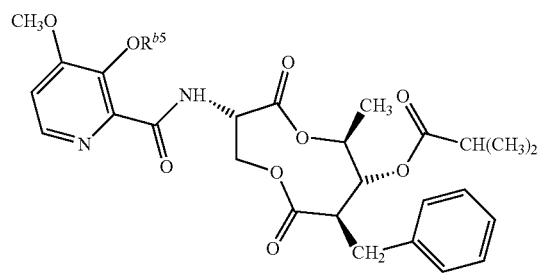

b49.9 wherein $R^{b5}$ is —$CH_2OC(O)CH(CH_3)_2$, —$C(O)CH_3$, —$CH_2OC(O)CH_3$, —$C(O)OCH_2CH(CH_3)_2$ or

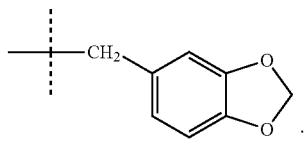

Examples of a compound of Formula b49.9 include (b49.9a) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate (Registry Number 517875-34-2), (b49.9b) (3S,6S,7R,8R)-3-[[[3-(acetyloxy)-4-methoxy-2-pyridinyl]-carbonyl]amino]-6-methyl-4,9-dioxo-8-(phenylmethyl)-1,5-dioxonan-7-yl 2-methylpropanoate (Registry Number 234112-93-7), (b49.9c) (3S,6S,7R,8R)-3[[[3[(acetyloxy)-methoxy]-4-methoxy-2-pyridinyl]carbonyl]amino]-6-methyl-4,9-dioxo-8-(phenylmethyl)-1,5-dioxonan-7-yl 2-methylpropanoate (Registry Number 517875-31-9), (b49.9d) (3S,6S,7R,8R)-3-[[[4-methoxy-3-[[(2-methyl-propoxy)carbonyl]oxy]-2-pyridinyl]carbonyl]-amino]6-methyl-4,9-dioxo-8-(phenylmethyl)-1,5-dioxonan-7-yl 2-methylpropanoate (Registry Number 328256-72-0), and (b49.9e) N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenyl-methyl)L-arabinonoyl]-L-serine, (1→4')-lactone (Registry Number 1285706-70-8). Methods for preparing compounds of Formula b49.9 are described in PCT Patent Publications WO 99/40081, WO 2001/014339, WO 2003/035617 and WO 2011044213.

Component (b49.10) Relates to a Compound of Formula b49.10

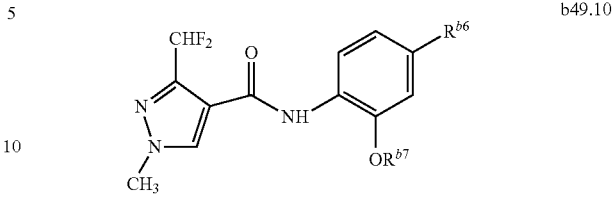

b49.10 wherein $R^{b6}$ is H or F, and $R^{b7}$ is —$CF_2CHFCF_3$ or —$CF_2CF_2H$. Examples of a compound of Formula b49.10 are (b49.10a) 3-(difluoromethyl)-N-[4-fluoro-2-(1,1,2,3,3,3-hexafluoro-propoxy)phenyl]-1-methyl-1H-pyrazole-4-carboxamide (Registry Number 1172611-40-3) and (b49.10b) 3-(difluoromethyl)-1-methyl-N-[2-(1,1,2,2-tetrafluoroethoxy)phenyl]-1H-pyrazole4-carboxamide (Registry Number 923953-98-4). Compounds of Formula 49.10 can be prepared by methods described in PCT Patent Publication WO 2007/017450.

Component b49.11 Relates a Compound of Formula b49.11

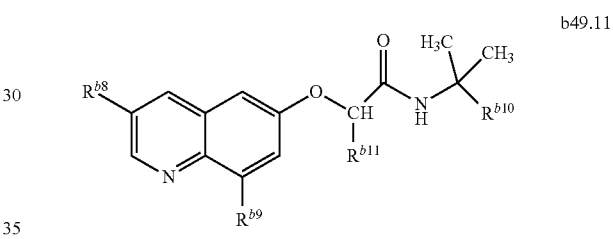

b49.11 wherein
$R^{b8}$ is halogen, $C_1$-$C_4$ alkoxy or $C_2$-$C_4$ alkynyl;
$R^{b9}$ is H, halogen or $C_1$-$C_4$ alkyl;
$R^{b10}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{b11}$ is methyl or —$Y^{b13}$—$R^{b12}$;
$R^{b12}$ is $C_1$-$C_2$ alkyl; and
$Y^{b13}$ is $CH_2$, O or S.

Examples of compounds of Formula b49.11 include (b49.11a) 2-[(3-bromo-6-quinolinyl)-oxy]-N-(1,1-dimethyl-2-butyn-1-yl)-2-(methylthio)acetamide, (b49.11b) 2[(3-ethynyl-6-quinolinyl)oxy]-N-[1-(hydroxymethyl)-1-methyl-2-propyn-1-yl]-2-(methylthio)acetamide, (b49.11c) N-(1,1-dimethyl-2-butyn-1-yl)-2-[(3-ethynyl-6-quinolinyl)oxy]-2-(methylthio)-acetamide, (b49.11d) 2-[(3-bromo-8-methyl-6-quinolinyl)oxy]-N-(1,1-dimethyl-2-propyn-1-yl)-2-(methylthio)acetamide and (b49.11e) 2-[(3-bromo-6-quinolinyl)oxy]-N-(1,1-di-methylethyl)butanamide.

Compounds of Formula b49.11, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098.

Component 49.12 relates to N'-[4-[[3-[(4-chlorophenyl)methyl]-1,2,4-thiadiazol-5-yl]oxy]-2,5-dimethylphenyl]-N-ethyl-N-methylmethanimidamide, which is believed to inhibit C24-methyl transferase involved in the biosynthesis of sterols.

Therefore of note is a mixture (i.e. composition) comprising a compound of Formula 1 and at least one fungicidal compound selected from the group consisting of the afore-described classes (1) through (49). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (49). Also of particular note is a composition comprising said mixture (in fungicidally effective amount) and further comprising at least one additional surfactant selected from the group consisting of surfactants, solid diluents and liquid diluents.

Examples of component (b) fungicides include acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, captafol, captan, carbendazim, carboxin, carpropamid, chloroneb, chlorothalonil, chlozolinate, clotrimazole, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, edifenphos, enoxastrobin (also known as enestroburin), epoxiconazole, etaconazole, ethaboxam, ethirimol, etridiazole, famoxadone, fenamidone, fenarimol, fenaminstrobin, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, flometoquin, fluazinam, fludioxonil, flufenoxystrobin, fluindapyr, flumorph, fluopicolide, fluopyram, flouroimide, fluoxastrobin, fluquinconazole, flusilazole, flusulfamide, flutianil, flutolanil, flutriafol, fluxapyroxad, folpet, fthalide, fuberidazole, furalaxyl, furametpyr, guazatine, hexaconazole, hymexazole, imazalil, imibenconazole, iminoctadine albesilate, iminoctadine triacetate, iodocarb, ipconazole, iprobenfos, iprodione, iprovalicarb, isoconazole, isofetamid, isoprothiolane, isopyrazam, isotianil, kasugamycin, kresoxim-methyl, mancozeb, mandepropamid, mandestrobin, maneb, mepanipyrim, mepronil, meptyldinocap, metalaxyl (including metalaxyl-M/mefenoxam), metconazole, methasulfocarb, metiram, metominostrobin, metrafenone, miconazole, myclobutanil, naftifine, neo-asozin, nuarimol, octhilinone, ofurace, orysastrobin, oxadixyl, oxathiapiprolin, oxolinic acid, oxpoconazole, oxycarboxin, oxytetracycline, pefurazoate, penconazole, pencycuron, penflufen, penthiopyrad, phosphorous acid (including salts thereof, e.g., fosetyl-aluminum), picarbutrazox, picoxystrobin, piperalin, polyoxin, probenazole, prochloraz, procymidone, propamacarb, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyrisoxazole, pyroquilon, pyrrolnitrin, quinconazole, quinomethionate, quinoxyfen, quintozene, sedaxane, silthiofam, simeconazole, spiroxamine, streptomycin, sulfur, tebuconazole, tebufloquin, teclofthalam, tecnazene, terbinafine, tetraconazole, thiabendazole, thifluzamide, thiophanate, thiophanate-methyl, thiram, tiadinil, tolclofos-methyl, tolnifanide, tolprocarb, tolyfluanid, triadimefon, triadimenol, triarimol, triticonazole, triazoxide, tribasic copper sulfate, tricyclazole, triclopyricarb, tridemorph, trifloxystrobin, triflumizole, triforine, trimorphamide, uniconazole, uniconazole-P, validamycin, valifenalate (also known as valiphenal), vinclozolin, zineb, ziram, zoxamide, (3S,6S,7R, 8R)-3-[[[3-[(acetyloxy)methoxy]-4-methoxy-2-pyridinyl] carbonyl]amino]-6-methyl-4,9-dioxo-8-(phenylmethyl)-1, 5-dioxonan-7-yl 2-methylpropanoate, (3S,6S,7R,8R)-3-[[[3-(acetyloxy)-4-methoxy-2-pyridinyl]carbonyl]-amino]-6-methyl-4,9-dioxo-8-(phenylmethyl)-1,5-dioxonan-7-yl 2-methylpropanoate, N-[[3-(1,3-benzodioxol-5-yl-methoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4')-lactone, N-[2-(1S,2R)-[1,1'-bicyclopropyl]-2-ylphenyl]-3-(difluoromethyl)-1-methyl-1H-pyrazole-4-carboxamide, 2-[(3-bromo-6-quinolinyl) oxy]-N-(1,1-dimethyl-2-butyn-1-yl)-2-(methylthio)-acetamide, 2-[(3-bromo-6-quinolinyl)oxy]-N-(1,1-dimethylethyl)butanamide, 2-[(3-bromo-8-methyl-6-quinolinyl)oxy]-N-(1,1-dimethyl-2-propyn-1-yl)-2-(methylthio)acetamide, 2-butoxy-6-iodo-3-propyl-4H-1-benzopyran-4-one, 3-butyn-1-yl N-[6-[[[[(1-methyl-1H-tetrazol-5-yl)phenylmethylene]amino]oxy]methyl]-2-pyridinyl]carbamate, α-(1-chloro-cyclopropyl)-α-[2-(2,2-dichlorocyclopropyl)ethyl]-1H-1,2,4-triazole-1-ethanol, 2-[2-(1-chlorocyclopropyl)-4-(2,2-dichlorocyclopropyl)-2-hydroxybutyl]-1,2-dihydro-3H-1,2,4-triazole-3-thione, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]-methyl]-1H-1,2,4-triazole, rel-2-[[(2R,3S)-3-(2-chlorophenyl)-2-(2, 4-difluorophenyl)-2-oxiranyl]methyl]-1,2-dihydro-3H-1,2, 4-triazole-3-thione, rel-1-[[(2R,3S)-3-(2-chlorophenyl)-2-(2,4-difluorophenyl)-2-oxiranyl]methyl]-5-(2-propen-1-ylthio)-1H-1,2,4-triazole, 3-[5-(4-chlorophenyl)-2,3-dimethyl-3-isoxazolidinyl]pyridine, (2-chloro-6-fluorophenyl)-methyl 2-[1-[2-[3,5-bis(difluoromethyl)-1H-pyrazol-1-yl]acetyl]-4-piperidinyl]-4-thiazole-carboxylate, N'-[4-[[3-[(4-chlorophenyl)methyl]-1,2,4-thiadiazol-5-yl] oxy]-2,5-dimethyl-phenyl]-N-ethyl-N-methyl-methanimidamide, N-[2-[4-[[3-(4-chlorophenyl)-2-propyn-1-yl]-oxy]-3-methoxyphenyl]ethyl]-3-methyl-2-[(methylsulfonyl) amino]butanamide, N-[2-[4-[[3-(4-chlorophenyl)-2-propyn-1-yl]oxy]-3-methoxyphenyl]ethyl]-3-methyl-2-[(ethylsulfonyl)-amino]butanamide, N'-[4-[4-chloro-3-(trifluoromethyl)phenoxy]-2,5-dimethylphenyl]-N-ethyl-N-methylmethanimidamide, N-cyclopropyl-3-(difluoromethyl)-5-fluoro-1-methyl-N-[[2-(1-methylethyl) phenyl]methyl]-1H-pyrazole-4-carboxamide, N-[[(cyclopropylmethoxy)-amino][6-(difluoromethoxy)-2, 3-difluorophenyl]methylene]benzeneacetamide, N-[2-(2,4-dichlorophenyl)-2-methoxy-1-methylethyl]-3-(difluoromethyl)-1-methyl-1H-pyrazole-4-carboxamide, N-(3',4'-difluoro[1,1'-biphenyl]-2-yl)-3-(trifluoromethyl)-2-pyrazinecarboxamide, 3-(difluoromethyl)-N-(2,3-dihydro-1,1,3-trimethyl-1H-inden-4-yl)-1-methyl-1H-pyrazole-4-carboxamide, 3-(difluoromethyl)-N-[4-fluoro-2-(1,1,2,3,3, 3-hexafluoropropoxy)-phenyl]-1-methyl-1H-pyrazole-4-carboxamide, 5,8-difluoro-N-[2-[3-methoxy-4-[[4-(trifluoromethyl)-2-pyridinyl]oxy]phenyl]ethyl]-4-quinazolinamine, 3-(difluoromethyl)-1-methyl-N-[2-(1,1,2, 2-tetrafluoroethoxy)phenyl]-1H-pyrazole-4-carboxamide, 1-[4-[4-[5R-[(2,6-difluorophenyl)methyl]-4,5-dihydro-3-isoxazolyl]-2-thiazolyl]-1-piperdinyl]-2-[5-methyl-3-(trifluoromethyl)-1H-pyrazol-1-yl]ethanone, N-(1,1-dimethyl-2-butyn-1-yl)-2-[(3-ethynyl-6-quinolinyl)oxy]-2-

(methylthio)acetamide, 2,6-dimethyl-1H,5H-[1,4]dithiino[2,3-c:5,6-c']dipyrrole-1,3,5,7(2H,6H)-tetrone, 2-[(3-ethynyl-6-quinolinyl)oxy]-N-[1-(hydroxymethyl)-1-methyl-2-propyn-1-yl]-2-(methylthio)acetamide, 4-fluorophenyl N-[1-[[[1-(4-cyanophenyl)ethyl]sulfonyl]methyl]propyl]carbamate, 5-fluoro-2-[(4-fluorophenyl)methoxy]-4-pyrimidinamine, 5-fluoro-2-[(4-methylphenyl)methoxy]-4-pyrimidinamine, (3S,6S,7R,8R)-3-[[[4-methoxy-3-[[(2-methyl propoxy)carbonyl]oxy]-2-pyridinyl]-carbonyl]amino]-6-methyl-4,9-dioxo-8-(phenylmethyl)-1,5-dioxonan-7-yl-2-methylpropanoate, α-(methoxyimino)-N-methyl-2-[[[1-[3-(trifluoromethyl)phenyl]ethoxy]imino]-methyl]benzeneacetamide, [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate, pentyl N-[6-[[[[(1-methyl-1H-tetrazol-5-yl)-phenylmethylene]amino]oxy]methyl]-2-pyridinyl]carbamate, pentyl N-[4-[[[[(1-methyl-1H-tetrazol-5-yl)phenylmethylene]amino]oxy]methyl]-2-thiazolyl]carbamate, and pentyl N-[6-[[[[(Z)-(1-methyl-1H-tetrazol-5-yl)phenylmethylene]amino]oxy]methyl]-2-pyridinyl]-carbamate and (1R)-1,2,3,4-tetrahydro-1-naphthalenyl 2-[1-[2-[3,5-bis(difluoromethyl))-1H-pyrazol-1-yl]acetyl]-4-piperidinyl]-4-thiazolecarboxylate. Therefore, of note is a fungicidal composition comprising as component (a) a compound of Formula 1 (or an N-oxide or salt thereof) and as component (b) at least one fungicide selected from the preceding list.

Of particular note are combinations of compounds of Formula 1 (or an N-oxide or salt thereof) (i.e. Component (a) in compositions) with azoxystrobin, benzovindiflupyr, bixafen, captan, carpropamid, chlorothalonil, copper hydroxide, copper oxychloride, copper sulfate, cymoxanil, cyproconazole, cyprodinil, diethofencarb, difenoconazole, dimethomorph, epoxiconazole, ethaboxam, fenarimol, fenhexamid, fluazinam, fludioxonil, fluindapyr, fluopyram, flusilazole, flutianil, flutriafol, fluxapyroxad, folpet, iprodione, isofetamid, isopyrazam, kresoxim-methyl, mancozeb, mandestrobin, meptyldinocap, metalaxyl (including metalaxyl-M/mefenoxam), metconazole, metrafenone, myclobutanil, oxathiapiprolin, penflufen, penthiopyrad, phosphorous acid (including salts thereof, e.g., fosetyl-aluminum), picoxystrobin, propiconazole, proquinazid, prothioconazole, pyraclostrobin, pyrimethanil, sedaxane spiroxamine, sulfur, tebuconazole, thiophanatemethyl, trifloxystrobin, zoxamide, α-(1-chlorocyclopropyl)-α-[2-(2,2-dichlorocyclopropyl)ethyl]-1H-1,2,4-triazole-1-ethanol, 2-[2-(1-chlorocyclopropyl)-4-(2,2-dichlorocyclopropyl)-2-hydroxybutyl]-1,2-dihydro-3H-1,2,4-triazole-3-thione, N-[2-(2,4-dichlorophenyl)-2-methoxy-1-methylethyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 1,1-dimethylethyl N-[6-[[[[(1-methyl-1H-tetrazol-5-yl)phenylmethylene]amino]oxy]methyl]-2-pyridinyl]-carbamate, 2,6-dimethyl-1H,5H-[1,4]dithiino[2,3-c:5,6-c']dipyrrole-1,3,5,7(2H,6H)-tetrone, 5-fluoro-2-[(4-fluorophenyl)methoxy]-4-pyrimidinamine, 5-fluoro-2-[(4-methylphenyl)-methoxy]-4-pyrimidinamine, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[[(2R,3S)-3-(2-chlorophenyl)-2-(2,4-difluorophenyl)-2-oxiranyl]methyl]-5-(2-propen-1-ylthio)-1H-1,2,4-triazole (i.e. as Component (b) in compositions).

Examples of other biologically active compounds or agents with which compounds of this invention can be formulated are: invertebrate pest control compounds or agents such as abamectin, acephate, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl] methyl cyclopropanecarboxylate), amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), flupiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[[(6-chloro-3-pyridinyl)-methyl](2,2-difluoroethyl)amino]-2(5H)-furanone), tau-fluvalinate, flufenerim (UR-50701), flufenoxuron, fonophos, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hydramethylnon, imidacloprid, indoxacarb, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methomyl, methoprene, methoxychlor, methoxyfenozide, metofluthrin, milbemycin oxime, momfluorothrin ([2,3,5,6-tetrafluoro-4-(methoxymethyl)phenyl]methyl-3-(2-cyano-1-propen-1-yl)-2,2-dimethylcyclopropanecarboxylate), monocrotophos, nicotine, nitenpyram, nithiazine, novaluron, noviflumuron (XDE-007), oxamyl, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriminostrobin (methyl (αE)-2-[[[2-[(2,4-dichlorophenyl)-amino]-6-(trifluoromethyl)-4-pyrimidinyl]oxy]methyl]-α-(methoxymethylene)benzeneacetate), pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a compound of the invention with other biologically active compounds or agents can result in a less-than-additive (i.e. safening) effect on organisms beneficial to the agronomic environment. For example, a compound of the invention may safen a herbicide on crop plants or protect a beneficial insect species (e.g., insect predators, pollinators such as bees) from an insecticide.

Fungicides of note for formulation with compounds of Formula 1 to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, flufenoxystrobin, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Invertebrate pest control compounds or agents with which compounds of Formula 1 can be formulated to provide mixtures useful in seed treatment include but are not limited to abamectin, acetamiprid, acrinathrin, afidopyropen, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyclaniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, fluensulfone, flufenoxuron, flufiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, momfluorothrin, nitenpyram, nithiazine, novaluron, oxamyl, pyflubumide, pymetrozine, pyrethrin, pyridaben, pyriminostrobin, pyridalyl, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumuron, *Bacillus thuringiensis* delta-endotoxins, strains of *Bacillus thuringiensis* and strains of *Nucleo polyhydrosis* viruses.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM I-1582 (GB-126) which is commercially available as BioNem™. A suitable *Bacillus cereus* strain is strain NCMM 1-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The following TESTS demonstrate the control efficacy of compounds of this invention on specific pathogens. The pathogen control protection afforded by the compounds is not limited, however, to these species. See Index Tables A-B below for compound descriptions. The following abbreviations are used in Index Table A: Me means methyl, i-Pr means iso-propyl, MeO means methoxy and —NO$_2$ means nitro. The abbreviation "Cmpd." stands for "Compound", and the abbreviation "Ex." stands for "Example" and is followed by a number indicating in which example the compound is prepared. In Index Table A, the locant numbers listed for substituents R$^4$ and R$^5$ are as indicated in the structure above the table. The order of listing substituents R$^4$ and R$^5$ may be different from the Chemical Abstracts naming system if the difference does not affect the meaning. For example, Compound 1 in Index Table A lists the substituent R$^5$ is at the 6-position (i.e. 6-F) whereas the CAS name for Compound 1 is 4-(2-bromo-4,6-difluorophenyl)-N-(2-fluoro-6-nitrophenyl)-1,3-dimethyl-1H-pyrazol-5-amine.

The numerical value reported in the column "AP$^+$ (M+1)", is the molecular weight of the observed molecular ion formed by addition of H$^+$ (molecular weight of 1) to the molecule having the greatest isotopic abundance (i.e. M); the numerical value reported in the column "AP$^-$ (M−1)", is the molecular weight of the observed molecular ion formed by loss of H$^+$ (molecular weight of 1) from the molecule having the greatest isotopic abundance (i.e. M). The presence of molecular ions containing one or more higher atomic weight isotopes of lower abundance (e.g., $^{37}$Cl, $^{81}$Br) is not reported. The reported M+1 and M−1 peaks were observed by mass spectrometry using electrospray ionization (ESI) or atmospheric pressure chemical ionization (APCI).

INDEX TABLE A

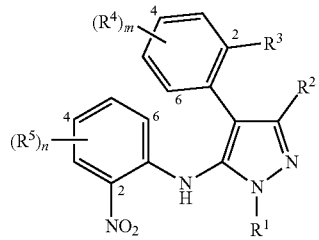

A dash "—" in the R$^5$ column means that no R$^5$ substituent is present and the remaining carbon valences are occupied by hydrogen atoms.

| Cmpd. No. | R$^1$ | R$^2$ | R$^3$ | (R$^4$)$_m$ | (R$^5$)$_n$ | m.p. (° C.) | AP$^+$ (M + 1) | AP$^-$ (M − 1) |
|---|---|---|---|---|---|---|---|---|
| 1 | CH$_3$ | CH$_3$ | Br | 4,6-di-F | 6-F | 133-137 | 442 | |
| 2 | CH$_3$ | CH$_3$ | F | 4-CH$_3$O, 6-F | 4-F, 6-Cl | 176-180 | 427 | |
| 3 | CH$_3$ | Et | F | 4-F | 4-Br, 6-Cl | 148-149 | 437 | |
| 4 | CH$_3$ | CH$_3$ | Cl | 4-F | 4-MeOCH$_2$ | 106-110 | 405 | |
| 5 | CH$_3$ | CH$_3$ | Cl | 4-F | 4-CH═CCH$_2$O | 123-127 | 415 | |
| 6 | CH$_3$ | CH$_3$ | Cl | 4-F | 4-CH$_3$CH$_2$ | 109-113 | 389 | |
| 7 | CH$_3$ | CH$_3$ | Cl | 4-F | 5,6-di-F | 131-135 | 397 | |
| 8 | CH$_3$ | CH$_3$ | Cl | 4-F | 4-Br, 6-Cl | 180-184 | 475 | |
| 9 | CH$_3$ | CH$_3$ | Cl | 4-Cl | 4,6-di-F | 138-142 | 414 | |
| 10 | CH$_3$ | CH$_3$ | Cl | 4-Cl | 4-F, 6-Cl | 178-182 | 430 | |
| 11 | CH$_3$ | CH$_3$ | Cl | 4-Cl | 4-Cl, 6-F | 164-168 | 430 | |
| 12 | CH$_3$ | CH$_3$ | F | 4-Cl | 6-F | 151-155 | 379 | |
| 13 | CH$_3$ | CH$_3$ | F | 4-Cl | 4,6-di-F | 154-158 | 397 | |
| 14 | CH$_3$ | CH$_3$ | Cl | 4-N═C | 4-CH$_3$ | 166-170 | 382 | |
| 15 | CH$_3$ | CH$_3$ | F | 4-F | 4-CH$_3$, 6-Cl | | 393 | |
| 16 | CH$_3$ | Et | F | 4-F | 4-CH$_3$, 6-Cl | | 407 | |
| 17 | CH$_3$ | Et | F | 4-F | 6-Cl | 116-118 | 393 | |
| 18 | CH$_3$ | CH$_3$ | Cl | 4-N═C | 4-F, 6-Cl | 182-186 | 420 | |
| 19 | CH$_3$ | CH$_3$ | Cl | 4-F | 4-F, 6-Cl | 153-157 | 413 | |
| 20 | CH$_3$ | CH$_3$ | Br | 4-F | 4-F | 127-131 | 424 | |
| 21 | CH$_3$ | CH$_3$ | Br | 4-F | 4-Br | 112-116 | 485 | |
| 22 | CH$_3$ | CH$_3$ | Cl | 6-F | 4-Cl | 173-177 | 396 | |
| 23 | CH$_3$ | CH$_3$ | Cl | 6-F | 4-CH$_3$O, 6-F | 167-171 | 409 | |
| 24 | CH$_3$ | CH$_3$ | Cl | 6-F | 4-CH$_3$, 6-Cl | 184-188 | 410 | |
| 25 | CH$_3$ | CH$_3$ | Cl | 6-F | 6-F | 130-134 | 379 | |
| 26 | CH$_3$ | CH$_3$ | Cl | q4-F | 4-CH$_3$ | 118-122 | 375 | |
| 27 | CH$_3$ | CH$_3$ | Cl | 4-CH$_3$O | 6-F | 145-149 | 391 | |
| 28 | CH$_3$ | CH$_3$ | Cl | 4-F | 4-CF$_2$HO | | 427 | |
| 29 | CH$_3$ | CH$_3$ | Cl | 4-F | 4-N═CCH$_2$O | 189-193 | 416 | |
| 30 | CH$_3$ | CH$_3$ | Cl | 4-F | 5-F | | 379 | |
| 31 | CH$_3$ | CH$_3$ | Cl | 4-F | 4-CH$_3$, 6-Cl | 164-168 | 410 | |
| 32 | CH$_3$ | CH$_3$ | Cl | 4-F | 4,5-di-F | 123-127 | 397 | |
| 33 | CH$_3$ | CH$_3$ | Cl | 4-F | 4-Cl, 6-CH$_3$ | 155-159 | 410 | |
| 34 | CH$_3$ | CH$_3$ | Cl | 4-F | 3-Cl | 105-109 | 396 | |
| 35 | CH$_3$ | CH$_3$ | Me | 4-CH$_3$O | 6-Cl | 195-199 | 389 | |

INDEX TABLE A-continued

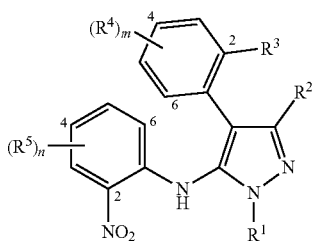

A dash "—" in the $R^5$ column means that no $R^5$ substituent is present and the remaining carbon valences are occupied by hydrogen atoms.

| Cmpd. No. | $R^1$ | $R^2$ | $R^3$ | $(R^4)_m$ | $(R^5)_n$ | m.p. (° C.) | $AP^+$ (M + 1) | $AP^-$ (M − 1) |
|---|---|---|---|---|---|---|---|---|
| 36 | $CH_3$ | $CH_3$ | Cl | 4-F | 4-$CF_2HCH_2O$ | | 442 | |
| 37 | $CH_3$ | $CH_3$ | Br | 4-F | 4,6-di-Cl | 185-189 | 475 | |
| 38 | $CH_3$ | $CH_3$ | Cl | 6-F | 6-Cl | 159-163 | 396 | |
| 39 | $CH_3$ | $CH_3$ | Cl | 6-F | 4,6-di-F | 146-150 | 397 | |
| 40 | $CH_3$ | $CH_3$ | Br | 4-F | 4-$CH_3$, 6-F | 152-156 | 438 | |
| 41 | $CH_3$ | $CH_3$ | Br | 4-F | 6-Cl | 161-165 | 440 | |
| 42 | $CH_3$ | $CH_3$ | Br | 4-F | 6-$CH_3$ | 148-152 | 420 | |
| 43 | $CH_3$ | $CH_3$ | Br | 4-F | 4-F, 6-Cl | 208-212 | 458 | |
| 44 | $CH_3$ | $CH_3$ | Cl | 6-F | 4-F | 138-142 | 379 | |
| 45 | $CH_3$ | Et | F | 4-F | 4-$CH_3O$ | | 389 | |
| 46 | $CH_3$ | Et | F | 4-F | 6-F | | 377 | |
| 47 | $CH_3$ | $CH_3$ | Cl | 4-F | 4-I, 6-F | 143-148 | 505 | |
| 48 | $CH_3$ | $CH_3$ | Me | 4-$CH_3O$ | 6-F | 145-150 | 371 | |
| 49 | $CH_3$ | $CH_3$ | Cl | 6-F | 4-F, 6-Cl | 174-178 | 414 | |
| 50 | $CH_3$ | Et | F | 4-F | 4,6-di-F | | | 393 |
| 51 | $CH_3$ | $CH_3$ | Br | 4-F | 4,6-di-F | 159-163 | 442 | |
| 52 | $CH_3$ | $CH_3$ | Br | 4-F | 4-$CH_3O$ | | 435 | |
| 53 | $CH_3$ | $CH_3$ | Cl | 6-Cl | 6-F | 145-149 | 396 | |
| 54 | $CH_3$ | $CH_3$ | Cl | 6-Cl | 4-F | 151-155 | 396 | |
| 55 | $CH_3$ | $CH_3$ | F | 4-F | 4-Br, 6-Cl | 179-183 | 458 | |
| 56 | $CH_3$ | $CH_3$ | F | 4-F | 4-Br, 6-F | 136-140 | 442 | |
| 57 | $CH_3$ | $CH_3$ | F | 4-F | 4-$CH_3O$, 6-F | 143-147 | 393 | |
| 58 | $CH_3$ | $CH_3$ | F | 4-F | 4,6-di-F | 131-135 | 381 | |
| 59 | $CH_3$ | $CH_3$ | Cl | 4-F | 4,6-di-Cl | 180-184 | 429 | |
| 60 | $CH_3$ | $CH_3$ | Br | 4-F | 6-F | 132-136 | 423 | |
| 61 (Ex. 3) | $CH_3$ | $CH_3$ | Cl | 4-F | 4-Br, 6-F | 149-153 | 457 | |
| 62 | $CH_3$ | $CH_3$ | F | 4,6-di-F | 6-F | 141-145 | 381 | |
| 63 | $CH_3$ | $CH_3$ | F | 6-F | 6-F | 160-164 | 363 | |
| 64 | $CH_3$ | $CH_3$ | Cl | 4-$CH_3O$ | 4,6-di-F | 169-174 | 409 | |
| 65 | $CH_3$ | $CH_3$ | Cl | 4-$CH_3O$ | 4,6-di-Cl | 208-213 | 442 | |
| 66 | $CH_3$ | $CH_3$ | Cl | 4-$CH_3O$ | 4-$CH_3$, 6-Cl | 164-169 | 422 | |
| 67 | $CH_3$ | $CH_3$ | F | 4-F | 4-F, 6-Cl | 163-167 | 397 | |
| 68 | $CH_3$ | $CH_3$ | Cl | 4,6-di-F | 6-F | 124-128 | 397 | |
| 69 | $CH_3$ | $CH_3$ | Cl | 4-Cl | 6-F | 169-173 | 395 | |
| 70 | $CH_3$ | $CH_3$ | F | 4-$CH_3O$, 6-F | 6-F | 148-152 | 393 | |
| 71 | Et | $CH_3$ | Cl | 4-F | 6-F | 112-116 | 393 | |
| 72 | $CH_3$ | Et | Cl | 4-F | 6-F | 117-121 | 394 | |
| 73 | $CH_3$ | $CH_3$ | Cl | 4-$CH_3O$ | 4-F, 6-Cl | 167-172 | 426 | |
| 74 | $CH_3$ | $CH_3$ | Cl | 4-$CH_3O$ | 4-Cl | 148-153 | 408 | |
| 75 | $CH_3$ | $CH_3$ | F | 6-F | 4,6-di-F | 195-199 | 381 | |
| 76 | $CH_3$ | $CH_3$ | F | 6-F | 4-F, 6-Cl | 184-188 | 397 | |
| 77 | $CH_3$ | $CH_3$ | F | 6-F | 6-Cl | 154-158 | 379 | |
| 78 | $CH_3$ | $CH_3$ | F | 4-F | 4-Cl | 178-182 | 379 | |
| 79 | $CH_3$ | $CH_3$ | F | 4-F | 6-Cl | 139-143 | 379 | |
| 80 | $CH_3$ | $CH_3$ | Cl | 4-F | 4-$CH_3O$, 6-Cl | 184-189 | 426 | |
| 81 | $CH_3$ | $CH_3$ | Cl | 4-$CH_3O$ | 4-Cl, 6-F | 165-170 | 426 | |
| 82 | $CH_3$ | $CH_3$ | F | 4-$CH_3O$, 6-F | 4,6-di-Cl | 162-167 | 444 | |
| 83 | $CH_3$ | $CH_3$ | F | 4-$CH_3O$, 6-F | 4-F | 172-177 | 393 | |
| 84 | $CH_3$ | $CH_3$ | F | 4-$CH_3O$, 6-F | 4,6-di-F | 178-182 | 411 | |
| 85 | $CH_3$ | $CH_3$ | Cl | 4-F | 4-$CH_3O$, 6-F | 125-130 | 409 | |
| 86 | $CH_3$ | $CH_3$ | F | 4-$CH_3O$, 6-F | 4-Cl, 6-F | 144-149 | 427 | |
| 87 | $CH_3$ | $CH_3$ | F | 6-F | 4-$CH_3O$ | | 375 | |
| 88 | $CH_3$ | $CH_3$ | F | 4-F | 4-$CH_3O$ | | 375 | |
| 89 | $CH_3$ | $CH_3$ | Cl | 4,6-di-F | 4-$CH_3O$ | | 409 | |
| 90 | $CH_3$ | $CH_3$ | Br | 4-F | 4-$CH_3$ | | 419 | |
| 91 | $CH_3$ | $CH_3$ | Cl | 4-F | 4-Br | 93-97 | 437 | |
| 92 | $CH_3$ | $CH_3$ | Cl | 4-F | 4-Cl | 98-102 | 394 | |
| 93 (Ex. 4) | $CH_3$ | $CH_3$ | Cl | 4-F | 4-$CH_3$, 6-F | 147-151 | 393 | |
| 94 | $CH_3$ | $CH_3$ | Cl | 4-F | 4-$CF_3O$ | 124-128 | 445 | |
| 95 | $CH_3$ | Et | Cl | 4-F | 4,6-di-F | 107-111 | 412 | |
| 96 | $CH_3$ | $CH_3$ | F | 6-F | 4,6-di-Cl | 185-189 | 414 | |

INDEX TABLE A-continued

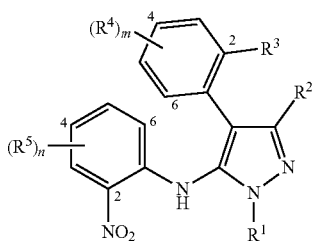

A dash "—" in the R⁵ column means that no $R^5$ substituent is present and the remaining carbon valences are occupied by hydrogen atoms.

| Cmpd. No. | $R^1$ | $R^2$ | $R^3$ | $(R^4)_m$ | $(R^5)_n$ | m.p. (° C.) | AP⁺ (M + 1) | AP⁻ (M − 1) |
|---|---|---|---|---|---|---|---|---|
| 97 | CH₃ | CH₃ | F | 6-F | 4-CH₃O, 6-F | 159-163 | 393 | |
| 98 | CH₃ | CH₃ | F | 6-F | 4-Cl, 6-F | 180-184 | 397 | |
| 99 | CH₃ | CH₃ | F | 6-F | 3-Cl | | 379 | |
| 100 | CH₃ | CH₃ | F | 6-F | 4-CH₃, 6-Cl | 100-104 | 393 | |
| 101 | CH₃ | CH₃ | F | 4-F | 4,6-di-Cl | 176-180 | 414 | |
| 102 | CH₃ | CH₃ | F | 4-F | 4-Cl, 6-F | 136-140 | 397 | |
| 103 | CH₃ | CH₃ | Cl | 4-F | 4-CH₃CH₂O | 95-99 | 405 | |
| 104 | CH₃ | CH₃ | Cl | 4-F | 4-i-PrO | 99-103 | 419 | |
| 105 | CH₃ | CH₃ | F | 6-F | 4-CH₃ | | 359 | |
| 106 | CH₃ | CH₃ | Cl | 4,6-di-F | 4-CH₃ | | 392 | |
| 107 | CH₃ | CH₃ | F | 4-F | 4-CH₃ | | 359 | |
| 108 | CH₃ | CH₃ | Cl | 4-F | 6-Cl | 145-149 | 395 | |
| 109 | CH₃ | CH₃ | Cl | 4-F | 4,6-di-F | 158-162 | 397 | |
| 110 | CH₃ | CH₃ | Cl | 4-F | 6-Br | 151-155 | 439 | |
| 111 | CH₃ | CH₃ | Cl | 4-F | 4-F | 120-124 | 379 | |
| 112 (Ex. 1) | CH₃ | CH₃ | Cl | 4-F | 6-F | 130-134 | 379 | |
| 113 (Exs. 2 & 5) | CH₃ | CH₃ | Cl | 4-N≡C | 6-F | 176-180 | 386 | |
| 114 | CH₃ | CH₃ | F | 4-N≡C, 6-F | 6-F | 185-189 | 388 | |
| 115 | CH₃ | CH₃ | Cl | 4-N≡C | 4-Cl, 6-F | 185-189 | 420 | |
| 116 | CH₃ | CH₃ | Cl | 4-N≡C | 4,6-di-Cl | 216-220 | 436 | |
| 117 | CH₃ | CH₃ | Cl | 4-F | 6-CH₃ | 154-158 | 375 | |
| 118 | CH₃ | CH₃ | F | 4-F | 6-F | 113-117 | 363 | |
| 119 | CH₃ | CH₃ | Cl | 4-F | 4-CH₃O | 79-83 | 391 | |
| 120 | CH₃ | CH₃ | Cl | 4-N≡C | 4,6-di-F | 191-195 | 404 | |
| 121 | CH₃ | CH₃ | Cl | 4-F | 4-Cl, 6-F | 131-135 | 413 | |
| 122 | CH₃ | C≡N | Cl | 4-F | 6-F | 166-170 | 390 | |
| 123 | CH₃ | CH₃ | Cl | 4-N≡C | 6-Cl | 196-199 | 402 | |
| 124 | CH₃ | CH₃ | Cl | 4-N≡C | 4-CH₃O | 137-139 | 398 | |
| 125 | CH₃ | CH₃ | Cl | 4-N≡C | 6-Br | 209-211 | 446 | |
| 126 | CH₃ | CH₃ | Cl | 4-F | — | | 361 | |
| 127 | CH₃ | CH₃ | Cl | 4-N≡C | 4-CH₃, 6-F | 166-170 | 400 | |
| 128 | CH₃ | Et | Cl | 4-F | 4-Br, 6-Cl | | 489 | |
| 129 | CH₃ | Et | Cl | 4-F | 6-Cl | | 423 | |
| 130 | CH₃ | CH₃ | Cl | 4-F | 5-Cl | | 395 | |
| 131 | CH₃ | CH₃ | Br | 4-F | 4-Cl, 6-F | 151-155 | | |
| 132 | CH₃ | CH₃ | Cl | 4-Cl | 4-Br, 6-F | 159-163 | | |
| 133 | CH₃ | CH₃ | Cl | 4-Cl | 6-Cl | 208-212 | | |
| 134 | CH₃ | CH₃ | F | 4-N≡C | — | 125-129 | | |
| 135 | CH₃ | CH₃ | F | 6-F | — | 149-153 | | |
| 136 | CH₃ | CH₃ | Cl | 6-F | — | 152-156 | | |
| 137 | CH₃ | Et | Cl | 4-F | 4-CH₃, 6-F | | 407 | |
| 138 | CH₃ | CH₃ | Cl | 4-Cl | 4-CH₃O, 6-F | 103-107 | | |
| 139 | CH₃ | CH₃ | Br | 4-F | — | 119-123 | | |
| 140 | CH₃ | CH₃ | Cl | 4-MeO | — | 105-109 | | |
| 141 | CH₃ | CH₃ | F | 4-F | 4-CH₃O, 6-Cl | 156-160 | | |
| 142 | CH₃ | CH₃ | Cl | 4-Cl | 4-CH₃O | | 407 | |
| 143 | CH₃ | CH₃ | Cl | 4-Cl | 4-CH₃, 6-F | 158-162 | | |
| 144 | CH₃ | CH₃ | Cl | 4-Cl | 6-CH₃ | 206-210 | | |
| 145 | CH₃ | CH₃ | Cl | 4-Cl | 4-CH₃, 6-Cl | | | |
| 146 | CH₃ | CH₃ | Cl | 4-Cl | 4,6-di-Cl | 180-184 | | |
| 147 | CH₃ | CH₃ | F | 4-CH₃O, 6-F | — | | 375 | |
| 148 | CH₃ | CH₃ | Cl | 4,6-di-F | — | | 379 | |
| 149 | CH₃ | CH₃ | F | 4,6-di-F | — | | 363 | |
| 150 | CH₃ | CH₃ | F | 4-N≡C, 6-F | 4-CH₃O | 186-190 | | |
| 151 | CH₃ | CH₃ | F | 4-Cl, 6-F | 6-F | | 397 | |
| 152 | CH₃ | CH₃ | Cl | 4,6-di-F | 6-Cl | 152-156 | | |
| 153 | CH₃ | CH₃ | Cl | 4,6-di-F | 6-CH₃ | 141-145 | | |
| 154 | CH₃ | CH₃ | Br | 4,6-di-F | — | | 423 | |
| 155 | CH₃ | CH₃ | Cl | 4-N≡C | 4-Br, 6-F | 177-181 | | |
| 156 | CH₃ | CH₃ | Cl | 4-N≡C | 4-CH₃, 6-Cl | 230-234 | | |
| 157 | CH₃ | CH₃ | Cl | 4-N≡C | 6-CH₃ | 220-224 | | |

INDEX TABLE A-continued

A dash "—" in the $R^5$ column means that no $R^5$ substituent is present and the remaining carbon valences are occupied by hydrogen atoms.

| Cmpd. No. | $R^1$ | $R^2$ | $R^3$ | $(R^4)_m$ | $(R^5)_n$ | m.p. (° C.) | AP+ (M + 1) | AP− (M − 1) |
|---|---|---|---|---|---|---|---|---|
| 158 | CH₃ | CH₃ | F | 4,6-di-F | 6-Cl | 180-184 | | |
| 159 | CH₃ | CH₃ | F | 4,6-di-F | 4-CH₃O | | 392 | |
| 160 | CH₃ | CH₃ | F | 4-CH₃O, 6-F | 6-Cl | 168-172 | | |
| 161 | CH₃ | CH₃ | F | 4-CH₃O, 6-F | 4-CH₃O | | 405 | |
| 162 | CH₃ | CH₃ | F | 4-CH₃O, 6-F | 6-CH₃ | 154-158 | | |
| 163 | CH₃ | CH₃ | Br | 4,6-di-F | 6-Cl | 201-205 | | |
| 164 | CH₃ | CH₃ | Br | 4,6-di-F | 4-CH₃O | | 453 | |
| 165 | CH₃ | CH₃ | Br | 4-F | 4-CH₃O, 6-F | 177-181 | | |
| 166 | CH₃ | CH₃ | Cl | 4-N≡C | 4-CH₃O, 6-F | 185-189 | | |
| 167 | CH₃ | CH₃ | F | 4,6-di-F | 6-CH₃ | 151-155 | | |
| 168 | CH₃ | CH₃ | F | 4-Cl, 6-F | — | 118-122 | | |
| 169 | CH₃ | CH₃ | Br | 4,6-di-F | 6-CH₃ | 196-200 | | |
| 170 | CH₃ | Et | F | 4-Cl, 6-F | 6-F | 120-122 | | |
| 171 | CH₃ | Et | F | 4-F | 4-Br, 6-F | | 455 | |
| 173 | CH₃ | Et | Cl | 4-F | 4-CH₃O | | 405 | |
| 174 | CH₃ | Et | Cl | 4-F | 4-CH₃ | | | 388 |
| 175 | CH₃ | Et | F | 4-F | 4-CH₃ | | 373 | |
| 176 | CH₃ | CH₃ | F | 4-Cl | 4-F, 6-Cl | 184-188 | | |
| 177 | CH₃ | CH₃ | F | 4-F | 6-CH₃ | 130-134 | | |
| 178 | CH₃ | CH₃ | F | 4-F | 4-CH₃, 6-F | 108-112 | | |
| 179 | CH₃ | CH₃ | F | 4-N≡C | 4-CH₃O | 132-136 | | |
| 180 | CH₃ | CH₃ | Br | 4-N≡C | 4-CH₃O | 41-45 | | |
| 181 | CH₃ | CH₃ | Br | 4-F | 4-CH₃, 6-Cl | 174-178 | | |
| 182 | CH₃ | CH₃ | Cl | 4-CH₃O | 4-Br, 6-F | 180-184 | | |
| 183 | CH₃ | CH₃ | Cl | 4-CH₃O | 6-CH₃ | 208-212 | | |
| 184 | CH₃ | CH₃ | Cl | 4-CH₃O | 6-Cl | 189-193 | | |
| 185 | CH₃ | Et | F | 4-F | 4-CH₃, 6-F | | 391 | |
| 186 | CH₃ | CH₃ | Cl | 4-CH₃O | 4-CH₃O, 6-F | 156-160 | | |
| 187 | CH₃ | CH₃ | Cl | 4-CH₃O | 4-CH₃O | | 403 | |
| 188 | CH₃ | CH₃ | Cl | 4-CH₃O | 4-CH₃, 6-F | 135-139 | | |
| 189 | CH₃ | CH₃ | Cl | 4-Cl | — | | | 377 |
| 190 | CH₃ | CH₃ | F | 4-F | — | 132-136 | | |

INDEX TABLE B

| Cmpd. No. | Structure | AP+ (M + 1) |
|---|---|---|
| 172 | (structure shown) | 393 |

General protocol for preparing test suspensions for Tests A-F: the test compounds were first dissolved in acetone in an amount equal to 3% of the final volume and then suspended at the desired concentration (in ppm) in acetone and purified water (50/50 mix by volume) containing 250 ppm of the surfactant PEG400 (polyhydric alcohol esters). The resulting test suspensions were then used in Tests A-F.

Test A

The test solution was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 17 days, after which time disease ratings were made.

Test B

The test solution was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 7 days, after which time disease ratings were made.

Test C

The test suspension was sprayed to the point of run-off on wheat seedlings. The following day the seedlings were inoculated with a spore dust of *Blumeria graminis* f. sp. *tritici*, (also known as *Erysiphe graminis* f. sp. *tritici*, the causal agent of wheat powdery mildew) and incubated in a growth chamber at 20° C. for 8 days, after which time visual disease ratings were made.

Test D

The test solution was sprayed to the point of run-off on soybean seedlings. The following day the seedlings were inoculated with a spore suspension of *Phakopsora pachyrhizi* (the causal agent of Asian soybean rust) and incubated in a saturated atmosphere at 22° C. for 24 h and then moved to a growth chamber at 22° C. for 8 days, after which time visual disease ratings were made.

Test E

The test suspension was sprayed to the point of run-off on tomato seedlings. The following day the seedlings were inoculated with a spore suspension of *Botrytis cinerea* (the causal agent of tomato *Botrytis*) and incubated in a saturated atmosphere at 20° C. for 48 h, and then moved to a growth chamber at 24° C. for 3 days, after which time visual disease ratings were made.

Test F

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 3 days, after which time visual disease ratings were made.

Results for Tests A-F are given in Table A below. A rating of 100 indicates 100% disease control and a rating of 0 indicates no disease control (relative to the controls). A dash (-) indicates the compound was not tested.

TABLE A

| Cmpd. No. | Rate in ppm | Test A | Test B | Test C | Test D | Test E | Test F |
|---|---|---|---|---|---|---|---|
| 1 | 50 | 100 | 100 | 100 | 84 | 100 | 99 |
| 2 | 50 | 100 | 100 | 99 | 94 | 99 | 61 |
| 3 | 50 | 100 | 89 | 56 | 0 | 70 | 0 |
| 4 | 50 | — | 86 | 76 | 0 | 74 | 0 |
| 5 | 50 | 97 | 86 | 76 | 19 | 95 | 0 |
| 6 | 50 | — | 74 | 27 | 0 | 55 | 0 |
| 7 | 50 | 100 | 99 | 94 | 96 | 99 | 89 |
| 8 | 50 | 99 | 99 | 92 | 73 | 99 | 73 |
| 9 | 50 | 100 | 100 | 97 | 0 | 97 | 99 |
| 10 | 50 | 100 | 99 | 48 | 0 | 68 | 9 |
| 11 | 50 | 100 | 98 | 97 | 0 | 98 | 99 |
| 12 | 50 | 100 | 99 | 81 | 0 | 97 | 53 |
| 13 | 50 | 100 | 99 | 97 | 19 | 68 | 89 |
| 14 | 50 | 100 | 97 | 83 | 48 | 96 | 83 |
| 15 | 50 | 100 | 100 | 98 | 61 | 99 | 53 |
| 16 | 50 | 100 | 99 | 98 | 50 | 99 | 0 |
| 17 | 50 | 100 | 92 | 94 | 0 | 99 | 9 |
| 18 | 50 | 100 | 100 | 89 | 92 | 100 | 99 |
| 19 | 50 | 100 | 100 | 100 | 98 | 100 | 99 |
| 20 | 50 | 100 | 89 | 92 | 0 | 99 | 26 |
| 21 | 50 | 100 | 86 | 84 | 0 | 95 | 17 |
| 22 | 50 | 100 | 93 | 97 | 0 | 99 | 64 |
| 23 | 50 | 100 | 100 | 100 | 99 | 97 | 99 |
| 24 | 50 | 100 | 89 | 0 | 0 | 97 | 0 |
| 25 | 50 | 100 | 100 | 99 | 98 | 100 | 98 |
| 26 | 50 | 100 | 99 | 94 | 77 | 100 | 68 |
| 27 | 50 | 100 | 100 | 91 | 87 | 100 | 99 |
| 28 | 50 | 91 | 68 | 69 | 0 | 99 | 0 |
| 29 | 50 | 97 | 98 | 87 | 81 | 99 | 26 |
| 30 | 50 | 100 | 86 | 91 | 0 | 67 | 0 |
| 31 | 50 | 100 | 100 | 100 | 98 | 99 | 76 |
| 32 | 50 | 93 | 85 | 56 | 98 | 99 | 0 |
| 33 | 50 | 100 | 100 | 99 | 92 | 99 | 85 |
| 34 | 50 | 100 | 54 | 13 | 0 | 71 | 0 |
| 35 | 50 | 99 | 85 | 0 | 0 | 0 | 0 |
| 36 | 50 | 100 | 89 | 56 | 25 | 100 | 0 |
| 37 | 50 | 100 | 100 | 98 | 0 | 88 | 78 |
| 38 | 50 | 100 | 99 | 95 | 0 | 88 | 0 |
| 39 | 50 | 100 | 100 | 99 | 73 | 88 | 99 |
| 40 | 50 | 100 | 100 | 100 | 82 | 98 | 100 |
| 41 | 50 | 100 | 100 | 94 | 77 | 77 | 0 |
| 42 | 50 | 100 | 100 | 96 | 0 | 91 | 0 |
| 43 | 50 | 100 | 100 | 97 | 65 | 96 | 64 |
| 44 | 50 | 100 | 99 | 98 | 0 | 95 | 46 |
| 45 | 50 | 100 | 86 | 95 | 0 | 99 | 33 |
| 46 | 50 | 100 | 98 | 99 | 0 | 99 | 81 |
| 47 | 50 | 100 | 97 | 89 | 92 | 95 | 96 |
| 48 | 50 | 100 | 95 | 89 | 0 | 97 | 97 |
| 49 | 50 | 100 | 100 | 95 | 25 | 94 | 26 |
| 50 | 50 | 100 | 98 | 100 | 0 | 92 | 98 |
| 51 | 50 | 100 | 100 | 100 | 79 | 98 | 99 |
| 52 | 50 | 100 | 100 | 90 | 59 | 99 | 94 |
| 53 | 50 | 100 | 100 | 98 | 0 | 98 | 98 |
| 54 | 50 | 100 | 91 | 93 | 0 | 21 | 0 |
| 55 | 50 | 100 | 99 | 90 | 0 | 34 | 0 |
| 56 | 50 | 100 | 100 | 100 | 65 | 99 | 99 |
| 57 | 50 | 100 | 100 | 100 | 96 | 100 | 100 |

TABLE A-continued

| Cmpd. No. | Rate in ppm | Test A | Test B | Test C | Test D | Test E | Test F |
|---|---|---|---|---|---|---|---|
| 58 | 50 | 100 | 100 | 99 | 36 | 99 | 99 |
| 59 | 50 | 100 | 100 | 99 | 96 | 99 | 92 |
| 60 | 50 | 100 | 100 | 100 | 97 | 99 | 99 |
| 60 | 10 | 99 | 100 | 85 | 0 | 99 | 75 |
| 61 | 50 | 100 | 100 | 99 | 84 | 99 | 99 |
| 62 | 50 | 100 | 100 | 100 | 100 | 99 | 99 |
| 63 | 50 | 100 | 99 | 86 | 0 | 100 | 96 |
| 64 | 50 | 100 | 100 | 98 | 97 | 98 | 99 |
| 65 | 50 | 94 | 89 | 56 | 66 | 16 | 46 |
| 66 | 50 | 100 | 100 | 98 | 97 | 98 | 96 |
| 67 | 50 | 100 | 100 | 89 | 69 | 98 | 33 |
| 68 | 50 | 100 | 100 | 100 | 99 | 100 | 99 |
| 68 | 10 | 100 | 100 | 96 | 32 | 100 | 98 |
| 69 | 50 | 100 | 100 | 97 | 77 | 100 | 99 |
| 70 | 50 | 100 | 100 | 99 | 84 | 99 | 99 |
| 71 | 50 | 100 | 100 | 99 | 82 | 99 | 98 |
| 72 | 50 | 100 | 100 | 99 | 31 | 98 | 99 |
| 72 | 10 | 100 | 85 | 81 | 12 | 98 | 63 |
| 73 | 50 | 100 | 100 | 96 | 98 | 99 | 97 |
| 74 | 50 | 99 | 86 | 81 | 74 | 99 | 85 |
| 75 | 50 | 100 | 99 | 90 | 0 | 57 | 98 |
| 76 | 50 | 100 | 99 | 95 | 25 | 87 | 0 |
| 77 | 50 | 100 | 100 | 95 | 73 | 72 | 9 |
| 78 | 50 | 100 | 89 | 95 | 0 | 68 | 0 |
| 79 | 50 | 100 | 100 | 91 | 44 | 98 | 0 |
| 80 | 50 | 100 | 100 | 97 | 50 | 95 | 98 |
| 81 | 50 | 100 | 99 | 89 | 0 | 95 | 99 |
| 82 | 50 | 100 | 100 | 58 | 59 | 96 | 97 |
| 83 | 50 | 99 | 91 | 99 | 0 | 98 | 99 |
| 84 | 50 | 100 | 100 | 99 | 48 | 90 | 99 |
| 85 | 50 | 100 | 100 | 97 | 96 | 94 | 98 |
| 86 | 50 | 100 | 100 | 98 | 77 | 96 | 99 |
| 87 | 50 | — | 99 | 98 | 0 | 98 | 93 |
| 88 | 50 | — | 97 | 84 | 0 | 99 | 9 |
| 89 | 50 | — | 100 | 99 | 80 | 99 | 99 |
| 90 | 50 | 100 | 95 | 87 | 0 | 99 | 9 |
| 91 | 50 | 99 | 88 | 84 | 0 | 99 | 26 |
| 92 | 50 | 100 | 96 | 89 | 0 | 100 | 79 |
| 93 | 50 | 100 | 100 | 99 | 100 | 100 | 99 |
| 93 | 10 | 99 | 100 | 97 | 87 | 99 | 99 |
| 94 | 50 | 73 | 0 | 72 | 73 | 0 | 9 |
| 95 | 50 | 100 | 100 | 100 | 84 | 99 | 99 |
| 96 | 50 | 100 | 95 | 0 | 0 | 80 | 0 |
| 97 | 50 | 100 | 100 | 100 | 96 | 100 | 99 |
| 98 | 50 | 100 | 97 | 93 | 0 | 99 | 98 |
| 99 | 50 | 99 | 0 | 0 | 0 | 24 | 0 |
| 100 | 50 | 100 | 89 | 21 | 0 | 26 | 0 |
| 101 | 50 | 100 | 99 | 89 | 44 | 99 | 0 |
| 102 | 50 | 100 | 100 | 100 | 48 | 99 | 99 |
| 103 | 50 | 97 | 80 | 50 | 0 | 83 | 0 |
| 104 | 50 | 60 | 0 | 72 | 0 | 0 | 0 |
| 105 | 50 | 99 | 74 | 86 | 0 | 73 | 0 |
| 106 | 50 | — | 100 | 98 | 0 | 99 | 68 |
| 107 | 50 | — | 91 | 61 | 0 | 98 | 0 |
| 108 | 50 | 100 | 100 | 97 | 86 | 100 | 77 |
| 109 | 50 | 100 | 100 | 100 | 93 | 100 | 99 |
| 110 | 50 | 100 | 98 | 56 | 73 | 99 | 0 |
| 111 | 50 | 100 | 99 | 99 | 0 | 100 | 93 |
| 112 | 50 | 88 | 100 | 100 | 99 | 100 | 100 |
| 112 | 10 | 72 | 100 | 98 | 52 | 100 | 98 |
| 113 | 50 | 100 | 99 | 97 | 13 | 99 | 99 |
| 114 | 50 | 100 | 98 | 99 | 73 | 100 | 99 |
| 115 | 50 | 100 | 100 | 94 | 77 | 99 | 99 |
| 116 | 50 | 99 | 99 | 56 | 0 | 63 | 82 |
| 117 | 50 | 99 | 100 | 95 | 0 | 99 | 76 |
| 118 | 50 | 100 | 100 | 98 | 0 | 100 | 99 |
| 118 | 10 | 100 | 80 | 27 | 0 | 99 | 60 |
| 119 | 50 | 100 | 100 | 99 | 92 | 100 | 99 |
| 120 | 50 | 100 | 100 | 89 | 44 | 100 | 99 |
| 121 | 50 | 100 | 100 | 100 | 99 | 100 | 100 |
| 122 | 50 | 100 | 100 | 94 | 0 | 100 | 99 |
| 123 | 50 | 100 | 97 | 81 | 0 | 100 | 66 |
| 124 | 50 | 100 | 100 | 99 | 25 | 100 | 99 |
| 125 | 50 | 100 | 96 | 0 | 0 | 99 | 9 |
| 126 | 50 | 98 | 85 | 96 | 0 | 100 | 68 |
| 127 | 50 | 100 | 99 | 92 | 96 | 100 | 100 |
| 128 | 50 | 100 | 98 | 96 | 31 | 99 | 33 |
| 129 | 50 | 100 | 100 | 97 | 84 | 99 | 88 |

TABLE A-continued

| Cmpd. No. | Rate in ppm | Test A | Test B | Test C | Test D | Test E | Test F |
|---|---|---|---|---|---|---|---|
| 130 | 50 | 85 | 86 | 20 | 0 | 85 | 0 |
| 131 | 50 | 100 | 100 | 99 | 80 | 99 | 100 |
| 132 | 50 | 100 | 98 | 47 | 0 | 99 | 96 |
| 133 | 50 | 100 | 86 | 0 | 0 | 97 | 0 |
| 134 | 50 | 100 | 23 | 71 | 0 | 70 | 0 |
| 135 | 50 | 100 | 68 | 93 | 0 | 99 | 0 |
| 136 | 50 | 100 | 80 | 88 | 0 | 99 | 0 |
| 137 | 50 | 100 | 100 | 100 | 91 | 99 | 99 |
| 138 | 50 | 100 | 100 | 93 | 67 | 99 | 100 |
| 139 | 50 | 98 | 86 | 76 | 0 | 100 | 33 |
| 140 | 50 | 99 | 86 | 31 | 0 | 100 | 93 |
| 141 | 50 | 99 | 100 | 99 | 0 | 99 | 83 |
| 142 | 50 | 100 | 91 | 39 | 25 | 99 | 80 |
| 143 | 50 | 99 | 100 | 96 | 87 | 99 | 100 |
| 144 | 50 | 100 | 68 | 35 | 69 | 0 | 0 |
| 145 | 50 | 98 | 92 | 52 | 0 | 85 | 24 |
| 146 | 50 | 97 | 98 | 0 | 0 | 0 | 40 |
| 147 | 50 | 96 | 86 | 97 | 0 | 100 | 99 |
| 148 | 50 | 100 | 99 | 98 | 13 | 99 | 100 |
| 149 | 50 | 100 | 80 | 97 | 0 | 99 | 96 |
| 150 | 50 | 100 | 100 | 98 | 13 | 100 | 99 |
| 151 | 50 | 100 | 100 | 99 | 0 | 99 | 99 |
| 152 | 50 | 99 | 100 | 98 | 91 | 99 | 92 |
| 153 | 50 | 99 | 100 | 99 | 73 | 99 | 72 |
| 154 | 50 | 99 | 80 | 98 | 0 | 99 | 51 |
| 155 | 50 | 99 | 99 | 90 | 0 | 100 | 93 |
| 156 | 50 | 91 | 91 | 66 | 0 | 0 | 0 |
| 157 | 50 | 100 | 97 | 76 | 0 | 9 | 0 |
| 158 | 50 | 99 | 100 | 99 | 87 | 99 | 83 |
| 159 | 50 | 100 | 100 | 100 | 13 | 99 | 99 |
| 160 | 50 | 98 | 100 | 96 | 86 | 100 | 99 |
| 161 | 50 | 100 | 100 | 100 | 0 | 100 | 99 |
| 162 | 50 | 100 | 100 | 99 | 77 | 97 | 98 |
| 163 | 50 | 99 | 100 | 98 | 78 | 88 | 76 |
| 164 | 50 | 100 | 100 | 98 | 0 | 100 | 99 |
| 165 | 50 | 99 | 100 | 98 | 94 | 100 | 100 |
| 166 | 50 | 99 | 100 | 98 | 98 | 99 | 100 |
| 167 | 50 | 100 | 100 | 98 | 65 | 95 | 98 |
| 168 | 50 | 100 | 74 | 97 | 0 | 99 | 40 |
| 169 | 50 | 100 | 100 | 100 | 0 | 98 | 0 |
| 170 | 50 | 100 | 99 | 99 | 0 | 100 | 99 |
| 171 | 50 | 100 | 91 | 99 | 0 | 97 | 88 |
| 172 | 50 | 100 | 100 | 100 | 0 | 99 | 40 |
| 173 | 50 | 100 | 100 | 98 | 0 | 98 | 93 |
| 174 | 50 | 100 | 95 | 92 | 0 | 99 | 39 |
| 175 | 50 | 100 | 86 | 79 | 0 | 88 | 0 |
| 176 | 50 | 100 | 97 | 0 | 0 | 9 | 0 |
| 177 | 50 | 100 | 97 | 50 | 0 | 100 | 9 |
| 178 | 50 | 100 | 100 | 99 | 97 | 100 | 100 |
| 179 | 50 | 100 | 96 | 93 | 0 | 99 | 85 |
| 180 | 50 | 100 | 98 | 79 | 0 | 99 | 98 |
| 181 | 50 | 100 | 100 | 99 | 78 | 99 | 99 |
| 182 | 50 | 100 | 99 | 76 | 0 | 100 | 99 |
| 183 | 50 | 100 | 99 | 78 | 0 | 100 | 58 |
| 184 | 50 | 100 | 100 | 21 | 0 | 100 | 26 |

BIOLOGICAL COMPARATIVE EXAMPLES

General protocol for preparing test suspensions for Tests A1-F1: the test compounds were first dissolved in acetone in an amount equal to 3% of the final volume and then suspended at the desired concentration (in ppm) in acetone and purified water (50/50 mix by volume) containing 250 ppm of the surfactant PEG400 (polyhydric alcohol esters). The resulting test suspensions were then used in Tests A1-F1.

Test A1

The test solution was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 17 days, after which time disease ratings were made.

Test B1

The test solution was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 7 days, after which time disease ratings were made.

Test C1

The test suspension was sprayed to the point of run-off on wheat seedlings. The following day the seedlings were inoculated with a spore dust of *Blumeria graminis* f. sp. *tritici*, (also known as *Erysiphe graminis* f. sp. *tritici*, the causal agent of wheat powdery mildew) and incubated in a growth chamber at 20° C. for 8 days, after which time visual disease ratings were made.

Test E1

The test suspension was sprayed to the point of run-off on tomato seedlings. The following day the seedlings were inoculated with a spore suspension of *Botrytis cinerea* (the causal agent of tomato *Botrytis*) and incubated in a saturated atmosphere at 20° C. for 48 h, and then moved to a growth chamber at 24° C. for 3 days, after which time visual disease ratings were made.

Test F1

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 3 days, after which time visual disease ratings were made.

Results for Tests A1-F1 are given in Table B below. A rating of 100 indicates 100% disease control and a rating of 0 indicates no disease control (relative to the controls). The data is presented for the following compounds:

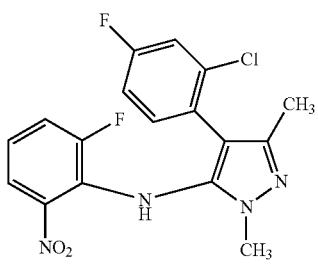

Cmpd. No. 112 (present invention)

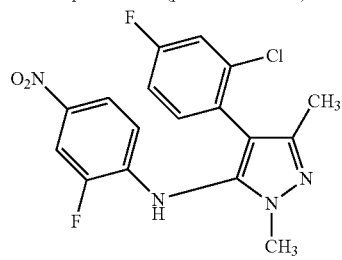

Cmpd. known from WO 2010/101973

TABLE B

|  | Rate in ppm | Test A1 | Test B1 | Test C1 | Test E1 | Test F1 |
| --- | --- | --- | --- | --- | --- | --- |
| Cmpd. No. 112 | 50 | 100 | 100 | 98 | 99 | 100 |
|  | 10 | 81 | 86 | 97 | 99 | 99 |
| Cmpd. from | 50 | 91 | 0 | 0 | 40 | 0 |
| WO 2010/101973 | 10 | 45 | 0 | 0 | 0 | 0 |

What is claimed is:

1. A compound of Formula 1 and salts thereof, wherein Formula 1 is:

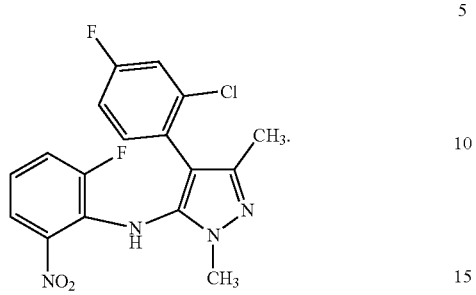

2. A fungicidal composition comprising (a) a compound of claim 1; and (b) at least one other fungicide.

3. A fungicidal composition comprising (a) a compound of claim 1; and (b) at least one additional component selected from the group consisting of surfactants, solid diluents and liquid diluents.

4. A method for protecting a plant from a *Septoria* disease comprising applying to the plant or portion thereof, or to the plant seed, a fungicidally effective amount of a compound of claim 1.

* * * * *